United States Patent
Ma et al.

(10) Patent No.: US 9,969,803 B2
(45) Date of Patent: *May 15, 2018

(54) MONOCLONAL ANTIBODIES THAT INHIBIT THE WNT SIGNALING PATHWAY AND METHODS OF PRODUCTION AND USE THEREOF

(71) Applicant: The Board of Regents of the University of Oklahoma, Norman, OK (US)

(72) Inventors: Jian-xing Ma, Edmond, OK (US); Kyungwon Lee, Oklahoma City, OK (US); Ying Chen, Oklahoma City, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/089,937

(22) Filed: Apr. 4, 2016

(65) Prior Publication Data

US 2016/0229909 A1 Aug. 11, 2016

Related U.S. Application Data

(60) Continuation of application No. 14/299,570, filed on Jun. 9, 2014, now Pat. No. 9,303,087, which is a division of application No. 13/031,010, filed on Feb. 18, 2011, now Pat. No. 8,859,736.

(60) Provisional application No. 61/306,083, filed on Feb. 19, 2010.

(51) Int. Cl.
*A61K 39/395* (2006.01)
*C07K 16/28* (2006.01)
*A61K 9/00* (2006.01)
*A61K 45/06* (2006.01)
*C07K 16/30* (2006.01)
*A61K 39/00* (2006.01)

(52) U.S. Cl.
CPC ............ *C07K 16/28* (2013.01); *A61K 9/0048* (2013.01); *A61K 39/3955* (2013.01); *A61K 45/06* (2013.01); *C07K 16/30* (2013.01); *A61K 2039/505* (2013.01); *C07K 2317/24* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/624* (2013.01); *C07K 2317/76* (2013.01); *C07K 2317/92* (2013.01)

(58) Field of Classification Search
None
See application file for complete search history.

(56) References Cited

U.S. PATENT DOCUMENTS 7,700,101 B2 4/2010 Allen et al.
7,838,252 B2 11/2010 Cohen et al.

FOREIGN PATENT DOCUMENTS

WO  WO 02-092015   11/2002
WO  WO 06-089114   8/2006
WO  2009064944 A2  5/2009

OTHER PUBLICATIONS

Young, et al.; "LRP5 and LRP6 are not required for protective antigen-mediated internalization or lethality of anthrax lethal toxin"; PLos Pathogens, vol. 3:3, e27 (see whole document) (2007).
Hassler, et al.; "Kremen is required for neural crest induction in Xenopus and promotes LRP6-mediated Wnt signaling"; Development, vol. 134:4255-4263 (see whole document) (2007).
Binnerts, et al.; "The first propeller domain of LRP6 regulates sensitivity of DKK1"; Molecular Biology, vol. 20:3552-3560 (see whole document) (2009).
Rudikoff, et al.; "Single amino acid substitution altering antigen-binding specificity"; Proc Natl Acad Sci USA; vol. 79:1979-1983 (1982).
MacCullum et al.; "Antibody-antigen Interactions: Contact Analysis and Binding Site Topography"; J. Mal. Biol., 262, pp. 732-745 (1996).
DePascalis et al.; "Grafting of 'Abbreviated' Complementarity-Determining Regions Containing Specificity-Determining Residues Essential for Ligand Contact to Engineer a Less Immunogenic Humanized Monoclonal Antidoby"; The Journal of Immunology, 169, pp. 3076-3084 (2002).
Casset et al.; "A peptide mimetic of an anti-CD4 monoclonal antibody by rational design"; BBRC 307:198-205 (2003).
Vajdos et al.; "Comprehensive Functional Maps of the Antigen-binding Site of an Anti-ErbB2 Antibody Obtained with Shotgun Scanning Mutagenesis"; J. Mol. Biol. 320, pp. 415-428 (2002).
Chen et al.; "Selection and Analysis of an Optimized Anti-VEGF Antibody: Crystal Structure of an Affinity-matured Fab in Complex with Antigen"; J. Mol. Bio. 293, pp. 865-881 (1999).
Wu et al.; "Humanization of a Murine Monoclonal Antibody by Simultaneous Optimization of Framework and CDR Residues"; J. Mol. Biol. 294, pp. 151+162 (1999).
Padlan et al.; "Structure of an antibody-antigen complex: Crystal structure of the HyHEL-10 Fab-lysozyme complex"; PNAS 86:5938-5942 (1989).

(Continued)

*Primary Examiner* — Laura B Goddard
*Assistant Examiner* — Meera Natarajan
(74) *Attorney, Agent, or Firm* — Dunlap Codding, P.C.

(57) ABSTRACT

Monoclonal antibodies against LRP6 and that block the Wnt signaling pathway are disclosed. Methods of production and use thereof are also disclosed.

22 Claims, 15 Drawing Sheets

(10 of 15 Drawing Sheet(s) Filed in Color)

(56) References Cited

OTHER PUBLICATIONS

Lamminmaki et al.; "Crystal Structure of a Recombinant Anti-estradiol Fab Fragment in Complex with 17B-Estradiol", JBC 276:36687-36694 (2001).
Foote, et al., "Antibody Framework Residues Affecting the Conformation of the Hypervariable Loops," Journal of Molecular Biology, (1992), vol. 224, pp. 487-499.
Carter, et al.; "Humanization of an anti-p185HER2 antibody for human cancer therapy," Proc. National Academy Science (1992), vol. 89, pp. 4285-4289.
Japanese Patent Application No. 2012-554056; Jian-xing Ma, et al.; Office Action dated Apr. 15, 2015.
AU Application No. 2011217964; MA, et al.; Examination Report No. 2 dated May 5, 2016.

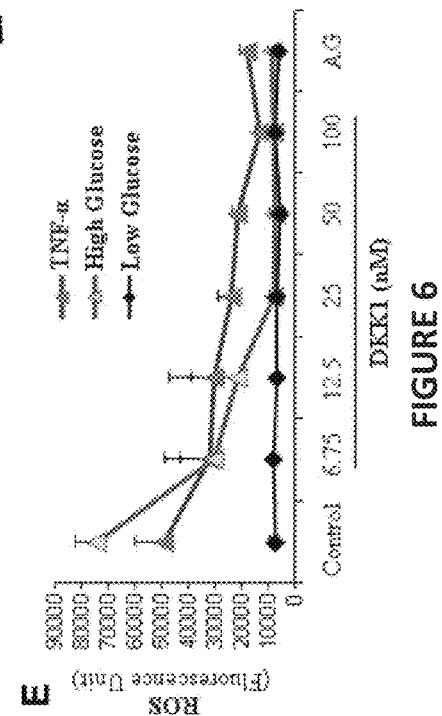
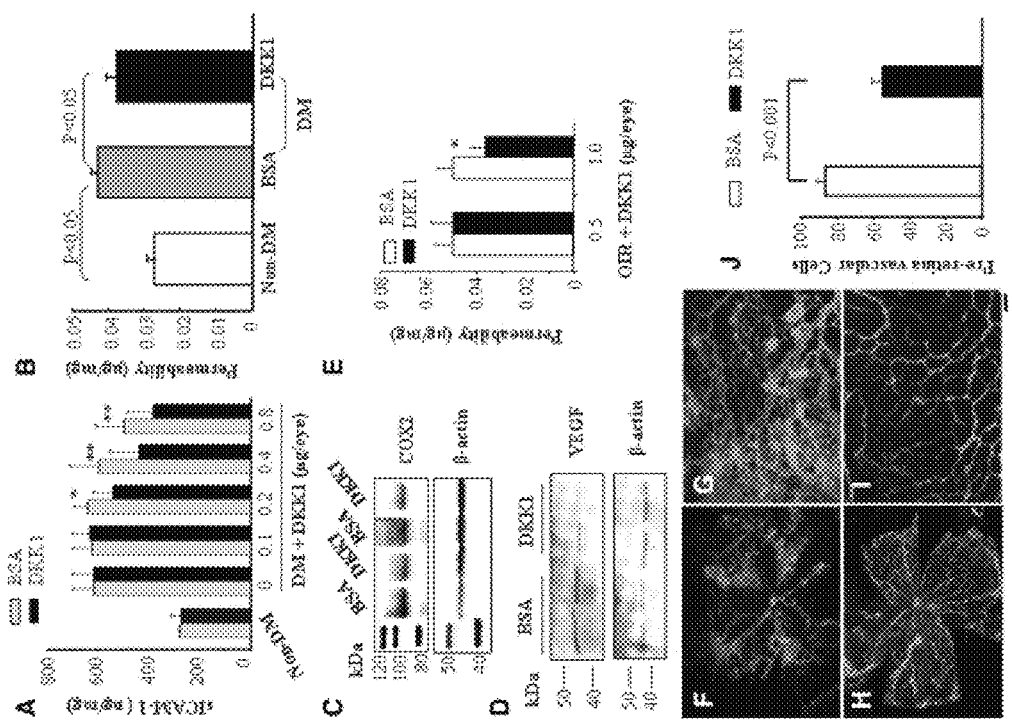
FIGURE 5
FIGURE 6

SEQUENCE LISTING

```
<160> NUMBER OF SEQ ID NOS: 19

<210> SEQ ID NO 1
<211> LENGTH: 1613
<212> TYPE: PRT
<213> ORGANISM: Homo sapiens

<400> SEQUENCE: 1

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
                100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175
```

```
Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590
```

Ala Glu Glu Asn Gly Gly Cys Ser His Leu Cys Leu Tyr Arg Pro Gln
            595                 600                 605

Gly Leu Arg Cys Ala Cys Pro Ile Gly Phe Glu Leu Ile Ser Asp Met
610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
            675                 680                 685

Ala Phe Met Asn Gly Ser Ala Leu Glu His Val Val Glu Phe Gly Leu
        690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
        770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
        995                 1000                1005

Ser Gln Asn Leu Glu Ile Gln Pro Tyr Asp Leu Ser Ile Asp Ile

```
            1010                1015                1020
Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Val Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410
```

-continued

```
Val Val His Gly Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 2
<211> LENGTH: 675
<212> TYPE: PRT
<213> ORGANISM: Homo sapiens

<400> SEQUENCE: 2

Ala Pro Leu Leu Leu Tyr Ala Asn Arg Arg Asp Leu Arg Leu Val Asp
1               5                   10                  15

Ala Thr Asn Gly Lys Glu Asn Ala Thr Ile Val Val Gly Gly Leu Glu
                20                  25                  30

Asp Ala Ala Ala Val Asp Phe Val Phe Ser His Gly Leu Ile Tyr Trp
            35                  40                  45

Ser Asp Val Ser Glu Glu Ala Ile Lys Arg Thr Glu Phe Asn Lys Thr
        50                  55                  60

Glu Ser Val Gln Asn Val Val Ser Gly Leu Leu Ser Pro Asp Gly
65                  70                  75                  80

Leu Ala Cys Asp Trp Leu Gly Leu Lys Leu Tyr Trp Thr Asp Ser Glu
                85                  90                  95

Thr Asn Arg Ile Glu Val Ser Asn Leu Asp Gly Ser Leu Arg Lys Val
            100                 105                 110

Leu Phe Trp Gln Glu Leu Asp Gln Pro Arg Ala Ile Ala Leu Asp Pro
        115                 120                 125

Ser Ser Gly Phe Met Tyr Trp Thr Asp Trp Gly Glu Val Pro Lys Ile
    130                 135                 140

Glu Arg Ala Gly Met Asp Gly Ser Ser Arg Phe Ile Ile Ile Asn Ser
```

```
            145                 150                 155                 160
Glu Ile Tyr Trp Pro Asn Gly Leu Thr Leu Asp Tyr Glu Glu Gln Lys
                    165                 170                 175
Leu Tyr Trp Ala Asp Ala Lys Leu Asn Phe Ile His Lys Ser Asn Leu
                    180                 185                 190
Asp Gly Thr Asn Arg Gln Ala Val Val Lys Gly Ser Leu Pro His Pro
                    195                 200                 205
Phe Ala Leu Thr Leu Phe Glu Asp Ile Leu Tyr Trp Thr Asp Trp Ser
    210                 215                 220
Thr His Ser Ile Leu Ala Cys Asn Lys Tyr Thr Gly Glu Gly Leu Arg
225                 230                 235                 240
Glu Ile His Ser Asp Ile Phe Ser Pro Met Asp Ile His Ala Phe Ser
                245                 250                 255
Gln Gln Arg Gln Pro Asn Ala Thr Asn Pro Cys Gly Ile Asp Asn Gly
                260                 265                 270
Gly Cys Ser His Leu Cys Leu Met Ser Pro Val Lys Pro Phe Tyr Gln
            275                 280                 285
Cys Ala Cys Pro Thr Gly Val Lys Leu Leu Glu Asn Gly Lys Thr Cys
            290                 295                 300
Lys Asp Gly Ala Thr Glu Leu Leu Leu Leu Ala Arg Arg Thr Asp Leu
305                 310                 315                 320
Arg Arg Ile Ser Leu Asp Thr Pro Asp Phe Thr Asp Ile Val Leu Gln
                325                 330                 335
Leu Glu Asp Ile Arg His Ala Ile Ala Ile Asp Tyr Asp Pro Val Glu
                340                 345                 350
Gly Tyr Ile Tyr Trp Thr Asp Asp Glu Val Arg Ala Ile Arg Arg Ser
                355                 360                 365
Phe Ile Asp Gly Ser Gly Ser Gln Phe Val Val Thr Ala Gln Ile Ala
    370                 375                 380
His Pro Asp Gly Ile Ala Val Asp Trp Val Ala Arg Asn Leu Tyr Trp
385                 390                 395                 400
Thr Asp Thr Gly Thr Asp Arg Ile Glu Val Thr Arg Leu Asn Gly Thr
                405                 410                 415
Met Arg Lys Ile Leu Ile Ser Glu Asp Leu Glu Glu Pro Arg Ala Ile
                420                 425                 430
Val Leu Asp Pro Met Val Gly Tyr Met Tyr Trp Thr Asp Trp Gly Glu
                435                 440                 445
Ile Pro Lys Ile Glu Arg Ala Ala Leu Asp Gly Ser Asp Arg Val Val
    450                 455                 460
Leu Val Asn Thr Ser Leu Gly Trp Pro Asn Gly Leu Ala Leu Asp Tyr
465                 470                 475                 480
Asp Glu Gly Lys Ile Tyr Trp Gly Asp Ala Lys Thr Asp Lys Ile Glu
                485                 490                 495
Val Met Asn Thr Asp Gly Thr Gly Arg Arg Val Leu Val Glu Asp Lys
                500                 505                 510
Ile Pro His Ile Phe Gly Phe Thr Leu Leu Gly Asp Tyr Val Tyr Trp
            515                 520                 525
Thr Asp Trp Gln Arg Arg Ser Ile Glu Arg Val His Lys Arg Ser Ala
            530                 535                 540
Glu Arg Glu Val Ile Ile Asp Gln Leu Pro Asp Leu Met Gly Leu Lys
545                 550                 555                 560
Ala Thr Asn Val His Arg Val Ile Gly Ser Asn Pro Cys Ala Glu Glu
                565                 570                 575
```

```
Asn Gly Gly Cys Ser His Leu Cys Leu Tyr Arg Pro Gln Gly Leu Arg
            580                 585                 590

Cys Ala Cys Pro Ile Gly Phe Glu Leu Ile Ser Asp Met Lys Thr Cys
            595                 600                 605

Ile Val Pro Glu Ala Phe Leu Leu Phe Ser Arg Arg Ala Asp Ile Arg
610                 615                 620

Arg Ile Ser Leu Glu Thr Asn Asn Asn Val Ala Ile Pro Leu Thr
625                 630                 635                 640

Gly Val Lys Glu Ala Ser Ala Leu Asp Phe Asp Val Thr Asp Asn Arg
            645                 650                 655

Ile Tyr Trp Thr Asp Ile Ser Leu Lys Thr Ile Ser Arg Ala Phe Met
            660                 665                 670

Asn Gly Ser
            675

<210> SEQ ID NO 3
<211> LENGTH: 296
<212> TYPE: PRT
<213> ORGANISM: Homo sapiens

<400> SEQUENCE: 3

Asp Gly Ala Thr Glu Leu Leu Leu Ala Arg Arg Thr Asp Leu Arg
1               5                   10                  15

Arg Ile Ser Leu Asp Thr Pro Asp Phe Thr Asp Ile Val Leu Gln Leu
                20                  25                  30

Glu Asp Ile Arg His Ala Ile Ala Ile Asp Tyr Asp Pro Val Glu Gly
            35                  40                  45

Tyr Ile Tyr Trp Thr Asp Asp Glu Val Arg Ala Ile Arg Arg Ser Phe
    50                  55                  60

Ile Asp Gly Ser Gly Ser Gln Phe Val Val Thr Ala Gln Ile Ala His
65                  70                  75                  80

Pro Asp Gly Ile Ala Val Asp Trp Val Ala Arg Asn Leu Tyr Trp Thr
                85                  90                  95

Asp Thr Gly Thr Asp Arg Ile Glu Val Thr Arg Leu Asn Gly Thr Met
            100                 105                 110

Arg Lys Ile Leu Ile Ser Glu Asp Leu Glu Glu Pro Arg Ala Ile Val
        115                 120                 125

Leu Asp Pro Met Val Gly Tyr Met Tyr Trp Thr Asp Trp Gly Glu Ile
130                 135                 140

Pro Lys Ile Glu Arg Ala Ala Leu Asp Gly Ser Asp Arg Val Val Leu
145                 150                 155                 160

Val Asn Thr Ser Leu Gly Trp Pro Asn Gly Leu Ala Leu Asp Tyr Asp
                165                 170                 175

Glu Gly Lys Ile Tyr Trp Gly Asp Ala Lys Thr Asp Lys Ile Glu Val
            180                 185                 190

Met Asn Thr Asp Gly Thr Gly Arg Arg Val Leu Val Glu Asp Lys Ile
        195                 200                 205

Pro His Ile Phe Gly Phe Thr Leu Leu Gly Asp Tyr Val Tyr Trp Thr
    210                 215                 220

Asp Trp Gln Arg Arg Ser Ile Glu Arg Val His Lys Arg Ser Ala Glu
225                 230                 235                 240

Arg Glu Val Ile Ile Asp Gln Leu Pro Asp Leu Met Gly Leu Lys Ala
                245                 250                 255

Thr Asn Val His Arg Val Ile Gly Ser Asn Pro Cys Ala Glu Glu Asn
```

Gly Gly Cys Ser His Leu Cys Leu Tyr Arg Pro Gln Gly Leu Arg Cys
       260                 265                 270

Ala Cys Pro Ile Gly Phe Glu Leu
    275                 280         285

290                 295

<210> SEQ ID NO 4
<211> LENGTH: 361
<212> TYPE: DNA
<213> ORGANISM: Mus musculus

<400> SEQUENCE: 4
gaggtgcagc ttgttgagtc tggtggagga ttggtgcagt ctaaagggtc attgaaactc      60
tcatgtgcag cctctggatt caccttcaat acctacgcca tgaactgggt ccgccaggct     120
ccaggaaggg tttggaatgg gttggtcgca taagaagtaa atataataat tatgtaacat     180
attatggcga ttcagtgaaa gacaggttca ccatttccag agatgattca caaagcatgc     240
tctatctgca aatgacaact tgaaaactga ggacacagcc atgtattact gtgtgagaca     300
aggtagggga tcctatgcta tggactactg gggtcaagga acctcagtca ccgtctcctc     360
a                                                                    361

<210> SEQ ID NO 5
<211> LENGTH: 121
<212> TYPE: PRT
<213> ORGANISM: Mus musculus

<400> SEQUENCE: 5

Glu Val Gln Leu Val Glu Ser Gly Gly Gly Leu Val Gln Ser Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Val Thr Tyr Tyr Gly Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Gly Arg Gly Ser Tyr Ala Met Asp Tyr Trp Gly
            100                 105                 110

Gln Gly Thr Ser Val Thr Val Ser Ser
        115                 120

<210> SEQ ID NO 6
<211> LENGTH: 319
<212> TYPE: DNA
<213> ORGANISM: Mus musculus

<400> SEQUENCE: 6
aacattgtaa tgacccaatc tcccaaatcc atgtccatgt cagtaggaga gagggtcacc      60
ttgagctgca aggccagtga aaatgtgggt acttatgtat cctggtatca acagaaacca     120
gagcagttcc taaactgctg atatacgggg catccaatag gtacactggg gtccccgatc     180
gattcatagg cagtggatct gcaacagatt tcactctgac catcagaagt gtgcaggctg     240
aagaccttgc agattatcac tgtggacaga gttacagcta tcccacgttc ggtgctggga     300
caagctggag ctgaaacgg    319

<210> SEQ ID NO 7
<211> LENGTH: 107
<212> TYPE: PRT
<213> ORGANISM: Mus musculus

<400> SEQUENCE: 7

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Ile Gly
    50                  55                  60

Ser Gly Ser Ala Thr Asp Phe Thr Leu Thr Ile Arg Ser Val Gln Ala
65                  70                  75                  80

Glu Asp Leu Ala Asp Tyr His Cys Gly Gln Ser Tyr Ser Tyr Pro Thr
                85                  90                  95

Phe Gly Ala Gly Thr Lys Leu Glu Leu Lys Arg
            100                 105

<210> SEQ ID NO 8
<211> LENGTH: 30
<212> TYPE: DNA
<213> ORGANISM: Mus musculus

<400> SEQUENCE: 8
ggattcacct tcaataccta cgccatgaac    30

<210> SEQ ID NO 9
<211> LENGTH: 10
<212> TYPE: PRT
<213> ORGANISM: Mus musculus

<400> SEQUENCE: 9

Gly Phe Thr Phe Asn Thr Tyr Ala Met Asn
1               5                   10

<210> SEQ ID NO 10
<211> LENGTH: 57
<212> TYPE: DNA
<213> ORGANISM: Mus musculus

<400> SEQUENCE: 10
cgcataagaa gtaaatataa taattatgta acatattatg gcgattcagt gaaagac    57

<210> SEQ ID NO 11
<211> LENGTH: 19
<212> TYPE: PRT
<213> ORGANISM: Mus musculus

<400> SEQUENCE: 11

Arg Ile Arg Ser Lys Tyr Asn Asn Tyr Val Thr Tyr Tyr Gly Asp Ser
1               5                   10                  15

Val Lys Asp

<210> SEQ ID NO 12
<211> LENGTH: 30

```
<212> TYPE: DNA
<213> ORGANISM: Mus musculus

<400> SEQUENCE: 12
caaggtaggg gatcctatgc tatggactac                                     30

<210> SEQ ID NO 13
<211> LENGTH: 10
<212> TYPE: PRT
<213> ORGANISM: Mus musculus

<400> SEQUENCE: 13

Gln Gly Arg Gly Ser Tyr Ala Met Asp Tyr
1               5                   10

<210> SEQ ID NO 14
<211> LENGTH: 33
<212> TYPE: DNA
<213> ORGANISM: Mus musculus

<400> SEQUENCE: 14
aaggccagtg agaatgtggg tacttatgta tcc                                 33

<210> SEQ ID NO 15
<211> LENGTH: 11
<212> TYPE: PRT
<213> ORGANISM: Mus musculus

<400> SEQUENCE: 15

Lys Ala Ser Glu Asn Val Gly Thr Tyr Val Ser
1               5                   10

<210> SEQ ID NO 16
<211> LENGTH: 21
<212> TYPE: DNA
<213> ORGANISM: Mus musculus

<400> SEQUENCE: 16
ggggcatcca ataggtacac t                                              21

<210> SEQ ID NO 17
<211> LENGTH: 7
<212> TYPE: PRT
<213> ORGANISM: Mus musculus

<400> SEQUENCE: 17

Gly Ala Ser Asn Arg Tyr Thr
1               5

<210> SEQ ID NO 18
<211> LENGTH: 24
<212> TYPE: DNA
<213> ORGANISM: Mus musculus

<400> SEQUENCE: 18
ggacagagtt acagctatcc cacg                                           24

<210> SEQ ID NO 19
<211> LENGTH: 8
<212> TYPE: PRT
<213> ORGANISM: Mus musculus
```

```
<400> SEQUENCE: 19

Gly Gln Ser Tyr Ser Tyr Pro Thr
1               5
```

MONOCLONAL ANTIBODIES THAT INHIBIT THE WNT SIGNALING PATHWAY AND METHODS OF PRODUCTION AND USE THEREOF

CROSS REFERENCE TO RELATED APPLICATIONS/INCORPORATION BY REFERENCE STATEMENT

The present application is a continuation of U.S. Ser. No. 14/299,570, filed Jun. 9, 2014; which is a divisional of U.S. Ser. No. 13/031,010, filed Feb. 18, 2011, now U.S. Pat. No. 8,859,736, issued Oct. 14, 2014; which claims benefit under 35 U.S.C. 119(e) of U.S. provisional application Ser. No. 61/306,083, filed Feb. 19, 2010. The entire contents of each of the above-referenced patent applications are hereby expressly incorporated herein by reference.

STATEMENT REGARDING FEDERALLY FUNDED RESEARCH OR DEVELOPMENT

This invention was made with government support under Contract Number EY019309 awarded by the National Institutes of Health. The government has certain rights in the invention.

BACKGROUND

Abnormal or aberrant neovascularization is associated with a number of diseases and disorders, including but not limited to, cancer, inflammatory disease, macular degeneration and diabetic retinopathy (DR).

The Wnt signaling pathway plays a crucial role in neovascularization and many other associated biological processes, including retinal vessel development and the inflammation process. Mutation of Wnt signaling pathway genes Frizzled-4 (Fz4) or LRP5 leads to inhibition of retinal angiogenesis in familial exudative vitreoretinopathy (FEVR) patients, while Fz4 knockout mice exhibit incomplete retinal vascularization. Moreover, VEGF is upregulated as a result of mutational activation of Wnt signaling in colon cancer and human endothelial cells. VEGF is a potent mediator of vascular permeability and angiogenesis, and is an established therapeutic target for a number of angiogenesis associated diseases, including cancer and age related macular degeneration. A number of other angiogenic regulators are also Wnt target genes including, but not limited to, FGF18, endothelin-1, Cx43, uPAR, MMP7, and MMP3.

Among the aberrant neovascularization associated diseases, diabetic retinopathy (DR) is a very common complication of diabetes mellitus and one of the four common sight-threatening conditions in developed countries. Almost 100% of patients with type I diabetes and 60% of type II diabetic patients will develop some degrees of retinopathy in their lifetime. Approximately 10% of diabetic patients develop a severe visual handicap after 15 years of diabetes. DR is a chronic and progressive disorder, primarily affecting retinal capillaries. Breakdown of the blood-retinal barrier is a common pathological change in patients with diabetes and in streptozotocin (STZ)-induced diabetic animal models. In the early stages of DR, the retinal vascular permeability is increased without the appearance of clinical retinopathy. Retinal vascular leakage and thickening of the retina lead to diabetic macular edema (DME). In the late stages of DR, over-proliferation of capillary endothelial cells results in retinal neovascularization (NV), the abnormal formation of new vessels from preexisting capillaries in the retina and vitreous. This, in turn, leads to proliferative diabetic retinopathy (PDR). The abnormal angiogenesis can ultimately cause severe vitreous cavity bleeding and/or retinal detachment, resulting in severe vision loss.

It has been shown that multiple growth factors in the eye, such as but not limited to, VEGF, bFGF, IGF-1, and PEDF, are implicated in the pathogenesis of DR. Alterations of these growth factors and their receptors in diabetes have been identified in both experimental and clinical studies. Increased VEGF levels are at least partly responsible for retinal vascular leakage, retinal vascular hyper-permeability and retinal NV in patients with DR. VEGF therefore plays an important role in the development and pathogenesis of DR. The upregulated expression of retinal VEGF and its receptors correlates with retinal NV in OIR. Inhibition of VEGF and VEGF receptors has been shown to prevent retinal NV in diabetic and OIR animal models.

Accumulating evidence indicates that the Wnt signaling pathway not only mediates inflammation, i.e., TNF-alpha, NF-κB translocation and VEGF, but also regulates angiogenesis in the eye. Studies demonstrated that both Frizzled-4 (Fz4) and Lrp5/6 are expressed in adult murine retinal vasculature. Mutations in the Fz4 or LRP5 gene in the human lead to inhibition of normal retinal angiogenesis in familial exudative vitreoretinopathy (FEVR) patients, and Fz4 knockout (fz4$^{-/-}$) mice exhibited an incomplete retinal vascularization. Meanwhile, it has been shown that seven β-catenin/TCF binding sites occur in the gene promoter for VEGF-A. Under hypoxia conditions, HIF-1α competes with TCF-4 to form a new complex with β-catenin instead of β-catenin/TCF in the HIF-1α gene promoter region. Moreover, VEGF is upregulated as a result of mutational activation of the Wnt/β-catenin signaling in colon cancer cells and in human endothelial cells. A variety of other angiogenic regulators have previously been reported as Wnt target genes including but not limited to, FGF18, endothelin-1, Cx43, uPAR, MMP7, and MMP3. Thus Wnts may regulate angiogenesis through induction of multiple angiogenic genes.

The canonical pathway is initiated when a Wnt ligand binds to a member of the Frizzled serpentine receptor family and its co-receptor LRP6 or a close relative such as LRP5. When the Wnt-induced Fz-LRP6 complex forms, LRP6 will be phosphorylated at its PPPSP motif and is then capable of binding Axin in a phosphorylation-dependent manner to the plasma membrane, thereby resulting in the inhibition of β-catenin phosphorylation and degradation. LRP6 is of critical importance in human diseases. The LRP6 cytoplasmic domain is essential for Axin binding, and its deletion in LRP6 ΔC results in a dominant negative receptor that binds Wnt but is unable to bind Axin. The LRP6 extracellular domain has auto-inhibitory activity, because its deletion in LRP6ΔN results in a constitutively activated receptor that binds Axin in the absence of Wnt ligand.

As stated herein above, retinal NV is a major pathological feature leading to vision loss in DR. VEGF is a well-known key factor in stimulating the retinal NV formation in the DR.

Therefore, there exists a great need for new and improved compositions and methods for the inhibition of the Wnt signaling pathway. Such compositions and methods would be useful in the treatment and prevention of neovascularization-associated and/or Wnt signaling pathway associated diseases, including but not limited to, inflammation, fibrosis, angiogenesis and/or tumorigenesis. The presently disclosed inventive concept(s) is directed to said compositions and methods, which overcome the disadvantages and defects of the prior art.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 5 illustrates that DKK1 ameliorates retinal inflammation, vascular leakage, and NV, and inhibits ROS generation. A: Various doses of purified DKK1 were injected into the vitreous of the right eye of STZ-diabetic rats at 16 weeks following the onset of diabetes, and the same amounts of BSA were injected into the contralateral eyes for controls. Soluble ICAM-1 concentrations in the retina were measured by enzyme-linked immunosorbent assay, normalized by total protein concentrations, and expressed as ng per mg of proteins (means±SD, n=3). B: Purified DKK1 was injected into the vitreous of the right eye (1.2 μg/eye) of STZ-diabetic rats at 16 weeks following the onset of diabetes, and the same amounts of BSA were injected into the contralateral eyes for controls. Retinal vascular leakage was measured 48 hours after the injection by using Evans blue as a tracer, normalized by total protein concentrations, and expressed as μg of Evans blue per mg of retinal proteins (means±SD, n=4). C and D: At the age of P14, the OIR rats received an intravitreal injection of DKK1 (1 μg/eye) into the right eye and the same amount of BSA into the contralateral eyes. The retinas were harvested at P16, and the same amount of retinal proteins (20 μg) was loaded for Western blot analysis by using antibodies specific for COX2 (C) and VEGF (D), and normalized by β-actin levels. E: OIR rats at P14 received an intravitreal injection of DKK1 at doses as indicated. Retinal vascular leakage was measured at P16 by using Evans blue as a tracer, normalized by total protein concentrations, and expressed as μg of Evans blue per mg of retinal proteins (means±SD, n=3). *P<0.05. F-J: OIR rats received an intravitreal injection of 2 μg/eye DKK1, and BSA into the contralateral eyes at age of P14. At P18, retinal vasculature was visualized by fluorescein angiography on the whole-mounted retina from the eyes injected with BSA (F and G) and injected with DKK1 (H and I). Original magnification: ×12.5 (F and H); ×100 (G and I). J: Preretinal vascular cells were counted on cross ocular sections from the eyes injected with BSA and DKK1 (means±SD, n=5).

FIG. 6 illustrates that the Wnt pathway contributes to the oxidative stress and HIF-1 activation. A-D: DKK1 inhibits HIF-α activation: Primary RCEC were exposed to 5 mmol/L glucose and 25 mmol/L mannitol (A), 30 mmol/L glucose (B), TNF-α (C), and 30 mmol/L glucose with 1 μg/ml DKK1 (D) for 4 hours. HIF-1α nuclear translocation was determined by using immunocytochemistry with an anti-HIF-1α antibody. Scale bar=50 μm. E: RCEC were exposed to low glucose (5 mmol/L glucose plus 25 mmol/L mannitol) or high glucose (30 mmol/L glucose), or 1 μg/ml TNF-α in the absence or presence of various concentrations of DKK1 (6.25 to 100 nmol/L). Aminoguanidine (AG; 10 μmol/L) was used as a positive control. Intracellular ROS generation was measured and expressed as fluorescent unit per well (means±SD, n=3).

(D) and primary BRCEC (E) were exposed to HG for 6 hours after 1 hour pre-incubation with Anti-LRP6-1. Cytosolic fraction (20 µg) was subjected to Western blot analysis for cytosolic β-catenin and phospho-β-catenin (Ser33/37/Thr41).

Figure 18:
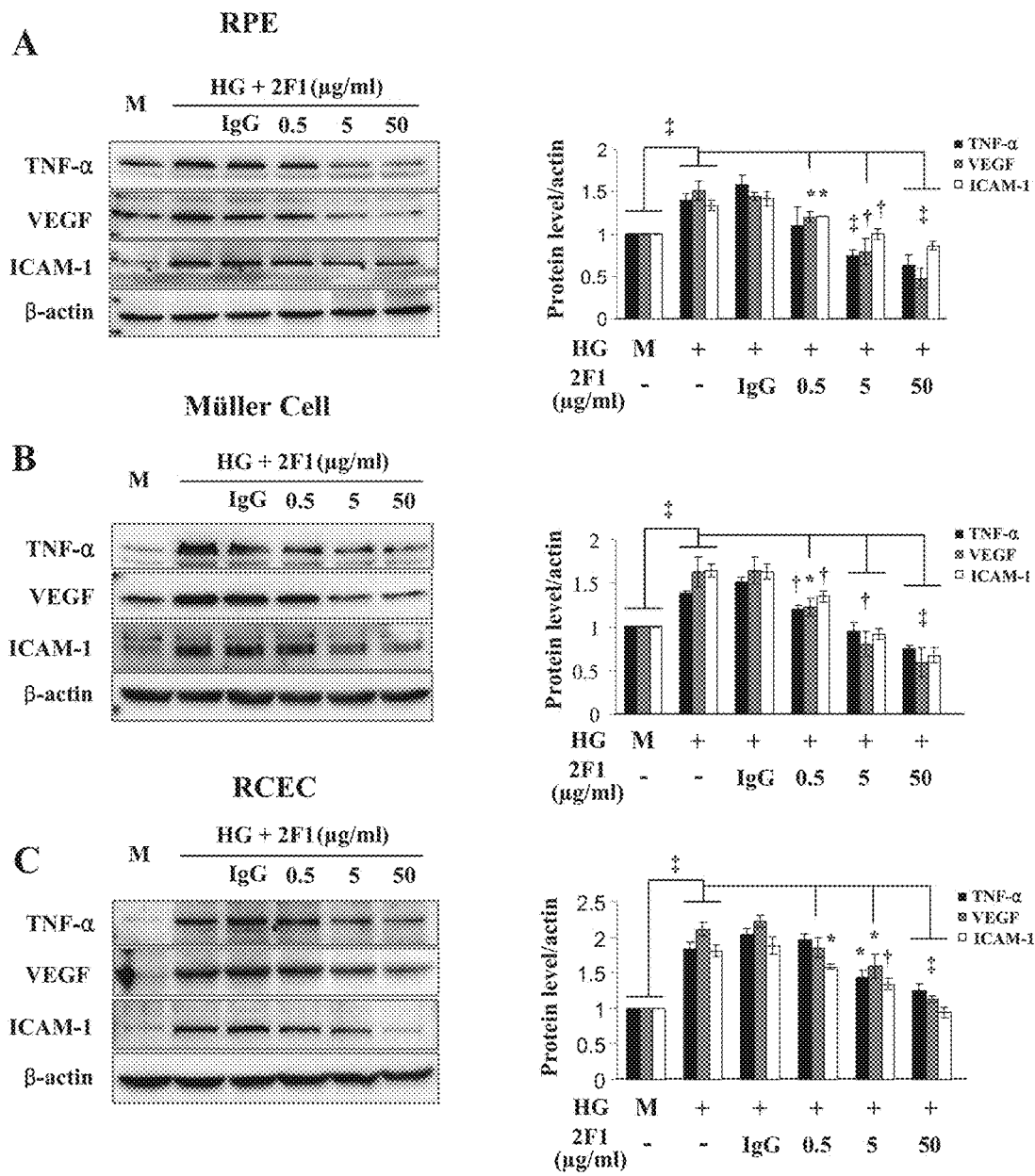

FIG. 18 illustrates the inhibitory effect of Anti-LRP6-1 on high glucose-induced over-expression of angiogenic and inflammatory factors. hTERT-RPEs (A), rMC-1 (B), and BRCEC (C) were exposed to 30 mmol/L D-glucose (HG), with 5 mM glucose and 25 mM mannitole (M) as control, for 24 hours (A & C) or 48 hours (B) following 1 hour pre-incubation of the Anti-LRP6-1. Western blot analysis was performed using specific antibodies for ICAM-1, TNF-α and VEGF. Representative blots from at least three independent experiments are shown. Levels were quantified by densitometry and normalized by β-actin levels (mean±SD, n=3, *P<0.05, †P<0.001, ‡P<0.0001).

Figure 19:
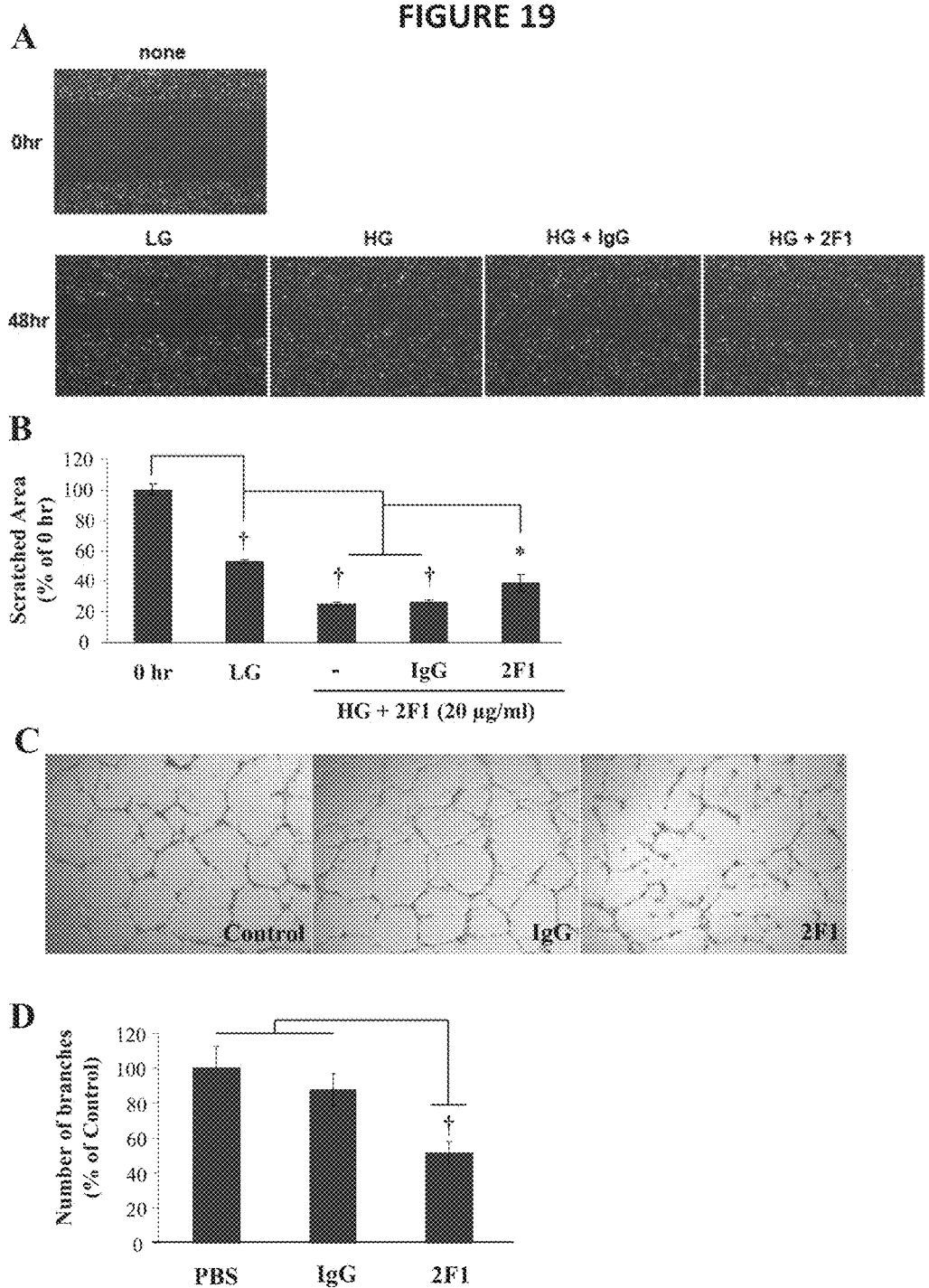

FIG. 19 illustrates the inhibitory effect of Anti-LRP6-1 on migration of endothelial cells. A: Endothelial migration in the scratch wound model. BRCEC plated on the gelatin-coated plates were scratched and exposed to high glucose for 48 hours with 20 µg/ml Anti-LRP6-1 or non-specific IgG. Representative images of the scratch area are shown. B: Pictures of three different areas of each plate were taken and the surface area without migrated cells was measured using Image J (NIH) for the quantification. High glucose increased migration rate of BRCEC. Anti-LRP6-1 significantly suppressed migration of the BRCEC compared to non-specific IgG (mean±SD, n=3, †P<0.001, *P<0.05). C: Tube formation: Matrigel was thawed on ice and spread evenly into a 24 well plate, followed by 30 minutes incubation at 37° C. BRCEC ($2.5 \times 10^4$) were seeded into each well and supplemented with PBS and 20 µg/ml non-specific IgG as negative controls and 20 µg/ml of Anti-LRP6-1. BRCEC were grown to form a tube for 12 hours and five fields from each well were photographed. D: Quantification of the tube formation was performed by counting the number of the branches in the fields. Anti-LRP6-1 significantly suppressed tube formation of BRCEC compared to non-specific IgG (mean±SD, n=3, †P<0.001).

Figure 20:
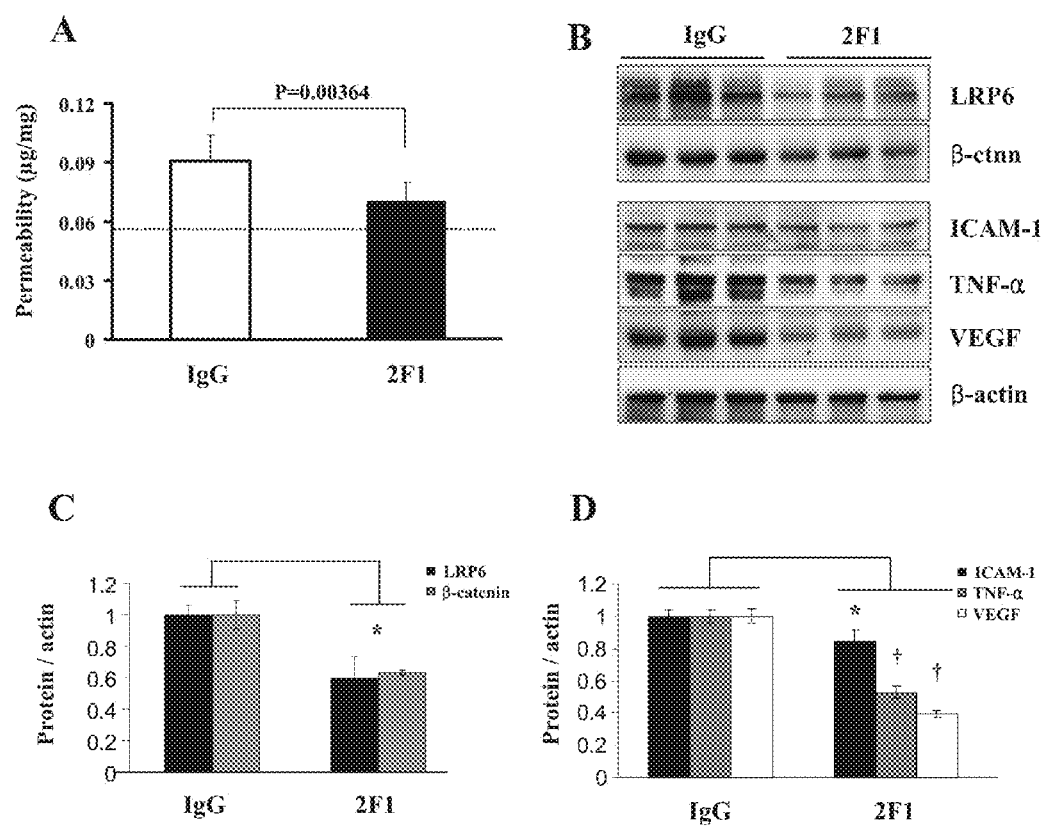

FIG. 20 illustrates the inhibitory effect of Anti-LRP6-1 on the vascular leakage and inflammation in the OIR model. A: OIR rats received an intravitreal injection of 10 µg Anti-LRP6-1 per eye, and the same amount of non-specific IgG to the contralateral eyes at age of P12. Retinal vascular permeability was measured at P16 using Evans blue as a tracer, normalized by total retinal protein concentrations, and expressed as µg of Evans blue per mg of retinal proteins (means±SD, n=8, P<0.001). Dotted line indicates the basal level of vascular permeability in age-matched normal animals. B-D: The retinas were harvested at P16, and the same amount of retinal proteins (50 µg) was loaded for Western blot analysis using antibodies specific for LRP6, β-catenin, ICAM-1, VEGF and TNF-α (FIG. 20B), and normalized by β-actin levels (means±SD, n=3, *P<0.05, †P<0.001; FIG. 20C-D).

Figure 21:
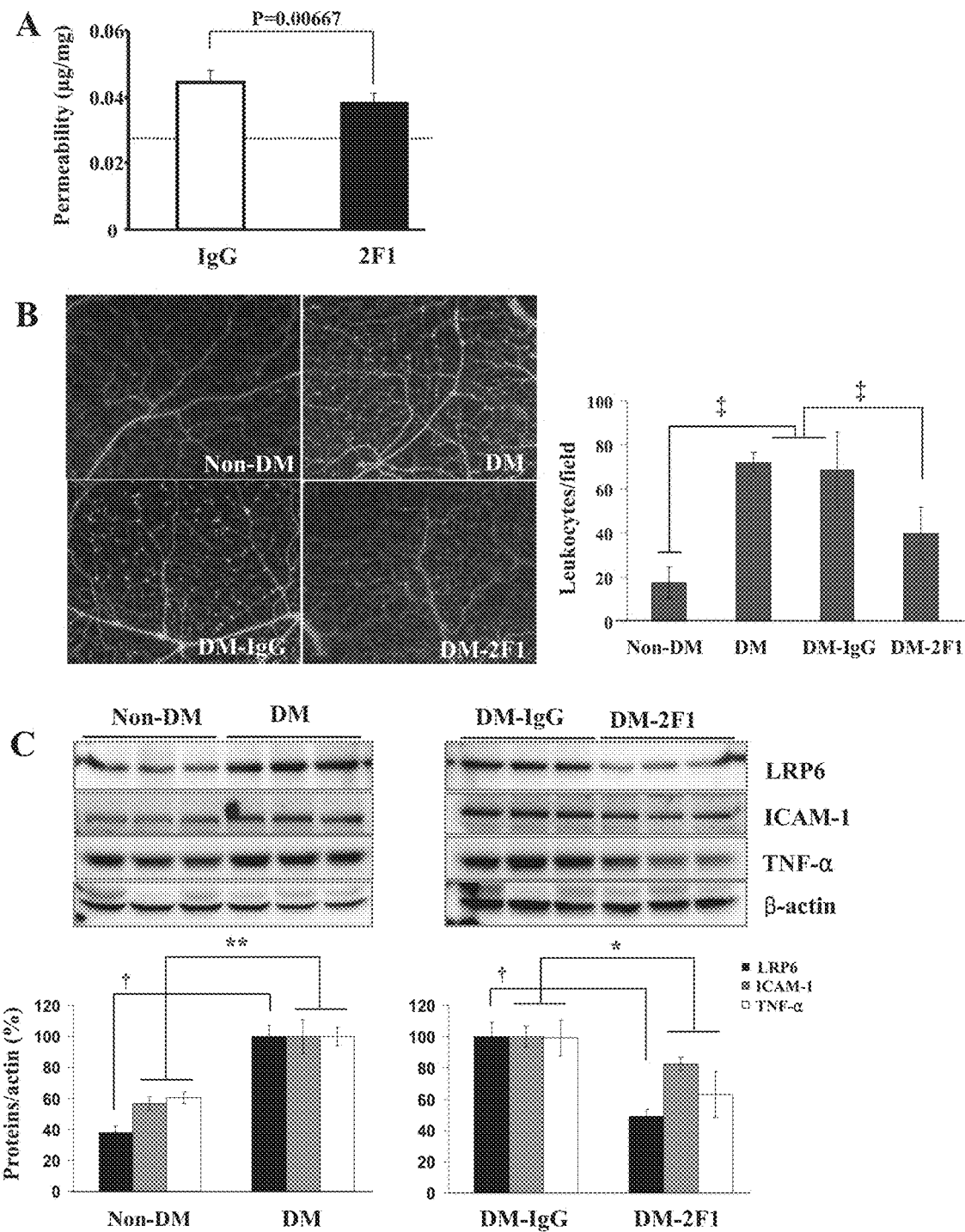

FIG. 21 illustrates the inhibitory effect of Anti-LRP6-1 on retinal vascular leakage and inflammation in the STZ-induced diabetic rats. STZ-induced diabetic rats at 2 weeks post-onset of diabetes received an intravitreal injection of Anti-LRP6-1 (20 µg) or the same amount of non-specific IgG as control. A: retinal vascular permeability was measured at 1 week post-injection of the antibody using Evans blue as a tracer, and normalized by total retinal protein concentrations (means±SD, n=6, P=0.00667). B: Adherent leukocytes were stained with FITC-concanavalin-A in non-diabetic rats, diabetic rats treated with IgG or Anti-LRP6-1 after the circulating leukocytes were removed by thorough perfusion. The retinas were then flat-mounted, and the adherent leukocytes were visualized under fluorescence microscope. Representative images are shown in (B). Multiple leukocytes adherent to retinal vasculature were observed in the diabetic rat retinas and those with IgG injection, but fewer in the Anti-LRP6-1 treated diabetic rats. Adherent leukocytes were counted in 4 random fields of each retina (mean±SD, n=5, ‡P<0.0001). C: Two weeks after the intravitreal injection, the retinas were dissected from non-diabetic (non-DM), diabetic (DM), and diabetic rats treated with IgG (DM-IgG) or Anti-LRP6-1 (DM-2F1) groups. The same amount of retinal proteins was loaded for Western blot analysis to measure expression levels of LRP6, ICAM-1 and TNF-α (mean±SD, n=3, *P<0.05, **P<0.01, †P<0.001).

Figure 22:
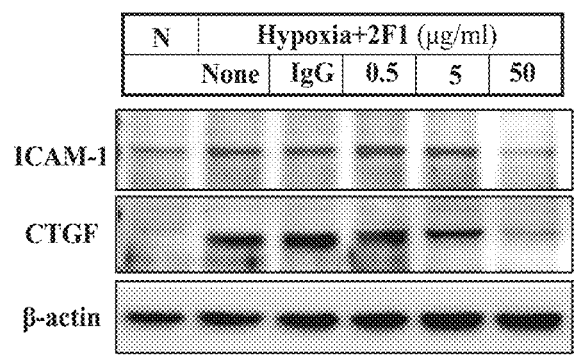

FIG. 22 illustrates inhibition of ICAM1 and CTGF expression by Anti-LRP6-1 under hypoxia. ARPE19 cells were exposed to 200 µM $CoCl_2$ in the presence of various concentrations of Anti-LRP6-1 for 24 hours. Non-specific IgG (50 µg/ml) was used as control. Equal amount of the total cell lysates were loaded for Western blot analysis to measure the expression level of ICAM-1 and CTGF and normalized by β-actin levels.

Figure 23:
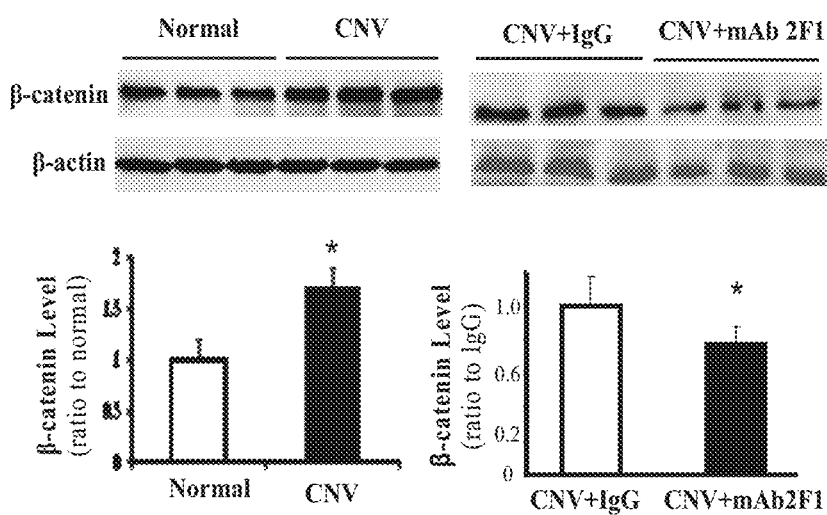

FIG. 23 illustrates that Anti-LRP6-1 decreases β-catenin levels in the eyecup with laser-induced CNV. Rats received laser photocoagulation followed by intravitreal injection of 20 µg/eye Anti-LRP6-1 or non-specific rat IgG. At day 7 after the injection, the retina-choroid complex was dissected and β-catenin levels measured by Western blot analysis. The same amount of proteins from normal eyes and that with CNV but without the injection was blotted for comparison. The total β-catenin levels were quantified by densitometry and normalized to β-actin levels (mean±SD, n=6). CNV showed up-regulated β-catenin levels which were decreased by Anti-LRP6-1 in the CNV model. Each lane represents an individual rat. *P<0.05.

Figure 24:
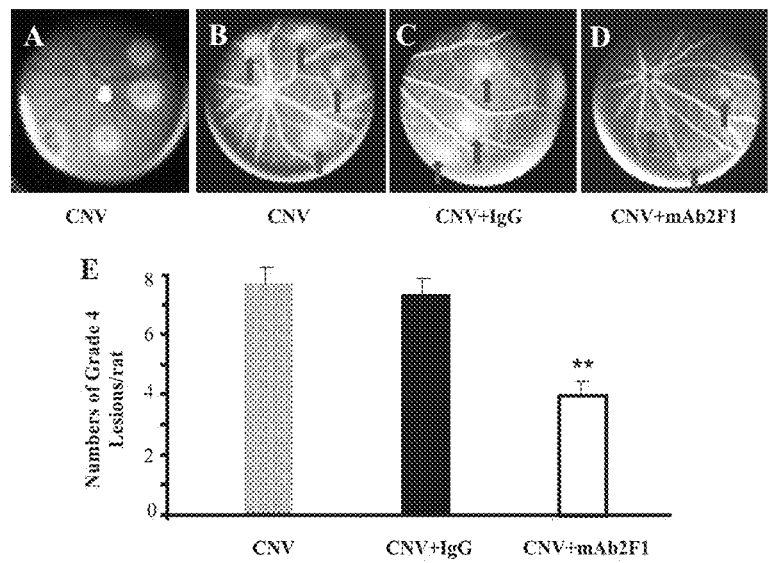

FIG. 24 illustrates that Anti-LRP6-1 decreases numbers of Grade 4 lesions in laser-induced CNV. Fluorescein angiography was performed 14 days after the laser photocoagulation. Fundus images were captured. (A) The fundus image without fluorescein angiography; (B-D) representative fundus images with fluorescein angiography. (E) Grade 4 lesions were counted and compared (mean±SD, n=10) *P<0.01.

Figure 25:
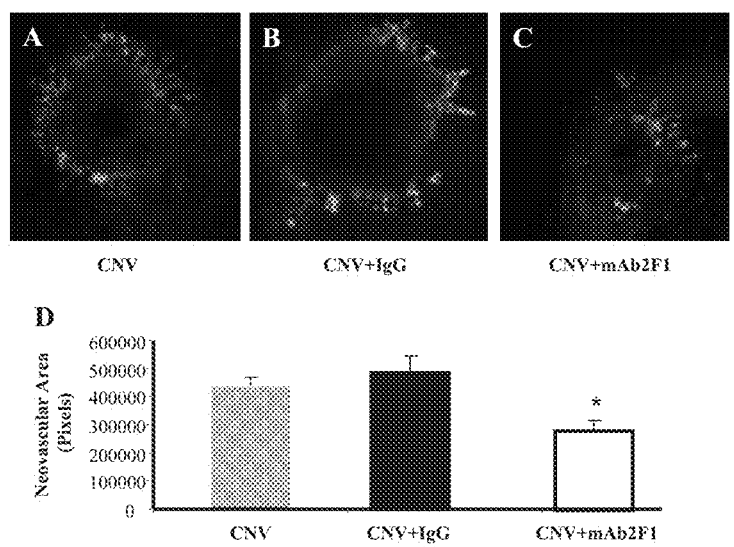

FIG. 25 illustrates that Anti-LRP6-1 decreases CNV area. CNV was induced by laser photocoagulation in rats. Anti-LRP6-1 (20 µg/eye) was injected into the vitreous with the same amount rat IgG as control at the same day of the laser. Two weeks post-injection, CNV was visualized with fluorescein angiography. (A-C) Representative micrographs of CNV lesions in an RPE-choroidal flat-mount in the CNV without treatment (A), with control IgG (B) and with Anti-LRP6-1 (C). (D) The CNV areas were measured and compared (mean±SD, n=20). *P<0.05.

DETAILED DESCRIPTION OF THE INVENTIVE CONCEPT(S)

Before explaining at least one embodiment of the presently disclosed inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications and patent applications mentioned in the specification are indicative of the level of skill of those skilled in the art to which the presently disclosed inventive concept(s) pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of the presently disclosed inventive concept(s) have been described in terms of particular embodiments, it will be apparent to those of skill in the art that variations may be applied to the compositions and/or methods and in the steps or in the sequence of steps of the method described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The terms "peptide," "polypeptide," and "protein" are used herein to refer to a polymer of amino acid residues. The term "polypeptide" as used herein is a generic term to refer to native protein, protein fragments, or analogs of a polypeptide sequence. Hence, native protein, protein fragments, and analogs are species of the polypeptide genus. The term "isolated peptide/polypeptide/protein" as used herein refers to a peptide/polypeptide/protein of cDNA, recombinant RNA, or synthetic origin or some combination thereof, which by virtue of its origin, or source of derivation, the "isolated peptide/polypeptide/protein": (1) is not associated with peptides/polypeptides/proteins found in nature, (2) is free of other peptides/polypeptides/proteins from the same source, e.g., free of murine proteins, (3) is expressed by a cell from a different species, and/or (4) does not occur in nature.

As used herein, the term "amino acid" embraces all molecules, whether natural or synthetic, which include both an amino functionality and an acid functionality and capable of being included in a polymer of naturally-occurring amino acids. Exemplary amino acids include naturally-occurring amino acids; analogs, derivatives, and congeners thereof;

amino acid analogs having variant side chains; and all stereoisomers of any of any of the foregoing.

The terms "polynucleotide," and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors").

The term "naturally-occurring" as used herein as applied to an object refers to the fact that an object can be found in nature. For example, a polynucleotide or polypeptide sequence that is present in an organism (including viruses) that can be isolated from a source in nature and which has not been intentionally modified by man in the laboratory or otherwise is naturally-occurring. The term "naturally-occurring" may be used interchangeably herein with the term "native."

The term "selectively hybridize" referred to herein means to detectably and specifically bind. Polynucleotides, oligonucleotides and fragments thereof encoding peptides/polypeptides/proteins in accordance with the inventive concept(s) selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the inventive concept(s) and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The following terms are used to describe the sequence relationships between two or more polynucleotide or amino acid sequences: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Adv. Appl. Math., 2:482 (1981)), by the homology alignment algorithm of Needleman and Wunsch (J. Mol. Biol., 48:443 (1970)), by the search for similarity method of Pearson and Lipman (Proc. Natl. Acad. Sci. (U.S.A.), 85:2444 (1988)), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages, or by inspection, and the best alignment (i.e., resulting in the highest percentage of homology over the comparison window) generated by the various methods is selected.

The term "sequence identity" means that two polynucleotide or amino acid sequences is identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the presently disclosed inventive concept(s). Examples of unconventional amino acids include: 4-hydroxyproline, α-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, such as at least 90 percent sequence identity, or at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "variant" of a reference polypeptide refers to a polypeptide having one or more amino acid substitutions, deletions or insertions relative to the reference polypeptide. An amino acid substitution may be "conservative" or "non-conservative." A "conservative" amino acid substitution refers to the substitution of an amino acid in a polypeptide with another amino acid having similar properties, such as but not limited to, size and charge. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., Science, 253:164 (1991)). Thus, the foregoing examples demonstrate that those of skill in the art can recognize sequence motifs and structural conformations that may be used to define structural and functional domains in accordance with the presently disclosed inventive concept(s).

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure© (Branden and J. Tooze, eds., Garland Publishing, New York, N.Y. (1991)); and Thornton et al. (Nature 354:105 (1991)), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence. A polypeptide fragment may be any length that is less than the length of the reference polypeptide.

The term "antibody" is used in the broadest sense, and specifically covers monoclonal antibodies (including full length monoclonal antibodies), polyclonal antibodies, multispecific antibodies (e.g., bispecific antibodies), and antibody fragments so long as they exhibit the desired biological activity. Thus, the terms "Antibody" or "antibody peptide(s)" refer to a full length immunoglobulin molecule (i.e., an intact antibody), or a binding fragment thereof that competes with the intact antibody for specific antigen binding. Binding fragments may be produced by recombinant DNA techniques, or by enzymatic or chemical cleavage of intact antibodies. Binding fragments include Fab, Fab', F(ab')$_2$, Fv, scFv, disulfide linked Fv, Fd, diabodies, single-chain antibodies, single domain antibodies (such as but not limited to, NANOBODIES®) and other antibody fragments that retain at least a portion of the variable region of an intact antibody. See, e.g., Hudson et al. (Nature Med., 9:129-134 (2003)).

The term "antigen binding fragment" or "antigen-binding portion" of an antibody, as used herein, refers to one or more fragments of an antibody that retain the ability to bind to an antigen. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES®), isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

The terms "CDR," and its plural "CDRs," refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

The term "epitope" includes any protein determinant capable of specific binding to an immunoglobulin or T-cell receptor. In certain embodiments, an epitope is a region of an antigen that is specifically bound by an antibody. Epitopic determinants usually include chemically active surface groupings of molecules such as amino acids, sugar side chains, phosphoryl, or sulfonyl groups. In certain embodiments, an epitope may have specific three dimensional structural characteristics (e.g., a "conformational epitope"), as well as specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope or closely related epitopes. In certain instances, for example, homologous proteins from different species may comprise the same epitope. In certain embodiments, an antibody specifically binds to an antigen with a dissociation constant of no greater than $10^{-6}$ M, $10^{-7}$ M, $10^{-8}$ M or $10^{-9}$ M. When an antibody specifically binds to a receptor or ligand (i.e., counterreceptor), it may substantially inhibit adhesion of the receptor to the ligand. As used herein, an antibody substantially inhibits adhesion of a receptor to a ligand when an excess of antibody reduces the quantity of receptor bound to ligand by at least about 20%, 40%, 60% or 80%, 85%, or 90% (as measured in an in vitro competitive binding assay).

An "isolated" antibody is one which has been separated and/or recovered from a component of the environment in which it was produced. Contaminant components of its production environment are materials which would interfere with diagnostic or therapeutic uses for the antibody, and may include enzymes, hormones, and other proteinaceous or nonproteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spinning cup sequentator, such as at least 15 residues of sequence; or 3) to homogeneity by SDS-PAGE under reducing or non-reducing conditions using Coomasie blue or, preferably, silver stain. Isolated antibody includes the antibody in situ within recombinant cells since at least one component of the environment in which the antibody is produced will not be present. Ordinarily, however, isolated antibody will be prepared by at least one purification step. In addition, the "isolated antibody" is substantially free of other antibodies having different antigenic specificities. An isolated antibody may, however, have some cross-reactivity to other, related antigens.

The term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95%.

The term "monoclonal antibody" as used herein refers to an antibody obtained from a population of substantially homogeneous antibodies that specifically bind to the same epitope, i.e., the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that in one method of production they may be synthesized by a hybridoma culture, and thus are uncontaminated by other immunoglobulins. The modifier "monoclonal" indicates the character of the antibody as being obtained from a substantially homogeneous population of antibodies, and is not to be construed as requiring production of the antibody by any particular method. For example, in one embodiment, the monoclonal antibodies produced in accordance with the presently disclosed inventive concept(s) may be made by the hybridoma method first described by Kohler and Milstein (Nature, 256:495 (1975)).

The monoclonal antibodies utilized in accordance with the presently disclosed inventive concept(s) may be produced by any methodology known in the art including, but not limited to, a result of a deliberate immunization protocol; a result of an immune response that results in the production of antibodies naturally in the course of a disease or cancer; phage-derived antibodies; and the like. In addition to the hybridoma production method listed above, the monoclonal antibodies of the presently disclosed inventive concept(s) may be produced by other various methods such as, but not limited to, recombinant DNA methods (see, e.g., U.S. Pat. No. 4,816,567); isolation of antibody fragments from a phage display library (see, e.g., Clackson et al., Nature, 352:624-628 (1991); and Marks et al., J. Mol. Biol., 222:581-597 (1991)); as well as various other monoclonal antibody production techniques (see, e.g., Harlow and Lane (1988) Antibodies: A Laboratory Manual (Cold Spring Harbor Laboratory, Cold Spring Harbor, N.Y.)).

Once the antibodies have been obtained, for example, once individual B cells have been identified and/or monoclonal antibodies have been produced, the sequences encoding the variable regions of these antibodies can be obtained. The variable region sequences can, for example, be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by, for example, the methods described in Babcook et al. (Proc. Natl. Acad. Sci. USA, 93:7843-7848 (1996)), and in PCT Publication No. WO 92/02551. The contents of both references are expressly incorporated herein by reference in their entirety.

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from one animal fused to a portion of an antibody from a second animal. For example but not by way of limitation, a chimeric antibody may comprise all or portion of a variable region of an antibody derived from a non-human animal fused to a constant region of an antibody derived from a human.

Utilization of the monoclonal antibodies of the presently disclosed inventive concept(s) may require administration thereof to a subject, such as but not limited to, a human. However, when the monoclonal antibodies are produced in a non-human animal, such as a rodent, administration of such antibodies to a human patient will normally elicit an immune response, wherein the immune response is directed towards the sequence of the antibodies. Such reactions limit the duration and effectiveness of such a therapy. In order to overcome such problem, the monoclonal antibodies of the presently disclosed inventive concept(s) are "humanized," that is, the antibodies are engineered such that one or more antigenic portions thereof are removed and like portions of a human antibody are substituted therefore, while the antibodies' affinity for the desired epitope is retained. This engineering may only involve a few amino acids, or may include entire framework regions of the antibody, leaving only the complementarity determining regions of the antibody intact. Several methods of humanizing antibodies are known in the art and are disclosed in U.S. Pat. No. 6,180,370, issued to Queen et al. on Jan. 30, 2001; U.S. Pat. No. 6,054,927, issued to Brickell on Apr. 25, 2000; U.S. Pat. No. 5,869,619, issued to Studnicka on Feb. 9, 1999; U.S. Pat. No. 5,861,155, issued to Lin on Jan. 19, 1999; U.S. Pat. No. 5,712,120, issued to Rodriquez et al. on Jan. 27, 1998; and U.S. Pat. No. 4,816,567, issued to Cabilly et al. on Mar. 28, 1989, the Specifications of which are all hereby expressly incorporated herein by reference in their entirety.

As mentioned above, a "humanized" antibody refers to a non-human antibody that has been modified so that it more closely matches (in amino acid sequence) a human antibody. A humanized antibody is thus a type of chimeric antibody. As described above, antibodies interact with target antigens predominantly through amino acid residues that are located in the heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific, naturally occurring antibodies by constructing expression vectors in which the CDR sequences from the naturally occurring antibody are grafted into framework sequences from a different antibody with different properties, such as human antibody framework regions. Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference.

Humanized forms of antibodies are chimeric immunoglobulins, immunoglobulin chains or fragments thereof (such as Fv, Fab, Fab', F(ab')$_2$, or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., 1986; Riechmann et al., 1988; Verhoeyen et al., 1988), by substituting rodent CDRs or CDR sequences for the corresponding sequences of a human antibody. (See also U.S. Pat. No. 5,225,539.) In some instances, $F_v$ framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, 1992).

The prior art is filled with published articles relating to the generation or use of humanized antibodies. Many of these studies teach useful examples of protocols that can be utilized with the presently disclosed inventive concept(s), such as but not limited to, Sandborn et al., Gatroenterology, 120:1330 (2001); Mihara et al., Clin. Immunol., 98:319 (2001); Yenari et al., Neurol. Res., 23:72 (2001); Morales et al., Nucl. Med. Biol., 27:199 (2000); Richards et al., Cancer Res., 59:2096 (1999); Yenari et al., Exp. Neurol., 153:223 (1998); and Shinkura et al., Anticancer Res., 18:1217 (1998), all of which are expressly incorporated in their entirety by reference. However, it is to be understood that the presently disclosed inventive concept(s) is not limited to the treatment protocols described above, and other treatment protocols which are known to a person of ordinary skill in the art may be utilized in the methods of the presently disclosed inventive concept(s).

The presently disclosed inventive concept(s) further includes the use of fully human monoclonal antibodies. Fully human antibodies essentially relate to antibody molecules in which the entire sequence of both the light chain and the heavy chain, including the CDRs, arise from human genes. Such antibodies are termed "human antibodies" or "fully human antibodies" herein. "Human antibodies" contain human antibody sequences and do not contain antibody sequences from a non-human animal. In certain embodiments, a human antibody may further contain synthetic sequences not found in native antibodies. The term is not limited by the manner in which the antibodies are made.

Human monoclonal antibodies may be prepared by the trioma technique; the human B-cell hybridoma technique (see Kozbor et al., Hybridoma, 2:7 (1983)) and the EBV hybridoma technique to produce human monoclonal antibodies (see Cole et al., PNAS, 82:859 (1985)). Human monoclonal antibodies may be utilized in the practice of the presently disclosed inventive concept(s) and may be produced by using human hybridomas (see Cote et al. PNAS, 80:2026 (1983)) or by transforming human B-cells with Epstein Barr Virus in vitro (see Cole et al., 1985).

In addition, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example but not by way of limitation, in U.S. Pat. Nos. 5,545,807; 5,545,806; 5,569,825; 5,625,126; 5,633,425; 5,661,016, and in Marks et al., J Biol. Chem., 267:16007 (1992); Lonberg et al., Nature, 368:856 (1994); Morrison, 1994; Fishwild et al., Nature Biotechnol., 14:845 (1996); Neuberger, Nat. Biotechnol., 14:826 (1996); and Lonberg and Huszar, Int Rev Immunol., 13:65 (1995).

Human antibodies may additionally be produced using transgenic nonhuman animals which are modified so as to produce fully human antibodies rather than the animal's endogenous antibodies in response to challenge by an antigen. (See PCT Publication No. WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. One embodiment of such a nonhuman animal is a mouse, and is termed the XENO-MOUSE™ as disclosed in PCT Publication Nos. WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598, issued to Kucherlapati et al. on Aug. 17, 1999, and incorporated herein by reference. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771, issued to Hori et al. on Jun. 29, 1999, and incorporated herein by reference. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

As used herein, "substantially pure" means an object species is the predominant species present (i.e., on a molar basis it is more abundant than any other individual species in the composition). Generally, a substantially pure composition will comprise more than about 50% percent of all macromolecular species present in the composition, such as more than about 55%, 60%, 65%, 70%, 75%, 80%, 85%, 90%, 95%, and 99%. In one embodiment, the object species is purified to essential homogeneity (contaminant species cannot be detected in the composition by conventional detection methods) wherein the composition consists essentially of a single macromolecular species.

The term "agent" refers to a chemical compound, a mixture of chemical compounds, a biological macromolecule, or an extract made from biological materials. In certain embodiments, the "agent" may be a monoclonal antibody in accordance with the presently disclosed inventive concept(s).

The term "antagonist" refers to an agent that reduces an activity of a protein/enzyme.

The term "agonist" refers to an agent that increases an activity of a protein/enzyme.

The term "patient" includes human and veterinary subjects. In certain embodiments, a patient is a mammal. In certain other embodiments, the patient is a human.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

A "disorder" is any condition that would benefit from treatment with the polypeptide. This includes chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, and various types of head and neck cancer.

"Mammal" for purposes of treatment refers to any animal classified as a mammal, including human, domestic and farm animals, nonhuman primates, and zoo, sports, or pet animals, such as dogs, horses, cats, cows, etc.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed inventive concept(s). The therapeutic effect may include, for example but not by way of limitation, inhibiting and/or neutralizing at least one activity of LRP6. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease/disorder in conjunction with the compositions of the presently disclosed inventive concept(s). This concurrent therapy can be sequential therapy where the patient is treated first with one drug and then the other, or the two drugs are given simultaneously.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The compositions of the presently disclosed inventive concept(s) may be administered to a patient by any method known in the art, including but not limited to, oral, topical, transdermal, parenteral, subcutaneous, intranasal, intramuscular, intraperitoneal, intravitreal, and intravenous routes, including both local and systemic applications. In addition, the compounds of the presently disclosed inventive concept(s) may be designed to provide delayed, controlled or sustained release using formulation techniques which are well known in the art.

The term "Wnt" or the plural "Wnts" as used herein will be understood to refer to a group of secreted, cysteine-rich glycoproteins which bind to a co-receptor complex of frizzled (Fz) receptors and low-density lipoprotein receptor-related proteins 5 or 6 (LRP5/6) and regulate expression of a number of target genes through an intracellular signaling pathway, namely the Wnt pathway. In humans, the Wnts include WNT1, WNT2, WNT2B, WNT3, WNT3A, WNT4, WNT5A, WNT5B, WNT6, WNT7A, WNT7B, WNT8A, WNT8B, WNT9A, and WNT9B. In the absence of Wnt ligands, β-catenin, a down-stream effector of the canonical Wnt pathway, is phosphorylated by a protein complex containing glycogen synthase kinase-3β (GSK-3β). The phosphorylated β-catenin is constantly degraded, to prevent its accumulation. Upon binding of certain Wnts to the Fz-LRP5/6 co-receptors, phosphorylation of β-catenin is inhibited, which prevents the degradation of β-catenin and results in its accumulation. β-catenin is then translocated into the nucleus, where it associates with T cell factor for DNA binding and thus regulates expression of target genes including but not limited to VEGF.

The term "LRP" will be understood to refer to "low-density lipoprotein receptor-related proteins." Human LRP6 is represented by SEQ ID NO: 1. LRP5/6 is known to play a critical role in Wnt/β-catenin signaling. Upon binding with Wnt ligands, LRP6 dimerizes with Fz receptor, which is the first and essential step in activation of the Wnt pathway. The cytoplasmic domain of LRP6 has multiple modular phosphorylation sites, and phosphorylation of LRP6 is an essential event for activation of the canonical Wnt pathway, as the phosphorylation of LRP6 promotes the recruitment of the scaffold protein Axin, and thus activates the canonical Wnt pathway.

The monoclonal antibodies described herein are characterized, in part, by functional and/or structural features of the antibodies.

The presently disclosed inventive concept(s) is related to an isolated monoclonal antibody (or antigen binding fragment thereof) that specifically binds LRP6 protein, as well as compositions comprising same. In one embodiment, the monoclonal antibody specifically binds the human LRP6 protein; in a further embodiment, the monoclonal antibody specifically binds an epitope in the amino acid sequence of SEQ ID NO:1. In yet another embodiment, the monoclonal antibody specifically binds an extracellular domain of LRP6; in a yet further embodiment, the monoclonal antibody specifically binds an epitope in the amino acid sequence of SEQ ID NO:2. In another embodiment, the monoclonal antibody specifically binds a ligand-binding domain of LRP6. In yet another embodiment, the monoclonal antibody specifically binds an epitope in at least one of the first and second beta-propeller regions (E1E2 domains) of LRP6. In yet a further embodiment, the monoclonal antibody specifically binds an epitope in at least a portion of the E2 domain of LRP6; in yet another further embodiment, the monoclonal antibody specifically binds an epitope in the amino acid sequence of SEQ ID NO:3.

Standard assays to evaluate the binding ability of the antibodies are known in the art, including, for example, ELISAs, Western blots and RIAs and suitable assays are described in the Examples. The binding kinetics (e.g., binding affinity) of the antibodies also can be assessed by standard assays known in the art, such as by Biacore analysis. In some embodiments, the antibodies described herein bind to SEQ ID NO: 1, SEQ ID NO: 2 and/or SEQ ID NO: 3 with a dissociation constant of less than or equal to $10^{-6}$ M, $10^{-7}$ M, $10^{-8}$ M, or $10^{-9}$ M. In one embodiment, the antibody binds to the LRP6 extracellular domain with a dissociation constant of less than or equal to about $10^{-7}$ M.

The presently disclosed inventive concept(s) is also directed to the hybridoma HLS2F1, ATCC accession number PTA-10663, as well as compositions comprising same. Said hybridoma was deposited with the American Type Culture Collection Patent Depository (10801 University Boulevard, Manassas, Va. 20110-2209) on Feb. 18, 2010, under the terms of the Budapest Treaty. All restrictions on the availability to the public of the deposited material will be irrevocably removed upon the granting of a patent directed to said mAb, and the deposit will be maintained for 30 years or 5 years after the most recent request (whichever is later). The presently disclosed inventive concept(s) is also directed to an isolated monoclonal antibody produced by said hybridoma. The mAb produced by said deposited hybridoma is a murine IgG2 antibody and will herein after be referred to as Anti-LRP6-1. In addition, the presently disclosed inventive concept(s) is also directed to a cell of hybridoma HLS2F1, ATCC accession number PTA-10663, as well as compositions comprising same.

The presently disclosed inventive concept(s) is also directed to an isolated monoclonal antibody (or antigen binding fragment thereof) that binds to the same epitope as any of the monoclonal antibodies described herein above, as well as compositions comprising same. In one embodiment, the mAb binds to the same epitope as Anti-LRP6-1. In another embodiment, the mAb binds to the same epitope as the antibody produced by hybridoma HLS2F1, ATCC accession number PTA-10663. Such antibodies can be identified based on their ability to cross-compete with anti-LRP6-1 in standard LRP6 extracellular domain binding assays. The ability of a test antibody to inhibit the binding of anti-LRP6-1 to the LRP6 extracellular domain demonstrates that the test antibody can compete with anti-LRP6-1 for binding to the LRP6 extracellular domain and thus binds to the same epitope on the LRP6 extracellular domain as anti-LRP6-1.

The presently disclosed inventive concept(s) is also directed to an isolated monoclonal antibody that specifically binds to a sequence that is at least 80% identical to any of SEQ ID NOS:1-3, including a sequence that is at least 85% identical to any of SEQ ID NOS:1-3, a sequence that is at least 90% identical to any of SEQ ID NOS:1-3, and a sequence that is at least 95% identical to any of SEQ ID NOS:1-3, and compositions comprising said isolated monoclonal antibody. In addition, the presently disclosed inventive concept(s) is also directed to an isolated monoclonal antibody having an amino acid sequence that is at least 80% identical (such as at least 85% identical, 90% identical, or 95% identical) to the amino acid sequence of the monoclonal antibody produced by the hybridoma deposited with the ATCC, as described in detail herein above.

Anti-LRP6-1 (the mAb produced by the deposited hybridoma as described in detail herein above, also referred to interchangeably as "mAb2F1") comprises a heavy chain variable domain encoded by the nucleotide sequence of SEQ ID NO:4 and having an amino acid sequence as set forth in SEQ ID NO:5. Anti-LRP6-1 also comprises a light chain variable domain encoded by the nucleotide sequence of SEQ ID NO:6 and having an amino acid sequence as set forth in SEQ ID NO:7. The heavy chain comprises three complementarity regions (CDRs), designated CDRH1, CDRH2, and CDRH3. The light chain also comprises three CDRs, designated CDRL1, CDRL2, and CDRL3. The amino acid sequences of the CDRs, as well as the nucleotide sequences encoding said amino acid sequences, are shown in Table 1.

TABLE 1

| CDR | SEQ ID NO: of Nucleotide Sequence Encoding CDR | SEQ ID NO: of CDR's Amino Acid Sequence |
|---|---|---|
| CDRH1 | 8 | 9 |
| CDRH2 | 10 | 11 |
| CDRH3 | 12 | 13 |
| CDRL1 | 14 | 15 |
| CDRL2 | 16 | 17 |
| CDRL3 | 18 | 19 |

The presently disclosed inventive concept(s) is also directed to an antibody or antigen-binding fragment comprising a heavy chain variable domain that comprises an amino acid sequence encoded by SEQ ID NO:4 and/or an amino acid sequence as set forth in SEQ ID NO:5, and compositions comprising same. The presently disclosed inventive concept(s) is also directed to an antibody or antigen-binding fragment comprising a light chain variable domain that comprises an amino acid sequence encoded by SEQ ID NO:6 and/or an amino acid sequence as set forth in SEQ ID NO:7, and compositions comprising same. The presently disclosed inventive concept(s) is further directed to an antibody or antigen-binding fragment comprising a heavy chain that comprises at least one CDR having an amino acid sequence encoded by at least one of SEQ ID NOS: 8, 10 and 12 and/or an amino acid sequence as set forth in at least one of SEQ ID NOS: 9, 11 and 13, as well as compositions comprising same. The presently disclosed inventive concept(s) is further directed to an antibody or antigen-binding fragment comprising a light chain that comprises at least one CDR having an amino acid sequence encoded by at least one of SEQ ID NOS: 14, 16 and 18 and/or an amino acid sequence as set forth in at least one of SEQ ID NOS: 15, 17 and 19, as well as compositions comprising same.

In one particular embodiment, the presently disclosed inventive concept(s) is directed to an isolated monoclonal antibody (or antigen binding fragment thereof) that comprises the light chain variable region CDR3 (referred to herein interchangeably as "CDRL3") having the amino acid sequence of SEQ ID NO:19 and a heavy chain variable region CDR3 (referred to herein interchangeably as "CDRH3") having the amino acid sequence of SEQ ID NO:13. Said antibody specifically binds to an epitope within the LRP6 extracellular domain, wherein the LRP6 extracellular domain has the amino acid sequence of SEQ ID NO:2. The antibody may further include the light chain variable region CDR1 and CDR2 (referred to herein interchangeably as "CDRL1" and "CDRL2," respectively) having amino acid sequences of SEQ ID NOS:15 and 17, respectively, and may also further include the heavy chain variable region CDR1 and CDR2 (referred to herein interchangeably as "CDRH1" and "CDRH2," respectively) having amino acid sequences of SEQ ID NOS:9 and 11. In addition, the antibody may possess a heavy chain variable region having an amino acid sequence that is at least 90% identical to SEQ ID NO:5 and a light chain variable region having an amino acid sequence that is at least 90% identical to SEQ ID NO:7.

Though in some embodiments the antibodies and antigen binding fragments thereof include one or more CDRs that have amino acid sequences identical to the corresponding CDR of anti-LRP6-1, in some embodiments certain CDRs of the antibodies or antigen binding fragments thereof have amino acid sequences that are substantially similar, but not identical to the corresponding CDR of anti-LRP6-1. In some embodiments, the antibodies and antigen binding fragments thereof have CDR sequences identical to the corresponding CDR sequences of anti-LRP61, except for mutations in 6, 5, 4, 3, 2, or 1 CDR amino acid. In some embodiments, the amino acid mutations are present only in CRDL1, CDRL2, CDRH1, or CDRH2. In some embodiments, the mutations are only present in CDRL1, CDRL2, or CDRH1. In some embodiments, the mutations are conservative sequence modifications.

In certain embodiments, the antibodies and antibody fragments have a heavy chain variable region that includes CDR1, CDR2, and CDR3 sequences and a light chain variable region that includes CDR1, CDR2, and CDR3 sequences, where the light chain variable region CDR3 has an amino acid sequence of SEQ ID NO: 19 or conservative modifications thereof, and the heavy chain variable region CDR3 has an amino acid sequence of SEQ ID NO: 13 or conservative modifications thereof. In some embodiments, the heavy chain variable region CDR2 has an amino acid sequence of SEQ ID NO: 11 or conservative modifications thereof. In some embodiments, the light chain variable region CDR2 has an amino acid sequence of SEQ ID NO: 17 or conservative modifications thereof. In some embodiments, the heavy chain CDR1 has an amino acid sequence of SEQ ID NO: 9 or conservative modifications thereof. In some embodiments the light chain variable region has an amino acid sequence of SEQ ID NO: 15 or conservative modifications thereof.

In certain embodiments, the antibodies or antigen binding fragments thereof have a heavy chain variable region having an amino acid sequence that is at least 80%, 85%, 90%, 95%, 96%, 97%, 98%, 99%, or 100% identical to SEQ ID NO: 5. In certain embodiments the antibodies or antigen binding fragments have a light chain variable region having an amino acid sequence that is at least 80%, 85%, 90%, 95%, 96%, 97%, 98%, 99%, or 100% identical to SEQ ID NO: 7.

In some embodiments, the antibodies or antigen binding fragments thereof have a heavy chain variable region CDR3 having an amino acid sequence of SEQ ID NO: 13 and a heavy chain variable region CDR2 having an amino acid sequence of SEQ ID NO: 11. In some embodiments, the antibodies or antigen binding fragments thereof also have a heavy chain variable region CDR1 having an amino acid sequence of SEQ ID NO: 9. In some embodiments, the antigen binding antibody fragments do not include a light chain. For example, in some embodiments the antibody binding fragments are single domain antibodies, such as but not limited to, NANOBODIES®.

In some embodiments, the antibodies or antigen binding fragments thereof have a light chain variable region CDR3 having an amino acid sequence of SEQ ID NO: 19 and a light chain variable region CDR2 having an amino acid sequence of SEQ ID NO: 17. In some embodiments, the antibodies or antigen binding fragments thereof also have a light chain variable region CDR1 having an amino acid sequence of SEQ ID NO: 15. In some embodiments, the antigen binding antibody fragments do not include a heavy chain.

The antibodies or antigen binding fragments thereof can be prepared using an antibody having the $V_H$ and/or $V_L$ sequences of anti-LRP6-1 as starting material to engineer a modified antibody, which modified antibody may have altered properties from anti-LRP6-1, but retain the epitope specificity of anti-LRP6-1. An antibody or antigen binding fragment thereof can be engineered by modifying one or more residues within one or both variable regions (i.e., the heavy chain variable region or the light chain variable region), for example, within one or more CDR regions and/or within one or more framework regions. Additionally or alternatively, an antibody can be engineered by modifying residues within the constant region(s), for example, to alter the effector function(s) and/or immunogenicity of the antibody.

The presently disclosed inventive concept(s) further includes chimeric antibodies that comprise at least a portion of a variable region of Anti-LRP6-1 (i.e., the monoclonal antibody produce by hybridoma HLS2F1, ATCC accession number PTA-10663) and a constant region of an antibody derived from a human. Such antibodies retain anti-LRP6-1's antigen specificity and ability to inhibit the Wnt signaling pathway but have reduced immunogenicity in humans compared to anti-LRP6-1.

In some embodiments, the antibodies and antibody fragments are "humanized." Thus, in some embodiments, the antibodies or antigen binding fragments thereof are humanized forms of antibodies or fragments thereof (such as Fv, Fab, Fab', F(ab')2, or other antigen-binding subsequences of antibodies) that are principally comprised of the sequence of a human antibody or antibody fragment but contain one or more CDR from anti-LRP6-1.

Such humanized antibodies or antibody fragments can be generated by substituting one or more CDRs of anti-LRP6-1 for the corresponding sequences of a human antibody or antibody fragment. In certain embodiments, a humanized antibody is constructed by replacing 1, 2, 3, 4, 5, or 6 of the CDRs of a human antibody with CDRs from anti-LRP6-1. In certain embodiments, a humanized antibody or antibody fragment comprises variable regions in which all of the CDRs correspond to CDRs of anti-LRP6-1 and all of the framework regions (FRs) correspond to FRs of a human antibody. In some embodiments, the humanized antibody or antibody fragment has a CDRL3 and CDRH3 of anti-LRP6-1, but retains human sequences for one or more of CDRL1, CDRL2, CDRH1, or CDRH2. In some embodiments the human CDR sequences are selected to be similar in sequence to the corresponding anti-LRP6-1 CDR. In such embodiments, the human CDRs may have 5, 4, 3, 2, or 1 mutation, either collectively or individually, compared to their corresponding anti-LRP6-1 CDR. In some embodiments, the mutations are conservative sequence modifications. In some embodiments, a humanized antibody further comprises a constant region (Fc) of a human antibody.

In some instances, certain Fv framework residues of the human immunoglobulin are replaced by corresponding non-human residues. In some embodiments, humanized antibodies can also comprise residues which are found neither in the recipient antibody nor in the imported CDR or framework sequences. Methods of making and/or using humanized monoclonal antibodies can be found, for example, in, Sandborn et al., Gatroenterology, 120:1330 (2001); Mihara et al., Clin. Immunol., 98:319 (2001); Yenari et al., Neurol. Res., 23:72 (2001); Morales et al., Nucl. Med. Biol., 27:199 (2000); Richards et al., Cancer Res., 59:2096 (1999); Yenari et al., Exp. Neurol., 153:223 (1998); and Shinkura et al., Anticancer Res., 18:1217 (1998), all of which are expressly incorporated in their entirety by reference.

In some embodiments, the hinge region of CH1 of the antibodies is modified such that the number of cysteine residues in the hinge region is altered, e.g., increased or decreased. This approach is described further in U.S. Pat. No. 5,677,425 by Bodmer et al., incorporated by reference in its entirety. The number of cysteine residues in the hinge region of CH1 is altered to, for example, facilitate assembly of the light and heavy chains or to increase or decrease the stability of the antibody.

In some embodiments, the glycosylation of the antibody or antigen binding fragment thereof is modified. For example, an aglycoslated antibody can be made (i.e., the antibody lacks glycosylation). Glycosylation can be altered to, for example, increase the affinity of the antibody or antibody fragment for an antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., incorporated by reference in their entirety.

In some embodiments the antibody or antigen binding fragment is made such that it has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the presently disclosed inventive concept(s) to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach frucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180).

In some embodiments, the PEGylation of the antibodies or antigen binding fragments thereof is modified. An antibody can be PEGylated, for example, to increase the biological (e.g., serum) half-life of the antibody. To PEGylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In certain non-limiting embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be PEGylated is an aglycosylated antibody. Methods for PEGylating proteins are known in the art and can be applied to the antibodies of the presently disclosed inventive concept(s). See, for example, EP 0 154 316 by Nishimura et al. and EP 0 401 384 by Ishikawa et al.

In some embodiments, the antibodies and antibody fragments have minor variations in the amino acid sequences of antibodies or antigen binding fragments thereof described above, providing that the variations in the amino acid sequence maintain at least 75%, such as at least 80%, 90%, 95%, or 99%, of the original amino acid sequence, and provided that the antibodies/antibody fragments maintain the ability to specifically bind the extracellular domain of LRP6. In some embodiments, the modifications are conservative sequence modifications.

In some embodiments, the monoclonal antibodies of the presently disclosed inventive concept(s) neutralize an activity of LRP6. Therefore, said monoclonal antibodies may be referred to as a neutralizing antibody and/or a therapeutic antibody. In one embodiment, the monoclonal antibody specifically inhibits activation of the Wnt signaling pathway. In yet another embodiment, the monoclonal antibody inhibits the binding of a Wnt ligand to a receptor of the Wnt signaling pathway, thereby preventing activation of the Wnt signaling pathway by Wnt ligands. In another embodiment, the monoclonal antibody inhibits phosphorylation of LRP6. In certain embodiments the antibodies and antibody fragments inhibit the binding of both Wnt1 and Wnt3a to LRP6. In a further embodiment, the monoclonal antibody specifically blocks the over-expression of at least one pro-inflammatory factor and/or at least one pro-angiogenic factor induced by diabetic conditions. Said factors may include but is not limited to, VEGF, ICAM-1, TNF-α, CTGF, and combinations thereof.

The presently disclosed inventive concept(s) also includes a pharmaceutical composition comprising a therapeutically effective amount of at least one of the monoclonal antibodies or antigen fragments thereof described herein and compositions comprising same in combination with a pharmaceutically acceptable carrier. As used herein, a "pharmaceutically acceptable carrier" is a pharmaceutically acceptable solvent, suspending agent or vehicle for delivering the compounds of the presently disclosed inventive concept(s) to the human or animal. The carrier may be liquid or solid and is selected with the planned manner of administration in mind. Examples of pharmaceutically acceptable carriers that may be utilized in accordance with the presently disclosed inventive concept(s) include, but are not limited to, PEG, liposomes, ethanol, DMSO, aqueous buffers, oils, and combinations thereof.

The compositions of the presently disclosed inventive concept(s) (including but not limited to the pharmaceutical compositions described immediately herein above) may further comprise a second agent that has a synergistic effect with the monoclonal antibody, such as but not limited to, an anti-angiogenic agent, an anti-VEGF reagent, VEGF Trap, AVASTIN®, and the like.

The presently disclosed inventive concept(s) also includes methods of producing the monoclonal antibodies (or antigen binding fragment thereof) described herein above. The monoclonal antibodies and antibody fragments described herein may be produced by any appropriate methodology known in the art. For example, preparation of monoclonal antibodies can begin with the production of polyclonal antibodies generated by immunizing a suitable subject (e.g. a mouse) with a polypeptide immunogen (e.g., a polypeptide that includes a portion of the LRP6 extracellular domain). At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96), or trioma techniques.

The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387 402; Gefter, M. L. et al. (1977) Somatic Cell Genet. 3:231 36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Once the antibodies have been obtained, for example, once individual B cells have been identified and/or monoclonal antibodies have been produced, the sequences encoding the variable regions of these antibodies can be obtained. The variable region sequences can, for example, be obtained by first sequencing the antibody protein produced by the hybridoma, B-cell or phage and determining the encoding nucleic acid sequence. In one embodiment, the immunoglobulin variable region (VH and VL) DNA or cDNA may be sequenced instead. Where the antibody is derived from a hybridoma cell line or isolated B-cell, the cDNAs encoding the variable regions may be amplified using PCR by, for example, the methods described in Babcook et al. (Proc. Natl. Acad. Sci. USA, 93:7843-7848 (1996)), and in PCT Publication No. WO 92/02551. The contents of both references are expressly incorporated herein by reference in their entirety.

Thus, the antibodies and antigen binding fragments described herein can be generated using a method of producing a monoclonal antibody or antigen binding fragment thereof that includes the steps of providing a cell that produces a monoclonal antibody or antigen binding fragment thereof described herein and culturing the cell under conditions that permit production of the monoclonal antibody or antigen binding fragment thereof. In some embodiments, the cell is the hybridoma having ATCC Designation No. PTA-10663.

As an alternative to preparing monoclonal antibody-secreting hybridomas, a monoclonal specific for LRP6 can be identified and isolated by screening a recombinant combinatorial immunoglobulin library (e.g., an antibody phage display library or an antibody yeast display library) with the appropriate polypeptide to thereby isolate immunoglobulin library members that bind the polypeptide (see, e.g., Clackson et al., Nature, 352: 624-628 (1991); and Marks et al., J. Mol. Biol., 222:581-597 (1991), each of which is incorporated by reference).

Additionally, using antibody and antigen binding fragment sequences provided herein and known in the art, the monoclonal antibodies and antigen binding fragments, including chimeric or humanized monoclonal antibodies, can be made using standard recombinant DNA techniques. Such monoclonal antibodies and antibody fragments can be produced, for example, using methods described in U.S. Pat. No. 4,816,567; U.S. Pat. No. 5,565,332; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060, or U.S. Pat. No. 5,916,771, each of which is hereby incorporated by reference in its entirety.

The presently disclosed inventive concept(s) also includes isolated nucleic acid molecules encoding the amino acid sequence of any of the monoclonal antibodies (or fragments thereof) described herein above, including but not limited to, the heavy and/or light chain variable domains of said monoclonal antibodies as well as one or more CDRs of said heavy/light chain variable domains. In one embodiment, the presently disclosed inventive concept(s) comprises isolated nucleic acid molecules encoding at least one of (a) a heavy chain variable region having a CDR1 of SEQ ID NO:9; (b) a heavy chain variable region having a CDR2 of SEQ ID NO: 11; (c) a heavy chain variable region having a CDR3 of SEQ ID NO: 13; (d) a light chain variable region having a CDR1 of SEQ ID NO: 15; (e) a light chain variable region having a CDR2 of SEQ ID NO: 17; and (f) a light chain variable region having a CDR3 of SEQ ID NO: 19. In another embodiment, the presently disclosed inventive concept(s) comprises isolated nucleic acid molecules comprising at least one of SEQ ID NOS:4, 6, 8, 10, 12, 14, 16 and 18.

In one particular embodiment, the presently disclosed inventive concept(s) comprises an isolated nucleic acid molecule encoding a heavy chain variable region having a CDR3 of SEQ ID NO:13. The heavy chain variable region of said nucleic acid molecule may further include a CDR1 of SEQ ID NO:9 and a CDR2 of SEQ ID NO:11.

In another particular embodiment, the presently disclosed inventive concept(s) comprises an isolated nucleic acid molecule encoding a light chain variable region having a CDR3 of SEQ ID NO:19. The light chain variable region of said nucleic acid molecule may further include a CDR1 of SEQ ID NO:15 and a CDR2 of SEQ ID NO:17.

Nucleic acids of the presently disclosed inventive concept(s) can be obtained using standard molecular biology techniques. For antibodies expressed by hybridomas (e.g., hybridomas prepared as described above), cDNAs encoding the light and heavy chains of the antibody made by the hybridoma can be obtained using standard PCR amplification or cDNA cloning techniques. For antibodies obtained from an immunoglobulin gene library (e.g., using phage display techniques), nucleic acid encoding the antibody can be recovered from the library.

In some embodiments the isolated nucleic acid molecules have at least 80%, 85%, 90%, 95%, or 100% sequence identity to the nucleic acid molecules described above.

The presently disclosed inventive concept(s) also comprises a vector comprising any of the isolated nucleic acid molecules described herein above. The presently disclosed inventive concept(s) further include a host cell comprising said nucleic acid molecule(s) and/or said vector.

The presently disclosed inventive concept(s) also comprises a cell or cell line expressing the monoclonal antibodies described herein above, including but not limited to, Anti-LRP6-1. In one embodiment, the cell line is a hybridoma cell line. In yet another embodiment, the cell line is the hybridoma cell line deposited as described herein above.

The monoclonal antibodies, antibody fragments and nucleic acid compositions described herein have numerous therapeutic utilities for the treatment of Wnt pathway associated disorders or disorders involving LRP6 activity. These molecules and/or compositions can be administered to subjects, including human subjects, to treat or prevent a variety of disorders, including but not limited to, inflammation, vascular leakage, fibrosis, abnormal neovascularization, and cancer.

The presently disclosed inventive concept(s) is further related to a method of inhibiting activation of the Wnt signaling pathway, said method comprising administering a composition comprising any of the monoclonal antibodies described in detail herein above. If the composition does not include a second agent, the method may further comprise the administration of a second agent that has a synergistic effect with the monoclonal antibody, such as but not limited to, an anti-angiogenic agent, an anti-VEGF reagent, VEGF Trap, AVASTIN®, and the like.

The presently disclosed inventive concept(s) is further related to a method of inhibiting enzyme activity and/or enzyme production of at least one angiogenic, inflammatory and/or fibrogenic factor of DR. Said factors include but are not limited to, VEGF, ICAM-1, TNF-α, and CTGF. Said method comprises administering to a subject suffering from or predisposed to DR any of the pharmaceutical compositions described in detail herein above. If the composition does not include a second agent, the method may further comprise the administration of a second agent that has a synergistic effect with the monoclonal antibody, such as but not limited to, an anti-angiogenic agent, an anti-VEGF reagent, VEGF Trap, AVASTIN®, and the like.

The presently disclosed inventive concept(s) is also directed to a method of mediating/attenuating at least one retinal condition selected from the group consisting of retinal leukostasis, inflammation, vascular leakage, fibrosis, abnormal neovascularization (such as but not limited to, retinal neovascularization and/or choroidal neovascularization), and carcinogenesis in the retina. Said method comprises administering any of the pharmaceutical compositions described in detail herein above. If the composition does not include a second agent, the method may further comprise the administration of a second agent that has a synergistic effect with the monoclonal antibody, such as but not limited to, an anti-angiogenic agent, an anti-VEGF reagent, VEGF Trap, AVASTIN®, and the like.

The presently disclosed inventive concept(s) is further directed to a method of inhibiting and/or decreasing the occurrence and/or severity of at least one condition selected from the group consisting of diabetic retinopathy, diabetic macular edema, macular degeneration (including but not limited to, age related macular degeneration), cancer, and other inflammatory and neovascular disorders of the eye. Said method comprises providing a subject suffering from or predisposed to at least one of the above conditions, and administering an effective amount of any of the pharmaceutical compositions described in detail herein above, whereby the pharmaceutical composition inhibits activation of the Wnt signaling pathway, thereby inhibiting and/or decreasing the occurrence and/or severity of said condition/disorder. If the composition administered to the subject does not contain a second agent, the method may further comprise the administration of a second agent that has a synergistic effect with the monoclonal antibody, such as but not limited to, an anti-angiogenic agent, an anti-VEGF reagent, VEGF Trap, AVASTIN®, and the like.

In any of the methods described herein above, the method of administration may comprise injection of the composition into the vitreous of the eye.

Examples are provided hereinbelow. However, the present inventive concept(s) is to be understood to not be limited in its application to the specific experimentation, results and laboratory procedures. Rather, the Examples are simply provided as one of various embodiments and are meant to be exemplary, not exhaustive.

Example 1

Diabetic retinopathy (DR), the leading cause of blindness in the working age population, represents a common concern in types 1 and 2 of diabetes mellitus (DM). Accumulating evidence suggests that DR is a chronic inflammatory disorder. Retinal inflammation is believed to play a causative role in vascular leakage, which can lead to diabetic macular edema, and in retinal neovascularization (NV). It has been shown that levels of soluble intercellular adhesion molecule-1 (ICAM-1) and vascular cell adhesion molecule-1 are significantly higher in the vitreous from patients with proliferative diabetic retinopathy than in non-diabetic vitreous. Increased ICAM-1, vascular cell adhesion molecule-1, and e-selectin levels were found in the serum from patients with diabetic microangiopathy. In diabetic animal models, increased retinal ICAM-1 expression is believed to be responsible for leukocyte adhesion or leukostasis and increased vascular permeability. Leukostasis is believed to contribute to capillary nonperfusion and local ischemia, which subsequently induces the overexpression of vascular endothelial growth factor (VEGF). Increased VEGF levels are responsible for the retinal vascular leakage and retinal NV. Recent studies have indicated that oxidative stress, induced by hyperglycemia, contributes to retinal inflammation in diabetes. However, the pathogenic mechanisms by which diabetes and oxidative stress induce inflammation are not certain at the present time.

Wnts are a group of secreted, cysteine-rich glycoproteins, which bind to a coreceptor complex of frizzled (Fz) receptors and low-density lipoprotein receptor-related protein 5 or 6 (LRP5/6) and regulate expression of a number of target genes through an intracellular signaling pathway, namely the Wnt pathway. In the absence of Wnt ligands, β-catenin, a down-stream effector of the canonical Wnt pathway, is phosphorylated by a protein complex containing glycogen synthase kinase-3β. The phosphorylated β-catenin is constantly degraded, to prevent its accumulation. On binding of certain Wnts to the Fz-LRP5/6 coreceptors, phosphorylation of β-catenin is inhibited, which prevents the degradation of β-catenin and results in its accumulation. β-catenin is then translocated into the nucleus, associates with T-cell factor for DNA binding, and regulates expression of target genes including VEGF.

LRP5/6 are known to play a critical role in Wnt/β-catenin signaling. On binding with Wnt ligands, LRP6 dimerizes with Fz receptor, which is the first and essential step in activation of the Wnt pathway. The cytoplasmic domain of LRP6 has multiple modular phosphorylation sites, and phosphorylation of LRP6 is an essential event for activation of the canonical Wnt pathway, as the phosphorylation of LRPE6 promotes the recruitment of the scaffold protein Axin, and thus, activates the canonical Wnt signaling pathway.

Recent evidence indicates that the canonical Wnt pathway plays a role in angiogenesis. Extensive studies have shown that the Wnt pathway up-regulates nuclear factor κB, signal transducer and activator of transcription 3 and a number of inflammatory factors, and thus, plays a key role in inflammation. The present Example investigated the possible role of the Wnt signaling pathway in DR by using human donor eyes, diabetic animal models, and cultured cells.

Materials and Methods of Example 1

Human Tissue: Normal and diabetic eyes fixed in 10% neutral buffered formalin (NBF) within 12 hours postmortem and were obtained from National Diseases Research Interchange (Philadelphia, Pa.) with full ethical approval for use in research. Diabetic eyes were categorized according to a standardized protocol (Khaliq et al., Lab Invest, 78:109-116 (1998)).

Animals: Akita mice were purchased from the Jackson Laboratory (Bar Harbor, Me.), and Brown Norway rats were purchased from Charles River (Wilmington, Mass.). Care, use, and treatment of all animals in this study were in strict agreement with the Statement for the Use of Animals in Ophthalmic and Vision Research from the Association for Research in Vision and Ophthalmology.

Isolation and Culture of Bovine Retinal Capillary Endothelial Cells and Pericytes: Bovine retinal capillary endothelial cells (RCEC) and pericytes were isolated from bovine eyes, as described by Grant and Guay (Invest Opthalmol Vis Sci, 32:53-64 (1991)) with some modifications. At passage 3 or 4, the purity of the cells in culture was determined. The identity of RCEC was confirmed by a characteristic cobblestone morphology and the incorporation of acetylated low-density lipoprotein labeled with a fluorescent probe, Dil (1,1'-dioctadecyl-3,3,3',3'-tetramethylindocarbocyanine perchlorate) (Biomedical Technologies, Inc.; Stoughton, Mass.). Purity of the pericyte culture was determined by immunostaining using a fluorescein isothiocyanate-conjugated antibody specific to α-smooth muscle actin (Sigma; St. Louis, Mo.).

Induction of Diabetes in Rats: Experimental diabetes was induced by an intraperitoneal injection of streptozotocin (STZ) (50 mg/kg in 10 mmol/L of citrate buffer; pH 4.5) into anesthetized Brown Norway rats (8 weeks of age) after an overnight fast. Age-matched control rats received an injection of citrate buffer alone for non-diabetic control. Blood glucose levels were measured 48 hours after the STZ injection and monitored weekly thereafter. Only the animals with glucose levels >350 mg/dl were considered diabetic.

The Oxygen-Induced Retinopathy Model and Analysis of Retinal NV: The oxygen-induced retinopathy (OIR) model was induced in Brown Norway rats as described previously (Ricci., Doc Opthalmol, 74:171-177 (1990)). Quantification of preretinal vascular cells was described by Smith et al. (Invest Opthalmol Vis Sci, 35:101-111 (1994)). Briefly, the eyes of eight rats from each group at postnatal day 18 (P18) were enucleated, fixed with 10% formaldehyde, sectioned, and then stained with H&E. The nuclei of vascular cells on the vitreal side of the retina were counted under a light microscope in a double-blind study. Ten sagittal sections from each eye were examined, and cell numbers were averaged in each group of animals. The average number of preretinal vascular nuclei was compared with that in the control group by using Student's t-test.

Retinal Angiography with High-Molecular-Weight Fluorescein: Rats at P18 were anesthetized with 10 mg/kg xylazine plus 75 mg/kg ketamine i.p. and perfused with 50 mg/ml high molecular weight fluorescein isothiocyanate-dextran (molecular weight $2\times10^6$; Sigma) via intraventricle injection as described by Smith et al. (Invest Opthalmol Vis Sci, 35:101-111 (1994)). The animals were immediately euthanized. The eyes were enucleated and fixed with 4% paraformaldehyde in PBS for 10 minutes. The retina was then separated from the eyecup and fixed with 4% paraformaldehyde for 3 hours. Several incisions were made to the retina, which was flat-mounted on a gelatin-coated slide. The vasculature was then examined under a fluorescence microscope (Axioplan2 Imaging; Carl Zeiss; Jena, Germany).

Immunohistochemistry: Immunohistochemistry was performed as described (Chen et al., Invest Opthalmol Vis Sci, 47:1177-1184 (2006)). The primary antibodies specific for LRP5/6 (Abcam; Cambridge, Mass.) and hypoxia-inducible factor-1α (HIF-1α) (Santa Cruz Biotechnology; Santa Cruz, Calif.) were used at a dilution of 1:200, and antibody for β-catenin (Cell Signaling Technology, Danvers, Mass.) at a dilution of 1:300. The secondary antibodies were fluorescein isothiocyanate-conjugated goat anti-mouse IgG (Jackson ImmunoResearch Laboratory, Inc; West Grove, Pa.) and Texas Red-conjugated goat anti-rabbit IgG (Jackson ImmunoResearch Laboratory) at a dilution of 1:200.

Measurement of Reactive Oxygen Species Generation: Cellular oxidative stress was determined by measuring intracellular reactive oxygen species (ROS) generation (Degli, Methods, 26:335-340 (2002); and Amer et al., Eur J Haematol, 70:84-90 (2003)). Briefly, the treated and untreated cells at a density of $2\times10^6$ cells/ml were incubated with freshly prepared 5-(and 6-)chloromethyl-2',7'-dichlorodihydrofluorescein diacetate, acetyl ester (CM-H2-DCF-DA) at 37° C. in the dark. The CM-H2-DCF-DA-loaded cells were rinsed twice in PBS and analyzed immediately by fluorometer at 488 nm excitation and 530 nm emission. Data were expressed as fluorescence intensity in arbitrary units from the average of three separate experiments.

Intravitreal Injection of Dickkopf Homolog 1: Briefly, animals were anesthetized with a 50:50 mix of ketamine (100 mg/ml) and xylazine (20 mg/ml), and their pupils were dilated with topical application of phenylephrine (2.5%) and tropicamide (1%). A sclerotomy was created approximately 0.5 mm posterior to the limbus with a blade, and a glass injector (~33 gauge) connected to a syringe filled with 3 µl of the specified concentrations of Dickkopf homolog 1 (DKK1) or bovine serum albumin (BSA) was introduced through the sclerotomy into the vitreous cavity.

Soluble ICAM-1 Enzyme-Linked Immunosorbent Assay: A commercial soluble ICAM-1 (sICAM-1) enzyme-linked immunosorbent assay kit (R&D Systems, Inc.; Minneapolis, Minn.) was used to measure sICAM-1 levels in mouse retinal tissues, following the manufacturer's protocol. The samples from mouse tissues were diluted 10 times to ensure that the sICAM-1 concentration fell within the range of the sICAM-1 standard curves.

Western Blot Analysis: The same amounts of retinal proteins from each rat or mouse were used for Western blot analysis using specific primary antibodies for each protein and blotted with a horseradish peroxidase-conjugated secondary antibody (Chen et al., Invest Opthalmol Vis Sci, 47:1177-1184 (2006)). The signal was developed with a chemiluminescence detection kit (ECL; Amersham International; Piscataway, N.J.). Blots were then stripped and reblotted with an antibody specific for β-actin.

The primary antibodies used are specific for LRP5/6 (Santa Cruz Biotechnology) and HIF-1α (Santa Cruz Biotechnology) at a dilution of 1:500, and the anti-β-catenin antibody (Cell Signaling Technology) at a dilution of 1:3000.

Vascular Permeability Assay: Vascular permeability was quantified by using Evans blue as a tracer as described previously (Gao et al., Diabetologica, 46:689-698 (2003)).

Results of Example 1

Figure 1:
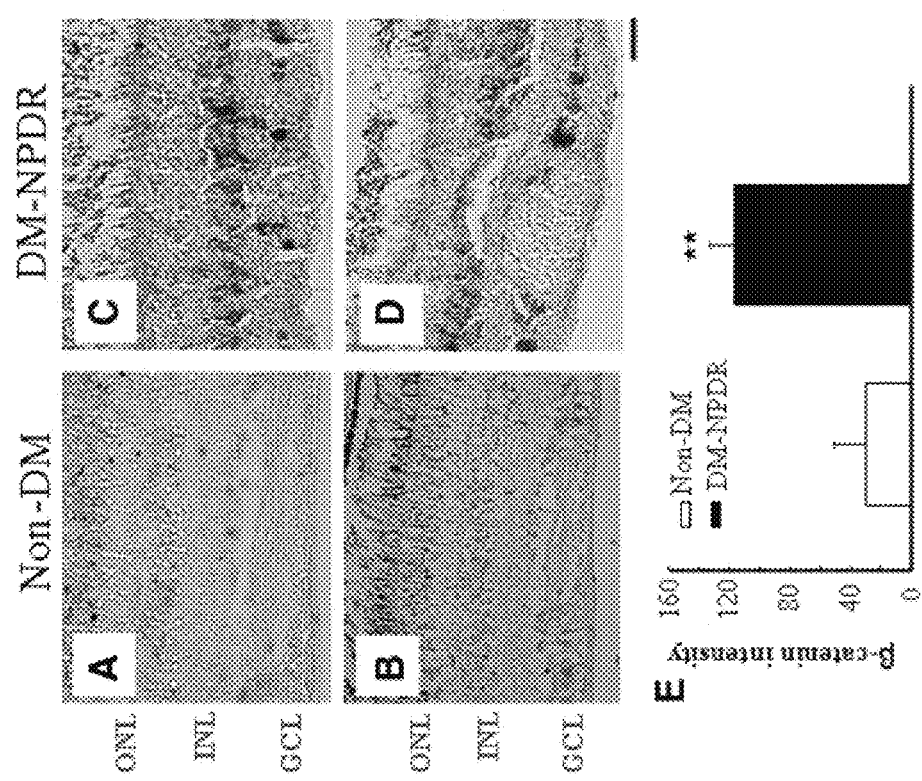
FIG. 1 illustrates activated Wnt signaling in the human retina with DR. Retinal sections from five non-DM donors and six diabetic donors with NPDR were immunostained with an antibody for β-catenin. The signal was developed with the diaminobenzidine method (brown color). Representative retinal images from two non-DM (A and B) and two NPDR donors (C and D) showed more intensive signals of β-catenin in the inner retina and increased β-catenin staining in the nuclei of the retinal cells from the DM-NPDR donors, compared with that from the non-DM subjects. Scale bar=20 μm. E: β-catenin signal was quantified by using morphometric analysis software and expressed as arbitrary units (mean±SD). **P<0.01.

The Wnt Pathway Is Activated in the Retina of Human Patients with DR: To evaluate the activation status of the Wnt pathway in the retina of diabetic patients, retinal levels of total β-catenin, an essential effector of the canonical Wnt pathway, were measured. Ocular sections from six diabetic donors with nonproliferative diabetic retinopathy (NPDR) and those from five non-diabetic donors were stained for β-catenin by using immunohistochemistry. Under the same development intensity, there was a statistically significant increase in β-catenin staining intensity in the inner retina from the donors with NPDR, while there were only basal levels of β-catenin signal in the retina from the non-diabetic donors (FIG. 1, A-E). Moreover, immunohistochemistry showed that the donors with NPDR had more intensive β-catenin signals (brown color) in the nuclei of the retinal cells, compared with that in the non-diabetic donors (FIG. 1), indicating increased nuclear translocation of β-catenin in the retinas from patients with NPDR.

Activation of the Wnt Pathway in the Retinas of Akita Mice, STZ-Induced Diabetic Rats, and Rats with OIR: To confirm the activation of the Wnt pathway in the retina of DR animal models, β-catenin levels were measured in the retinas from Akita mice, a genetic model of type-1 diabetes, STZ-induced diabetic rats, and in OIR rats, a model of ischemia-induced retinal NV. As shown by Western blot analysis, β-catenin levels were elevated in the retinas from Akita mice at the age of 16 weeks, compared with that in their non-diabetic littermates (FIG. 2A). Similarly, retinal β-catenin levels were also elevated in STZ-diabetic rats at 16 weeks after the induction of diabetes, compared with age-matched non-diabetic rats (FIG. 2B). In rats at the age of postnatal day 16 (P16) under constant normoxia, low levels of β-catenin were detected in the retina, while the OIR rats at the same age showed dramatically increased β-catenin levels in the retina (FIG. 2C).

Figure 2:
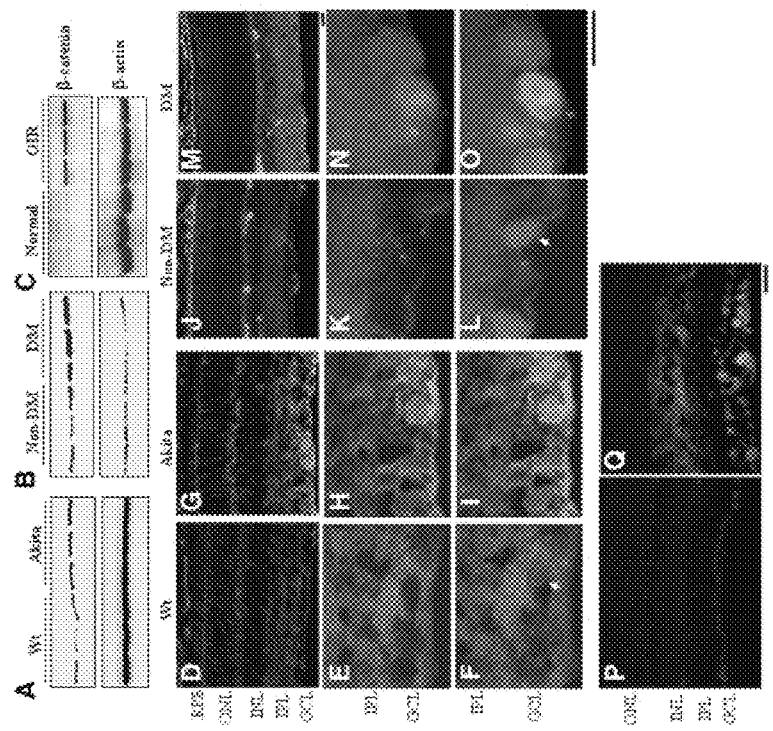
FIG. 2 depicts increased β-catenin levels in the retinas of Akita mice, STZ-induced diabetic rats, and OIR rats. The retinas from Akita mice at 16 weeks of age, STZ-DM rats at 16 weeks following the STZ injection, OIR rats at the age of P16, and age-matched non-diabetic or normoxic controls were used for Western blot (A-C) and immunohistochemistry (D-Q) analyses of β-catenin. A-C: The same amount (50 μg) of retinal proteins from each animal was blotted with an antibody specific for β-catenin. The membranes were stripped and reblotted with an antibody for β-actin. Each lane represents an individual animal. D-Q: Representative retinal sections from Akita mice (G-I) and their non-diabetic littermates (D-F), STZ-DM rats (M-O) and non-DM rats (J-L), OIR rats (Q), and age-matched normal rats maintained under constant normoxia (P) were immunostained with an antibody for β-catenin. F, I, L, and O: The nucleus was counterstained with 4',6-diamidino-2-phenylindole (DAPI) (colored red) and merged with β-catenin signal. Red arrows (in I and O) indicate the nuclei showing green or orange color as a result of increased β-catenin signal in the nuclei of diabetic retinas, while the white arrows (in F and L) point to nuclei (red color) in non-diabetic retinas. Scale bar=20 μm.

To identify the cellular location of the β-catenin accumulation, ocular sections from the eyes of Akita mice, STZ-diabetic rats, OIR rats, and their respective controls were stained with an antibody specific for β-catenin by using immunohistochemistry. More intensive β-catenin signals (green color) were detected in the inner retinas of the Akita mice, STZ-diabetic rats, and OIR rats, when compared with their respective controls (FIG. 2, D-Q). Increased β-catenin signals in the nuclei of retinal cells were also observed in the diabetic animals and OIR rats (FIG. 2, D-Q).

Increased Retinal Levels of LRP5/6 in Diabetic and OIR Rats: To further assess the activation status of the Wnt pathway, retinal levels of LRP5/6, coreceptors in the Wnt pathway, were measured by Western blot analysis. The results showed that retinal levels of LRP6 were higher in the retinas from STZ-induced diabetic rats at 16 weeks following the onset of diabetes than that in non-diabetic controls (FIG. 3A). Similarly, retinal LRP6 levels were also elevated in the retinas from OIR rats at the age of P16, compared with age-matched normoxia controls (FIG. 3B).

Figures 3, 4:
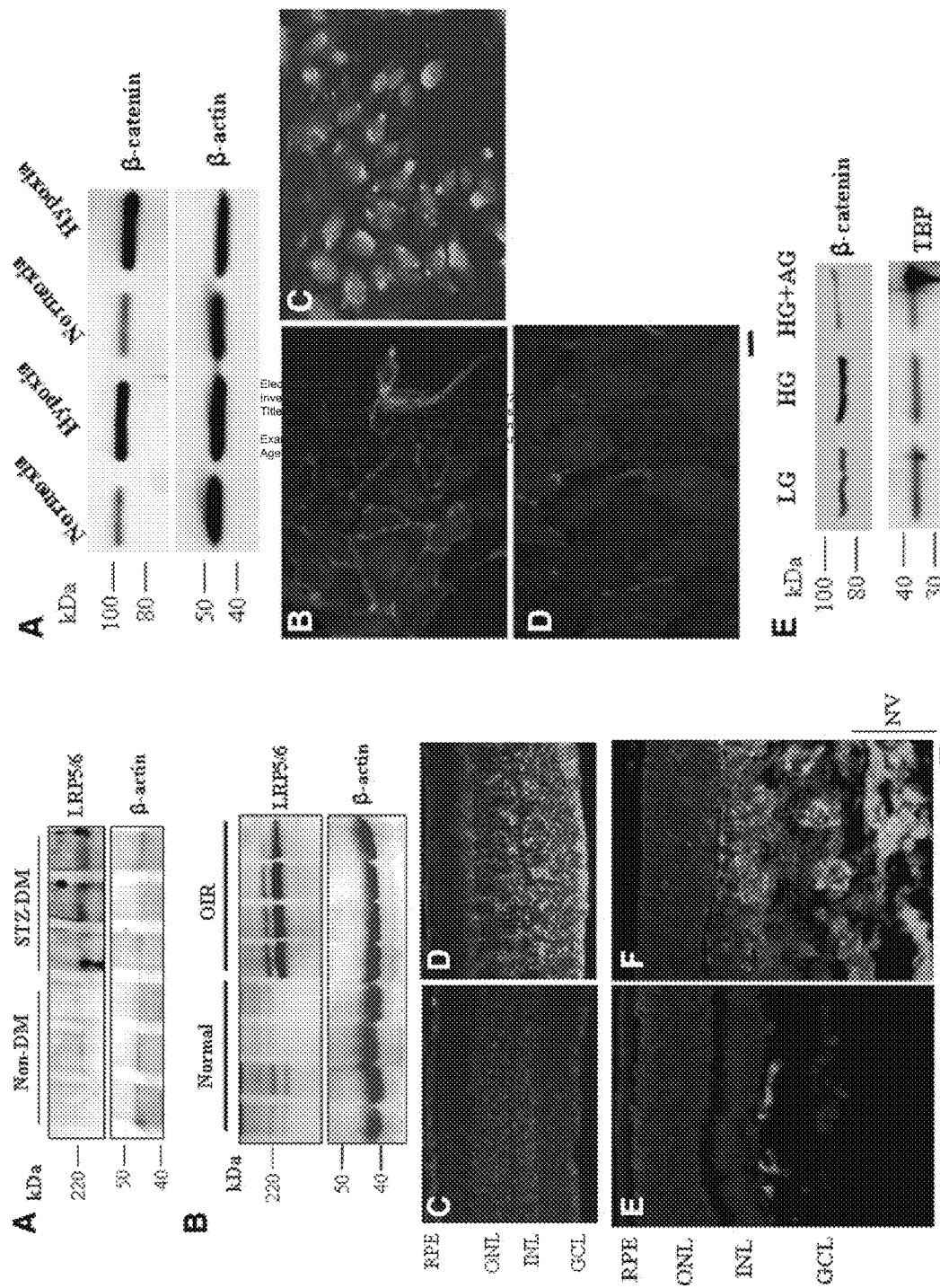
FIG. 3 illustrates up-regulated expression of LRP5/6 in the retinas of STZ-diabetic and OIR rats. A and B: The same amount of retinal proteins (100 μg) from three STZ-induced diabetic rats 16 weeks after the onset of diabetes and age-matched non-diabetic rats (A), and four OIR rats and normal rats at age of P16 (B) was used for Western blot analysis using an antibody specific for LRP5/6 (Santa Cruz Biotechnology). The same membranes were stripped and reblotted with an antibody for β-actin. C-F: Retinal sections from STZ-diabetic rats (D) and non-DM controls (C), and those from OIR rats (F) and their normoxic controls (E) were immunostained with the antibody against LRP5/6 (green). The nuclei were counterstained with DAPI (red). Original magnification, ×400.
FIG. 4 depicts induction of Wnt signaling by hypoxia and oxidative stress. A: RCEC were exposed to 2% oxygen and normoxia for 14 hours. Levels of total β-catenin were determined by Western blot analysis using the same amount (50 μg) of total proteins from each sample and normalized to β-actin levels. Note that the blot represents two independent experiments. B-D: RCEC were treated with low glucose (LG; 5 mmol/L glucose and 25 mmol/L mannitol, B), high glucose (HG, 30 mmol/L glucose, C), and high glucose plus 10 μmol/L aminoguanidine (HG+AG, D) for 24 hours. The subcellular distribution of β-catenin was revealed by immunocytochemistry by using the antibody for β-catenin. E: The same amount of isolated nuclear proteins (50 μg) from each of the above groups was blotted with an antibody for β-catenin and normalized to TATA box-binding protein (TBP) levels.

Immunohistochemical analysis in ocular sections showed increased LRP5/6 signals in the inner retina of STZ-induced diabetic rats (green color in FIGS. 3, C and D), compared with non-diabetic controls. In OIR rats, the more intensive LRP5/6 signals were detected primarily in the retinal vasculature (FIGS. 3, E and F).

Hypoxia and Oxidative Stress Are Responsible for the Wnt Pathway Activation in Diabetes: To identify the cause for the Wnt pathway activation in diabetes, the effects of hypoxia and hyperglycemia, known pathogenic factors of DR, on Wnt signaling were evaluated in vitro. As shown by Western blot analysis, exposure of primary RCEC to hypoxia (2% oxygen) for 14 hours increased the total β-catenin levels (FIG. 4A), indicating that hypoxia is a causative factor for the Wnt pathway activation in the retina of the diabetic and OIR models.

RCEC were also exposed to 30 mmol/L glucose for 24 hours, in the presence and absence of 10 μmol/L aminoguanidine, which is known to have anti-oxidant activities. The subcellular distribution of β-catenin in RCEC was determined by using immunocytochemistry. In the cells cultured under the low glucose medium (5 mmol/L glucose and 25 mmol/L mannitol), β-catenin was distributed primarily in the cytosol and membrane, and was undetectable in the nuclei (green color in FIG. 4B). The high glucose medium induced β-catenin nuclear translocation (FIG. 4C), indicating that high glucose alone is sufficient to activate the Wnt pathway. Under the same condition, aminoguanidine inhibited the nuclear translocation of β-catenin induced by high glucose (FIG. 4D). Consistently, Western blot analysis using isolated nuclear proteins showed that nuclear levels of β-catenin were elevated in the RCEC exposed to the high glucose medium, compared with those in the low glucose medium. Aminoguanidine blocked the high glucose-induced increase of nuclear β-catenin levels, suggesting that oxidative stress is responsible for the high glucose-induced activation of the Wnt pathway (FIG. 4E).

Blockade of the Wnt Pathway Ameliorates Retinal Inflammation, Vascular Leakage, and NV in DR Models: To further establish the causative role of the Wnt pathway activation in DR, the Wnt pathway activation was blocked in the retinas of the DR models by using DKK1, a specific inhibitor of the Wnt pathway. An intravitreal injection of different doses of purified DKK1 into STZ-diabetic rats reduced retinal soluble ICAM-1 levels in a dose-dependent manner, when compared with that in the contralateral eyes injected with the same amounts of BSA, indicating that Wnt signaling is responsible for retinal inflammation in diabetic rats (FIG. 5A). To evaluate the role of Wnt signaling in retinal vascular leakage in diabetic rats, purified DKK1 was injected into the vitreous of the right eye (1.2 μg/eye) of STZ-diabetic rats at 16 weeks following the onset of diabetes, and the same amounts of BSA into the contralateral eyes for control. Retinal vascular leakage was measured 48 hours after the injection by using Evans blue as a tracer, and normalized by total retinal protein concentrations. Consistently, vascular permeability assays showed that retinal vascular leakage was significantly decreased in the eyes injected with DKK1 in diabetic rats, compared with that in the contralateral eyes injected with the same dose of BSA (FIG. 5B).

The Wnt pathway was also blocked by injection of DKK1 (1.0 μg/eye) into OIR rats at age P14. Two days after the injection, expression of pro-inflammation factor such as COX2 and permeability factor VEGF was significantly down-regulated (FIGS. 5, C and D). Consistently, vascular permeability assays showed that retinal vascular leakage was significantly decreased in the eyes injected with 1 μg/eye DKK1, compared with that in the contralateral eyes injected with the same dose of BSA (FIG. 5E).

To evaluate the role of Wnt signaling in the ischemia-induced retinal NV, DKK1 was injected into the vitreous of OIR rats at the age of P14. The retinal vasculature was visualized by fluorescein angiography in whole-mounted retina at P18. The DKK1 injection induced apparent decreases of neovascular areas and tufts, compared with the contralateral eyes injected with BSA (green color in FIG. 5, F-I). Retinal NV was quantified by counting preretinal vascular cells, which showed significant decreases in pre-retinal vascular cells in the DKK1-injected eyes compared with that in the contralateral eyes injected with BSA (FIG. 5J).

Blockade of Wnt Signaling Attenuates the High Glucose-Induced HIF-1 Activation and ROS Generation: HIF-1 activation is known to play a crucial role in the overexpression of VEGF and retinal NV in DR. Here it was examined whether the role of Wnt signaling is through HIF-1. Cultured RCEC were exposed to 30 mmol/L glucose in the presence and absence of different concentrations of DKK1 for different durations, with 5 mmol/L glucose and 25 mmol/L mannitol as negative controls, and 1 μg of tumor necrosis factor (TNF)-α as the positive control. As shown by immunocytochemistry using an anti-HIF-1α antibody, DKK1 inhibited the HIF-1α nuclear translocation, a key step in its activation, induced by the high glucose medium (green color in FIG. 6, A-D).

As oxidative stress is believed to be a key pathogenic factor in DR, the effect of Wnt signaling on ROS generation induced by high glucose and TNF-α was evaluated. As shown by ROS measurement, both TNF-α and the high glucose medium (30 mmol/L) significantly increased ROS production in RCEC, compared with the low glucose medium. DKK1 showed a dose-dependent (6.25 to 100 nmol/L) reduction of ROS generation induced by TNF-α and high glucose. At high concentrations (50 and 100 nmol/L), DKK1 decreased the ROS generation to the same extent as that of 10 μmol/L of aminoguanidine (FIG. 6E).

Discussion of Example 1

The Wnt signaling pathway has been shown to regulate multiple biological and pathological processes. However, the association of the Wnt pathway with DR has not been reported previously. The present Example demonstrates for the first time that the Wnt pathway is activated by oxidative stress and hypoxia in DR in humans and animal models. Furthermore, it has been shown herein that blockade of Wnt signaling with a specific inhibitor of the Wnt pathway ameliorates retinal inflammation, vascular leakage, and NV in the DR models, indicating that the Wnt pathway plays a causative role in DR. Therefore, these observations have established a new pathogenic role for the Wnt pathway.

β-catenin is an essential down-stream effector in the canonical Wnt pathway. The present results obtained using human ocular sections revealed increased retinal levels of β-catenin and enhanced nuclear translocation, a key step in the activation of β-catenin, in the inner retinal cells in patients with DR, compared with that in non-diabetic donors. The location of the β-catenin activation in the inner retina correlates with the pathological changes in DR. The activation of Wnt signaling in the retina with NPDR, which manifests inflammation and vascular leakage but lacks of NV, indicate that the Wnt activation can occur at early stages of DR, before the proliferative stages.

To confirm the activation of the Wnt pathway in the retina with DR, retinal β-catenin levels were examined in three animal models of DR. STZ-induced diabetes is a commonly used type-1 diabetic model. Akita mouse is a genetic model of type-1 diabetes. Both of the models have been shown to develop retinal inflammation and vascular leakage but not retinal NV, and thus, are NPDR models. Western blot analysis and immunohistochemistry both showed that total levels of β-catenin were higher in the retinas of STZ-diabetic rats than in the age-matched non-diabetic controls. Similarly, Akita mice also had increased β-catenin levels compared with their non-diabetic littermates. The results from these diabetic models indicate that the activated Wnt pathway correlates with retinal inflammation and vascular leakage.

OIR is a commonly used model of ischemia-induced retinal NV. Although it is not a diabetic model, the pathological features of this model, such as preretinal NV, vascular leakage, and overexpression of HIF-1 and VEGF in the retina, resemble that of proliferative diabetic retinopathy. Thus, OIR is commonly accepted as a proliferative diabetic retinopathy model. In OIR rats, β-catenin levels were also increased in the inner retina. These results indicate a potential role of the Wnt pathway in ischemia-induced retinal NV.

LRP5/6 are closely related coreceptors of Wnt ligands. To confirm the activation of the Wnt pathway in DR, the retinal levels of LRP5/6 have been measured in the DR models. Western blot analysis and immunohistochemistry both showed that the retinal levels of LRP5/6 were elevated in the STZ-induced diabetic and OIR models. In contrast, no significant changes of the Fz receptor levels were detected in the retina of both of the models. Together with the β-catenin accumulation in these models, these results demonstrate that the Wnt pathway is overactivated in DR.

DR is a complex and multifactorial disorder. It has been shown that hypoxia and hyperglycemia are the major pathogenic factors. To identify the cause for the Wnt pathway activation in diabetes, the impacts of hypoxia and high glucose on Wnt signaling were assessed. In cultured retinal endothelial cells, hypoxia and high glucose medium induced the accumulation of β-catenin and its nuclear translocation. These experiments indicate that hypoxia and hyperglycemia are causative factors for the Wnt pathway activation in diabetes.

Oxidative stress induced by hyperglycemia has been shown to be a key pathogenic factor for retinal inflammation and vascular injury. To test the role of the oxidative stress in the Wnt pathway activation induced by high glucose, aminoguanidine was used, as it has antioxidant activities. Both immunocytochemical and Western blot analyses showed that the β-catenin nuclear translocation induced by high glucose medium can be attenuated by aminoguanidine alone, which indicates that the oxidative stress induced by high glucose is a direct cause of the Wnt pathway activation in DR.

The Wnt pathway is known to be activated under many pathological conditions. To establish the causative role of activated Wnt signaling in DR, the Wnt pathway in the DR models was blocked by using DKK1, a specific peptide inhibitor of the Wnt pathway. DKK1 is known to bind to coreceptors LRP5/6 with high specificity and affinity, and block the dimerization of LRP5/6 with the Fz receptor, an essential step in Wnt pathway activation. In the DR models, an intravitreal injection of DKK1 alone is sufficient to mitigate retinal inflammation as it blocks the overexpression of pro-inflammatory factors such as ICAM-1 and COX-2. Similarly, DKK1 also reduced retinal vascular leakage and ameliorated the ischemia-induced retinal NV. These results indicate that blockade of the Wnt pathway alone is sufficient to ameliorate DR. Further, activation of the Wnt pathway alone without high glucose in cultured cells was sufficient to induce VEGF expression. These results indicate that the Wnt pathway activation plays a causative role in DR. This conclusion is consistent with previous observations in other tissues that the Wnt pathway mediates inflammation and angiogenesis.

To elucidate the mechanism by which Wnt signaling mediates DR, the effects of the Wnt pathway in oxidative stress were evaluated. In cultured endothelial cells, ROS generation was significantly elevated by high glucose and by TNF-α, an inflammatory factor. Blocking Wnt signaling with DKK1 inhibited the ROS generation induced by high glucose medium and TNF-α. These results indicate that the pathogenic role of the Wnt pathway in DR may be via induction of oxidative stress and subsequently induction of inflammation in the retina.

In summary, this Example provides the first evidence showing that the Wnt pathway activation is a novel pathogenic mechanism for DR in both human patients and in animal models. Thus, the Wnt pathway represents a new target for pharmaceutical intervention of DR and therefore has therapeutic potential in the treatment of DR.

Example 2

Retinal NV is a major pathological feature leading to vision loss in DR. VEGF is a well-known key factor in stimulating the retinal NV formation in the DR. Example 1 above demonstrates that the Wnt pathway is up-regulated in the retina of diabetic animals and in an ischemia-induced animal model. Furthermore, Example 1 also demonstrates that inhibition of the Wnt pathway on the top using Dkk1, a Wnt pathway inhibitor through binding of LRP6, reduces retinal VEGF expression; retinal inflammation and retinal permeability in the retina of STZ induced diabetic model and OIR model.

Despite the above facts that suggest that Dkk1 has great potential in the treatment of retinal NV in DR, it is noteworthy that the preventive effect of Dkk1 in the retina is only temporal due to its short half-life, which requires multiple introvitreous injections and thus serious injury to the eye. Moreover, Dkk1 cannot be expressed as a soluble protein from *E. coli*, and therefore the cost of its synthesis is high. Thus, other inhibitors of Wnt which retain the anti-angiogenic activities and have a longer half-life is desired. Since the essential anti-angiogensis activities of Dkk1 are through binding to the LRP6 thus blocking the LRP6 activity, the presently disclosed inventive concept(s) provides an antibody that directly blocks LRP6 activity, thereby inhibiting the Wnt pathway and consequently preventing retinal inflammation and retinal NV. One advantage of this antibody over a peptide inhibitor is that the effect of the antibody lasts longer than 4 weeks in vivo. Moreover, since antigen-antibody binding is more specific and higher affinity, this monoclonal Anti-LRP6-1 will have the same or more potent anti-angiogenic activity on DR than that of Dkk1.

Results of Example 2

Generation of mouse mAbs that neutralize LRP6: A number of clones of mouse monoclonal antibodies were generated using standard hybridoma techniques using the recombinant ectodomain of LRP6 (described in detail in the other Examples). Out of numerous positive clones of mAb, the mAb Anti-LRP6-1 (the hybridoma producing said antibody deposited with the ATCC as described herein above), was identified in this manner. Anti-LRP6-1 was selected based on its specificity for endogenous LRP6 in various cell lines.

Figure 7:
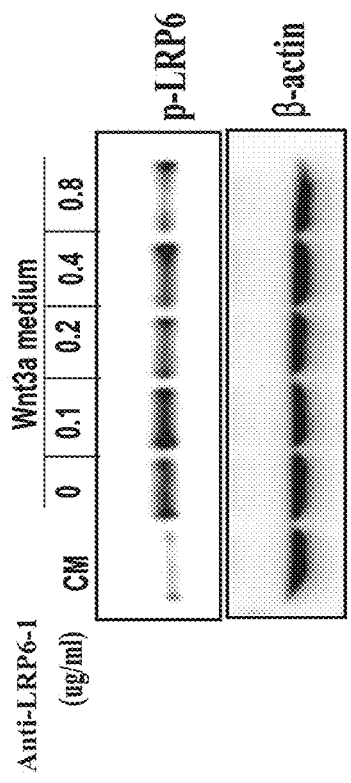
FIG. 7 depicts a Western blot analysis demonstrating that Anti-LRP6-1 mAb inhibits LRP6 activity completely. RCECs were pretreated with Anti-LRP6-1 for 10 minutes, and then 20% Wnt3a-containing medium was introduced and cultured for another 16 hours. Western blotting analysis showed that LRP6 phosphorylation was inhibited in a dose-dependent manner, indicating LRP6 activity was blocked.

Anti-LRP6 antibodies neutralize human LRP6-mediated cellular activities:

Anti-LRP6 mAb inhibits LRP6 activity: Next, inhibition of LRP6 phosphorylation by anti-LRP6 antibodies was measured. Under normal conditions, LRP6 is not activated. Wnt stimulates LRP6 activation by phosphorylation at its PPPSP motif, which is reiterated five times in the cytoplasmic domain of LRP6; thus, Wnt 3a containing medium was used for ligand-mediated receptor activation. The data showed that when Anti-LRP6-1 was introduced into Wnt3a-containing medium before its addition to the cells, LRP6 phosphorylation was inhibited in a dose-dependent manner (FIG. 7) with $IC_{50}$ values in the range of 0.21-0.44 µmol/L.

Figure 8:
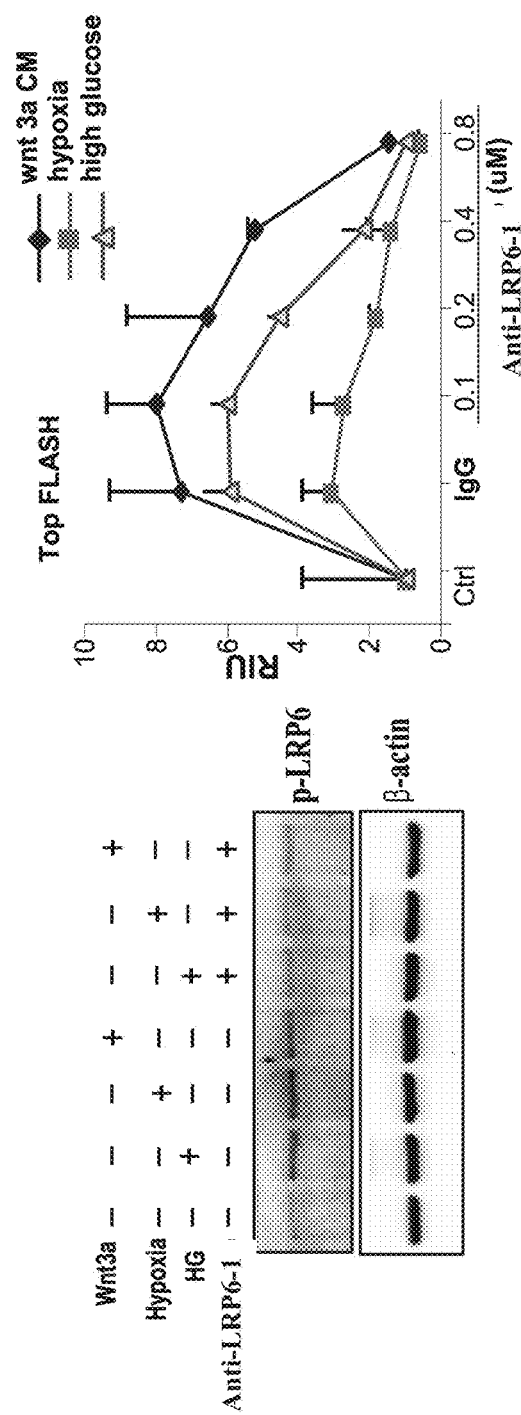
FIG. 8 illustrates that Anti-LRP6-1 mAb inhibits Wnt signaling pathway activation. RCEC cells were pretreated without and with Anti-LRP6-1 for 10 minutes, and different concentration of Dkk1 were also used for positive control. After pretreatment with Anti-LRP6-1 or Dkk1, RCECs were separately distributed to three different groups exposed to Wnt3a-containing medium, hypoxia, or high glucose, respectively. Left panel: Western blotting analysis demonstrated that LRP6 phosphorylation was inhibited. Right panel: TOPflash analysis of β-catenin showed that Anti-LRP6-1 essentially completely inhibited β-catenin accumulation.

Anti-LRP6-1 mAb inhibits Wnt signaling pathway activation: Since LRP6 activation is the key step for Wnt signaling pathways, causing core effector β-catenin accumulation, the ability of Anti-LRP6-1 to inhibit Wnt signaling downstream from β-catenin accumulation was also assessed. RCEC cells were pretreated with and without Anti-LRP6-1 for 10 minutes, and then separately distributed to three different groups that were exposed to Wnt3a-containing medium, hypoxia, or high glucose, respectively. The data presented in FIG. 8 demonstrate that Anti-LRP6-1 essentially completely inhibited said stimulation.

Figure 9:
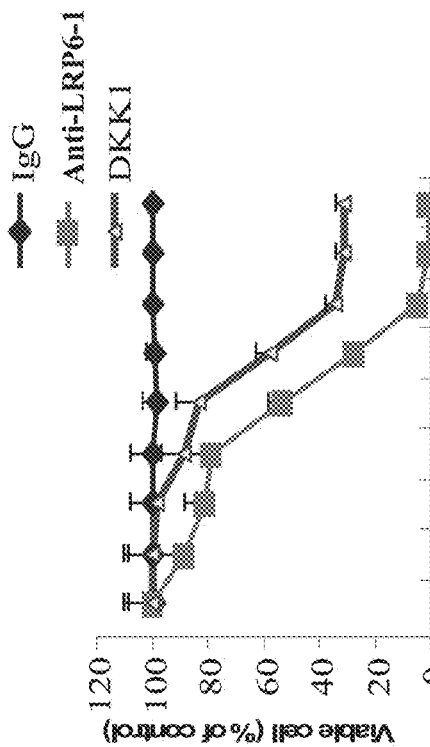
FIG. 9 graphically depicts that Anti-LRP6-1 inhibited proliferation of endothelial cells. RCECs were seeded in 96-well tissue culture plates, and [$^{14}$C]thymidine was added to the cells and mixed with different concentrations of Anti-LRP6-1 or DKK1. RCECs were then exposed to 1% $O_2$ for 3 days, and the radioactivity incorporated into the cell monolayer was determined and the percentage inhibition of the maximal signal was calculated.

Anti-LRP6-1 mAb inhibits endothelial cells' proliferation: The Wnt signaling pathway has been implicated in angiogenesis; hence, $[^{14}C]$thymidine incorporation into RCEC DNA was measured as a model for inhibition of endothelial cell proliferation and survival. A scintillation proximity assay was used to measure $[^{14}C]$thymidine incorporation into RCECs. RCECs were plated on 96-well scintillant plates, and 48 hours later $[^{14}C]$thymidine was added to the cells and mixed with different concentrations of Anti-LRP6-1 or DKK1. RCECs were then exposed to 1% $O_2$ for 3 days, and the radioactivity incorporated into the cell monolayer was determined and the percentage inhibition of the maximal signal was calculated. The results demonstrated that thymidine incorporation was inhibited by Anti-LRP6-1; the $IC_{50}$ values span a broad range (0.5-2 µmol/L). However, compared with Dkk1, Anti-LRP6-1 has a more potent inhibitory effect on the proliferation of endothelial cells (FIG. 9).

Figure 10:
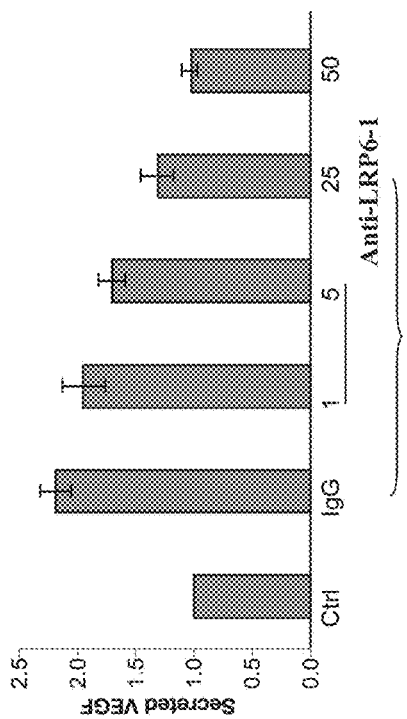
FIG. 10 graphically depicts that Anti-LRP6-1 decreased VEGF over-expression. RCECs were pretreated with Anti-LRP6-1 for 10 minutes, and exposed to hypoxia for 24 hours. The VEGF levels in the culture medium were measured using ELISA. Anti-LRP6-1 significantly decreased VEGF over-expressed in the endothelial cells that were exposed to hypoxic conditions.

Anti-LRP6-1 mAb decreases VEGF over-expression: The biological effects of Anti-LRP6-1 on VEGF over-expression were also measured. RCECs were pretreated with Anti-LRP6-1 for 10 min, and then exposed to hypoxia for 24 hours. The VEGF levels in the culture medium were measured using an ELISA kit (R&D Systems, Inc., MN) following the manufacturer's protocol. The results demonstrated that Anti-LRP6-1 significantly decreased VEGF over-expressed in the endothelial cells exposed to hypoxia conditions. Similar results were obtained in several additional experiments (FIG. 10).

Figure 11:
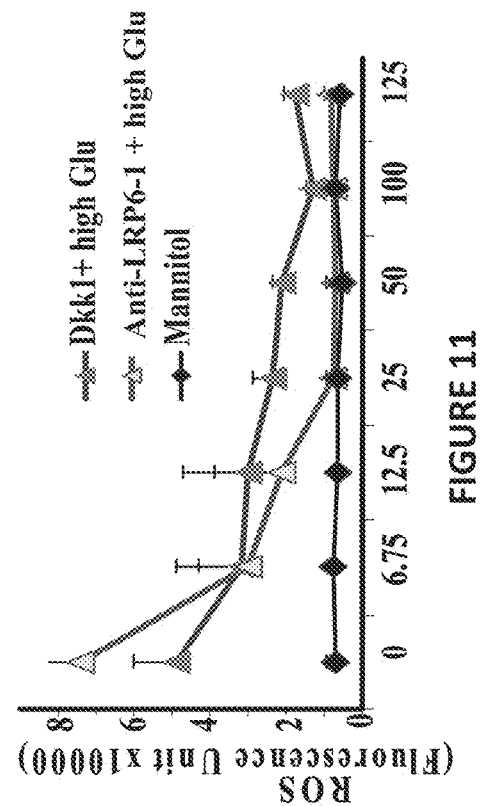
FIG. 11 graphically depicts a comparison of the effects of Dkk1 and Anti-LRP6-1 on ROS generation induced by high glucose. RCEC were exposed to 30 mM glucose in the absence or presence of various concentrations of DKK1 (6.25-100 nM) and Anti-LRP6-1 for 2 h. Intracellular ROS generation was measured using CM-H$_2$DCFDA, and expressed as fluorescent unit per well (means±SD, n=3).

Anti-LRP6-1 attenuates the generation of reactive oxygen species (ROS) induced by high glucose: RCEC were exposed to 30 mM glucose in the absence or presence of various concentrations of Anti-LRP6-1 or DKK1 (6.25-125 nM) for 2 hours. As shown by the intracellular ROS generation assay, high glucose induced the generation of ROS. Both Anti-LRP6-1 and DKK1 blocked ROS generation. However, Anti-LRP6-1 has a more potent inhibitory effect than that of Dkk1, and in a concentration-dependent manner (FIG. 11).

Figure 12:
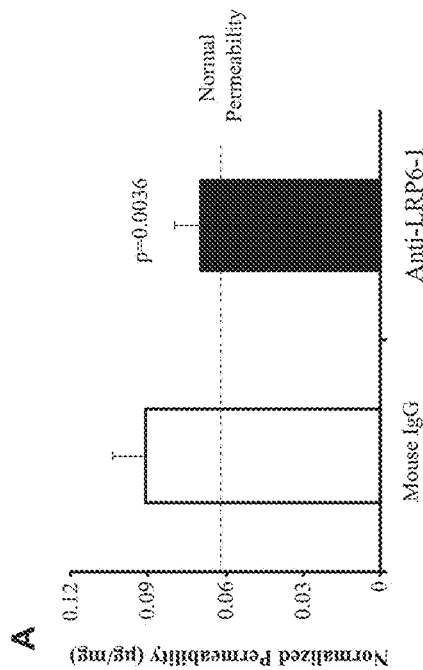
FIG. 12 comprises photomicrographs that demonstrate that Anti-LRP6-1 attenuates retinal vascular leukostasis in diabetic rats. STZ diabetic rats at 2 weeks after the onset of diabetes received an intravitreal injection of 5 μM/eye of Anti-LRP6-1 in the treatment group and the same dose of Control mouse IgG and Dkk1 in the control group. 4 weeks after the injection, retinal vascular leukostasis was performed. The retinal vasculature and adherent leukocytes were stained by FITC-conjugated concanavalin A. A-D: Retinal vasculature and adherent leukocytes in non-diabetic rats (A), STZ-induced diabetic rats with IgG (B), STZ-induced diabetic rats injected with Dkk1 (C), and Anti-LRP6-1 (D).

Anti-LRP6-1 mAb attenuates retinal vascular leukostasis in the diabetic rats: STZ diabetic rats at 2 weeks after the onset of diabetes received an intravitreal injection of 5 µg/eye of Anti-LRP6-1 in the treatment group and the same dose of Control mouse IgG and Dkk1 in the control group. Four weeks after the injection, the animals were perfused to remove circulating leukocytes. The retinal vasculature and adherent leukocytes were stained by FITC-conjugated concanavalin A (FIG. 12).

Figure 13:
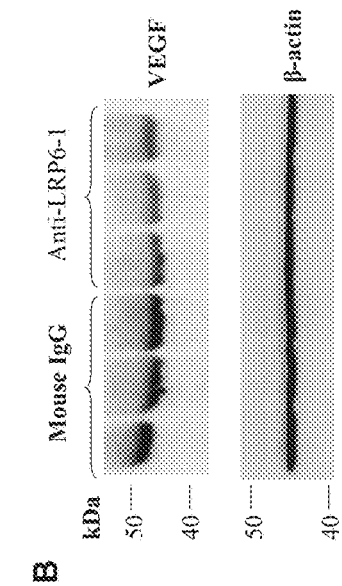
FIG. 13 illustrates the effect of the Anti-LRP6-1 on ischemia-induced retinal vascular leakage and VEGF over-expression. The Anti-LRP6-1 was injected intravitreally (10 μg/eye) into the OIR rats at P12. (A) Vascular permeability was measured at P16 using Evans blue method and normalized by total retinal protein concentration (mean±SD, n=4). (B) The same amount of total retinal proteins (50 μg/rat) was immunoblotted with an antibody for VEGF and normalized by β-actin levels.

Anti-LRP6-1 mAb attenuates ischemia-induced VEGF over-expression in the retina and reduced retinal vascular leakage: Oxygen-induced retinopathy (OIR) is commonly used as a model of DR as it develops both retinal vascular leakage and NV. New born brown Norway rats were exposed to 75% oxygen at the postnatal age of Days 7 to 12 (P7-P12). Anti-LRP6-1 was injected into the vitreous at P12, with the same amount of non-specific mouse IgG for control. Retinal vascular permeability was measured using the Evans blue albumin leakage method. Evans blue-albumin complex leaked into the retina was quantified using a spectrophotometer and normalized by total retinal protein concentration. The results showed that the Anti-LRP6-1 significantly reduced retinal vascular leakage, compared to the IgG control (FIG. 13A). Since VEGF is known as a major factor for NV and vascular leakage, VEGF levels in the retina were also measured. As shown by Western blot analysis, retinal VEGF levels were significantly reduced by Anti-LRP6-1 in OIR rats, compared to those in the IgG-injected OIR rats (FIG. 13B).

Anti-LRP6-1 mAb reduces retinal vascular leakage in diabetic rats: Example 1 showed that the Wnt pathway is also activated in the retina of STZ-induced diabetic rats. To evaluate the efficacy of Anti-LRP6-1, said mAb was injected into the vitreous of STZ-diabetic rats, 2 weeks after the onset of diabetes. Retinal vascular leakage was measured 3 weeks after the mAb injection using Evans blue method. The results showed that the rats injected with the mAb had significantly lower retinal vascular leakage compared to those injected with non-specific IgG control (FIG. 14), demonstrating that Anti-LRP6-1 reduced retinal vascular leakage induced by diabetes, and therefore Anti-LRP6-1 has a therapeutic effect on DME.

Figure 14:
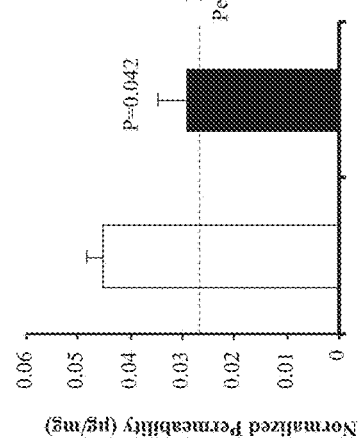
FIG. 14 graphically depicts the effect of the Anti-LRP6-1 on AMD. Anti-LRP6-1 was injected intravitreally (10 μg/eye) into Vldlr$^{-/-}$ mice. Retinal vascular permeability was measured 2 weeks after the injection with Evans blue method and normalized by total retinal protein concentration (mean±SD, n=4).

Anti-LRP6-1 reduces retinal vascular leakage in an AMD model: $Vldlr^{-/-}$ mice are well accepted as a genetic model of wet AMD since they develop sub-retinal NV, retina vascular leakage and inflammation. To evaluate the efficacy of Anti-LRP6-1 on AMD, said mAb was injected into the vitreous of adult $Vldlr^{-/-}$ mice with the non-specific IgG as a control. Two weeks after the injection, a permeability assay demonstrated that the eye injected with Anti-LRP6-1 had significantly lower retinal vascular leakage, compared to the IgG control (FIG. 14). This result further demonstrates that Anti-LRP6-1 has a therapeutic effect on AMD.

Example 3

Diabetic retinopathy, a leading cause of blindness, is a severe ocular complication involving progressive retinal vascular leakage, neovascularization (NV), and retinal detachment in both type 1 and type 2 diabetes. Multiple growth factors, such as vascular endothelial growth factor (VEGF), play important roles in retinal vascular abnormalities in diabetic retinopathy.

Retinal inflammation in hyperglycemia condition with oxidative stress is believed to play a crucial role in the development of diabetic retinopathy. It has been shown that levels of soluble inter-cellular adhesion molecule-1 (ICAM-1) and vascular cell adhesion molecule-1 (VCAM-1), which mediate leukocyte adhesion to the endothelium, were significantly increased in the vitreous and serum of diabetic patients. Although numerous observations underscored the association of hyperglycemia with inflammation in diabetic retinopathy, the pathogenic mechanism leading to chronic inflammation in diabetic retinopathy was unclear. Recently, the pathogenic role of canonical Wnt signaling in retinal inflammation in diabetic retinopathy has been established.

Wnts, a group of secreted cysteine-rich glycoproteins, initiate a signaling cascade by binding to a receptor complex consisting of Frizzled (Fz) receptor and low-density lipoprotein receptor-related protein 5/6 (LRP5/6). Upon Wnt ligand binding, C-terminus conserved motifs (PPPS/TP) of LRP6 are phosphorylated in an orderly fashion by CK1 and GSK3β which are recruited to the membrane via scaffold protein Axin. The successive phosphorylation of PPPS/TP motifs reduces cytosolic kinase pool, and results in cytosolic β-catenin stabilization and accumulation. Then, β-catenin is translocated into the nucleus, and associates with TCF/LEF to activate target gene expression including VEGF, ICAM-1 and tumor necrosis factor-α (TNF-α).

Example 1 showed that retinal levels of β-catenin are increased in humans with diabetic retinopathy and in diabetic retinopathy animal models. Retinal levels of LRP6 were also increased in the retina of diabetic retinopathy models. In addition, an intravitreal injection of a Wnt antagonist Dickkopf homolog 1 (DKK1) effectively ameliorated diabetic retinopathy in animal models, indicating a key role of the dysregulation of the Wnt pathway in the pathogenesis of diabetic retinopathy. Furthermore, activation of Wnt signaling alone in the retina of normal rats is sufficient to induce pathological changes such as retinal inflammation and vascular leakage. Recent evidence also indicated that Wnt signaling is directly linked to the inflammatory responses in general, as it was documented that Wnt signaling activates nuclear factor κB (NF-κB) and up-regulates expression of a number of inflammatory factors including signal transducer and activator of transcription 3 (STAT-3). Together, these previous findings indicate that over-activation of the Wnt pathway plays a pathogenic role in diabetic retinopathy and represents a promising drug target for the treatment of diabetic retinopathy.

The Wnt co-receptor LRP6 plays a pivotal role in the Wnt signaling activation. It provides binding sites for both Wnt ligands and antagonist DKK1 on its ectodomain. Moreover, its conserved intracellular PPPS/TP motifs are essential docking sites for protein complex Axin/GSK3β for signal amplification, which is sufficient to transmit signals from Wnt ligands to the intracellular cascade. These facts indicate that LRP6 represents an ideal target for blocking the Wnt pathway.

Numerous pharmaceutical antibodies have been reported to not only target specific oncogenic receptors such as epidermal growth factor receptor, but also to neutralize soluble proteins such as VEGF in multiple disease models. To assess the impact of blockade of LRP6 on the Wnt signaling pathway activity and retinal inflammation in diabetic retinopathy, a monoclonal antibody specific for the extracellular domain of LRP6 including the first and second propeller domains was generated. Its inhibitory effects on the canonical Wnt pathway and its beneficial effects on diabetic retinopathy were further evaluated using diabetic models.

Materials and Methods of Example 3

Plasmids, antibodies, and reagents: The plasmids expressing the full-length LRP6, ectodomain of LRP6 (LRP6N), ectodomain of LRP5 (LRP5N), and ectodomain of low-density lipoprotein receptor (LDLRN) were kind gifts from Dr. X. He at Harvard University. The human cDNA of deletion mutants of LRP6, LRP6E1E2 and LRP6E3E4, were amplified by polymerase chain reaction and tranferred into pET28b+ plasmid for expression in BL21(DE3). Human full-length LRP5 and VLDLR-N were subcloned into pGEMT-easy vector and then pcDNA3.1(−) and pcDNA6 plasmids, respectively, for expression in mammalian cells. The human Wnt1 cDNA was PCR-amplified and cloned into pcDNA6 plasmid for expression.

Mouse anti-β-actin antibody, rabbit anti-TNF-α antibody (Abcam, Cambridge, Mass.), mouse anti-VEGF antibody, goat anti-ICAM-1 antibody, rabbit anti-β-catenin antibody (Santa Cruz Biotechnologies, Santa Cruz, Calif.), rabbit anti-pLRP6 (at Ser1490) antibody, rabbit anti-p-β-catenin (Ser33/37/Thr41) antibody (Cell Signaling, Danvers, Mass.) were used for Western blot analysis. Monoclonal antibody Anti-LRP6-1 was purified using protein G column (Thermo Fisher Scientific Inc., Waltham, Mass.) following manufacturer's instruction.

D-glucose, lithium chloride, sodium chloride were purchased from Sigma-Aldrich Inc. (St. Louis, Mo.). Non-specific mouse IgG was purchased from Vector laboratories (Burlingame, Calif.).

Cell culture, transfection, and antibody treatment: hTERT-RPE (ATCC, Manassas, Va.), rat Müller (rMC-1; a kind gift from Dr. Vijay Sarthy at Northwestern University), and bovine retinal capillary endothelial cells (RCECs) were maintained in Dulbecco's modified Eagle's medium (DMEM; Cellgro, Manassas, Va.) supplemented with 10% FBS (Invitrogen, Carlsbad, Calif.). Mouse L cells stably expressing Wnt3A were maintained in DMEM supplemented with 10% calf FBS, and Wnt3A conditioned media (WCM) were used as a source of Wnt ligand. Lipofectamine 2000 (Invitrogen, Carlsbad, Calif.) was used for the transfection of TOP FALSH promoter constructs and expression plasmids following the protocol recommended by the manufacturer. Cells were synchronized in serum-free media for 3 hours, and were treated with different concentrations of Anti-LRP6-1 for 0.5 hour, supplemented with non-specific mouse IgG to the equal concentrations of total IgG in each well. Then, the cells were treated with 20% WCM or 30 mM D-glucose to activate Wnt signaling.

Conditioned media containing VLDLRN with a 6× histidine tag (VLDLRN-his), LDLRN with a myc tag (LDLRN-myc), LRP5N-myc and LRP6-myc were obtained following the procedures. HEK-293T cells at 60% confluency were transiently transfected with expression plasmids using lipofectamine 2000 (Invitrogen, Carlsbad, Calif.), and culture media were collected after 48 hours incubation. The media were filtered and used as a conditioned media (CM).

Antigen preparation, monoclonal antibody selection, and purification: LRP6E1E2 and LRP6E3E4 were subcloned into pGEMT-easy vector by polymerase chain reaction from human origin cDNA, and transferred to pET28b+ plasmid. Then, pET28b+ containing LRP6E1E2 and LRP6E3E4 sequences were transformed into BL21(DE3) for expression. The inclusion body was purified and then dissolved in a buffer containing 6 M guanidine hydrochloride. The denatured proteins were purified using Ni-NTA resin (Novagen, Madison, Wis.) following manufacturer's instruction. Purified antigens were confirmed by Coomassie blue staining and Western blot analysis with an anti-His tag antibody.

On-column refolding was performed by serial buffer changes. Ten column volumes (CV) of buffer A (0.1% Triton X-100, GSH/GSSG in PBS, pH 7.8), 10 CV of buffer B (5 mM beta-cyclodextrin, GSH/GSSG in PBS, pH 7.8), and washing buffer (20 mM imidazole in PBS, pH 7.8) were serially used for refolding. The protein was eluted with 300 mM imidazole in phosphate buffered saline (PBS). The eluates were dialyzed in PBS, and protein concentration was measured by Bradford assay.

Monoclonal antibodies for LRP6 ectodomain were generated via a contracted service by Proteintech Group (Chicago, Ill.) using the purified antigen. Among various positive clones screened out from ELISA, Anti-LRP6-1 was identified to be specific and to have blocking activity, by specificity tests using ELISA and Western blot analysis.

Anti-LRP6-1 used in cell culture and intra-vitreal injection was produced and purified following the conventional methods (Hendriksen et al., Res immunol, 149:535-542 (1998)). Briefly, 6 wks-old female BALB/C mouse abdominal cavity was injected with hybridoma cells (1×106/ml) and ascites were collected after 7 days post-injection. The collected mouse ascites were applied onto a protein G column following manufacturer's protocol. The mAb eluates from the column were dialyzed against PBS overnight.

Luciferase reporter assays: hTERT-RPE cells, plated at $2 \times 10^4$ cells/well in 24-well plates, were transfected with 0.25 μg TOPFlash and 0.05 μg pRL-TK constructs using lipofectamine 2000. Four hours post-transfection, the culture media was replaced by fresh media and the cells were pre-treated with Anti-LRP6-1, with supplemented amount of control IgG to reach the same concentration of total IgG in each well, for 0.5 hours and then Wnt3A CM was added for 16 hours. For the analysis using Wnt1, expression plasmid of Wnt1 was transfected with promoter constructs, and followed by the same procedures. Luciferase activity measurement was performed using dual luciferase assay kit (Promega, Madison, Wis.) following the manufacturers' protocols. Renilla luciferase activity was measured to normalize transfection efficiency. All experiments were performed at least in triplicate.

Western blotting: Cultured cells were washed with cold phosphate buffered saline (PBS) and lysed in cell lysis buffer (150 mM NaCl, 1% NP-40, 0.5% deoxycholate, 0.1% SDS, 50 mM Tris, pH 8.0, 10 mM sodium pyrophosphate, 100 mM sodium fluoride, and 2 mM phenylmethylsulfonyl fluoride). After washing with PBS, the cells were suspended in PBS with a protease inhibitor cocktail (Roche Applied Science, Indianapolis, Ind.) and two times of freeze/thaw cycles were performed to isolate the cytosolic fraction. The same amounts of retinal proteins from each animal were obtained following sonication in the lysis buffer (same as above) and used for Western blot analysis after total protein concentration measurement by Bradford assay. Further, specific primary antibodies for each protein were incubated overnight and HRP-conjugated secondary antibody was used for detection. The signal was developed with a chemiluminescence detection kit (ECL; Amersham International, Piscataway, N.J.). Blots were then stripped and re-blotted with an antibody specific for β-actin for loading control. Images were captured by a Chemi Genius Image Station (SynGene, Frederick, Md.). Individual protein band was semiquantified by densitometry using the GENETOOLS program (SynGene, Frederick, Md.).

Immunohistochemistry: Immunostaining was performed as described previously (Zhang et al., Am J Pathol, 166: 313-321 (2005)). Briefly, the eyes were cross-sectioned sagittally through the center of the cornea and optic nerve head, and both halves of the eyeball were embedded with the center facing down. Serial cryosections (5 μm thickness) were blocked with 1% BSA in PBS and incubated with FITC-conjugated Anti-LRP6-1, with FITC-IgG as a control. For negative control, FITC-Anti-LRP6-1 was pre-adsorbed with antigen, LRP6E1E2 peptide, to demonstrate the specificity the antibody staining. After PBS-0.1% tween-20 washes, the slides were then rinsed in PBS and viewed under a fluorescence microscope.

Rat models of OIR and STZ-induced diabetes. All of the animal experiments were performed in compliance with the ARVO Statement for the Use of Animals in Ophthalmic and Vision Research. Brown Norway rats (Charles River Laboratories, Wilmington, Mass.) were used for the OIR model following an established protocol (Ricci, Doc Opthalmol, 74:171-177 (1990)). Diabetes was induced and monitored in adult Brown Norway rats by an intraperitoneal injection of STZ (55 mg/kg in 10 mmol/L of citrate buffer, pH 4.5) as described previously (Zhang et al., Am J Pathol, 166:313-321 (2005)). Diabetic rats at 2 weeks after the onset of diabetes received an intravitreal injection of Control IgG or Anti-LRP6-1.

Intravitreal injection: Animals were anesthetized with a 50:50 mix of ketamine (100 mg/mL) and xylazine (20 mg/mL), and pupils were dilated with topical application of phenylephrine (2.5%) and tropicamide (1%). A sclerotomy was created approximately 1 mm posterior to the limbus with a needle (~32 gauge). A glass injector (33 gauge) connected to a syringe filled with 2 μL of LRP6 mAb with desired concentrations or purified mouse IgG was introduced through the sclerotomy into the vitreous cavity.

Retinal vascular permeability assay: Retinal vascular permeability was measured using Evans blue-albumin as tracer following an established protocol (Aiello et al., Am J Opthalmol, 132:760-776 (2001)). Concentrations of Evans blue in the retina were normalized by total retinal protein concentrations and by Evans blue concentrations in the plasma.

Leukostasis assay: The assay was performed as described previously (Chen et al., Microvasc Res, 78:119-127 (2009)). Briefly, mice were anesthetized and perfused through the left ventricle with PBS to remove circulating leukocytes in blood vessels. The adherent leukocytes in the vasculature were stained by perfusion with FITC-conjugated concanavalin-A (Con-A, 40 μg/ml, Vector Laboratories, Burlingame, Calif.). The eyes were removed and fixed in 4% paraformaldehyde. The retinas were dissected and flat-mounted. Adherent leukocytes in the retinal vasculature were counted under a fluorescence microscope.

Statistical analysis: The quantitative data were analyzed and compared using Student's t test. Statistical significance was set at $p<0.05$.

Results of Example 3

Figure 15:
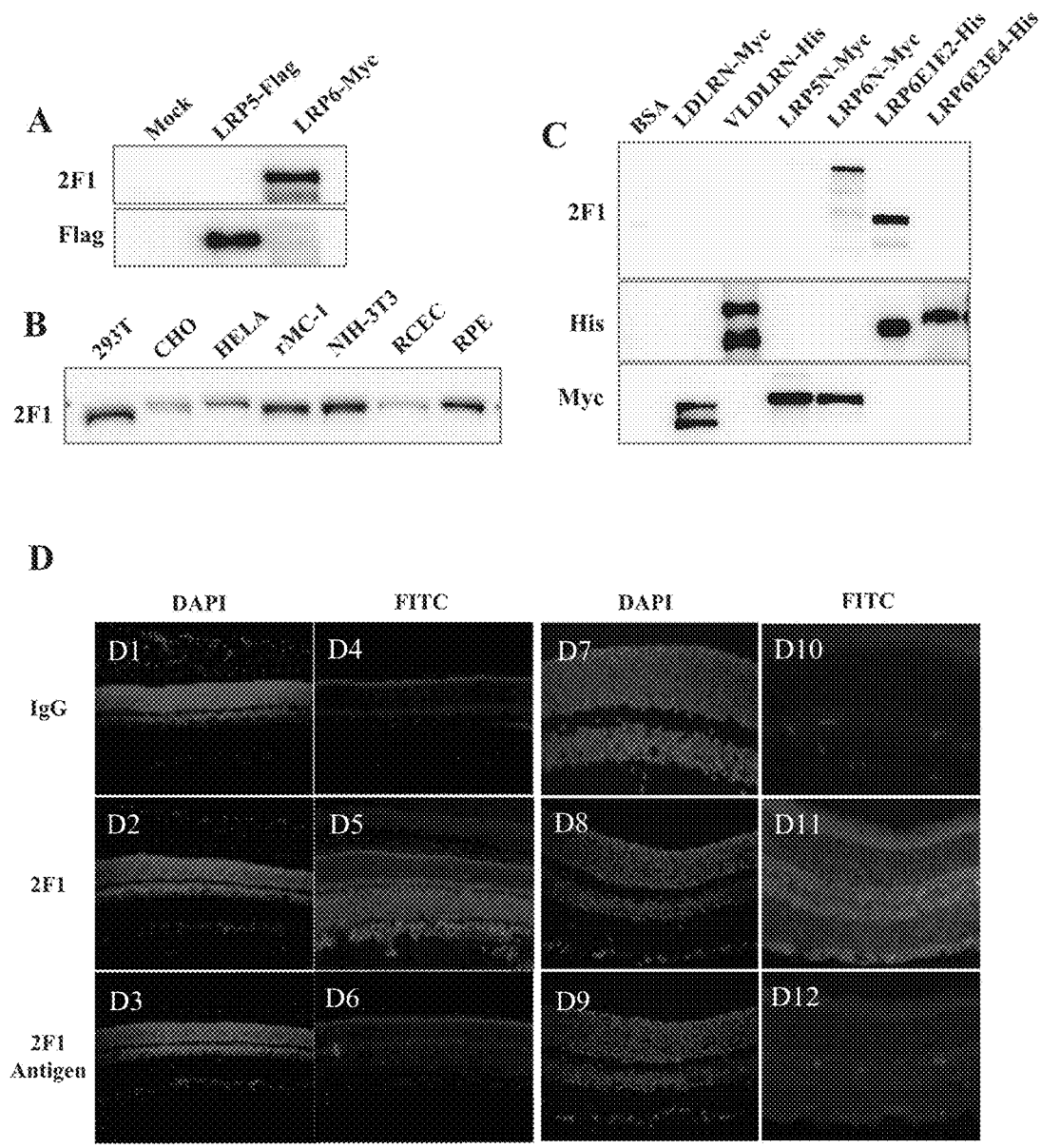
FIG. 15 illustrates specificity of Anti-LRP6-1 on LRP6 ectodomain. A: HEK-293T cells were separately transfected with plasmids expressing LRP5-Flag and LRP6-Myc, with an empty vector as control. Forty-eight hours post-transfection, total cell lysates (50 μg) were applied for Western blot analysis using Anti-LRP6-1 and an anti-Flag antibody (M2). B: The ability of Anti-LRP6-1 to recognize endogenous LRP6 in different species. Total cell lysates (50 μg) from each cell line were applied for Western blot analysis using Anti-LRP6-1. C: Conditioned media containing LDLRN-Myc, LRP5N-Myc and LRP6N-Myc, and purified recombinant peptides of VLDLR-N-His, LRP6E1E2-His and LRP6E3E4-His were loaded for Western blot analysis using Anti-LRP6-1, anti-His and anti-Myc antibodies. D: Immuno-localization of LRP6 in the retinal cryosections. FITC-labeled Anti-LRP6-1 was used to determine the cellular localization of LRP6 in the retinas of rats (D1-D6) and mice (D7-D12). Non-specific mouse IgG was labeled with FITC and used as a negative control (D1, D4, D7, D10). The sections were stained with FITC-Anti-LRP6-1 (D2, D5, D8, D11). FITC-Anti-LRP6-1 pre-absorbed with 10 μg/ml purified LRP6E1E2-His antigen was used for staining to confirm the specificity of the immunosignals of LRP6 (D3, D6, D9, D12).

Specificity of Anti-LRP6-1 for LRP6 E1E2 domain: A number of clones of mAb were raised using the recombinant ectodomain of LRP6. Out of numerous positive clones of mAb, Anti-LRP6-1 was selected based on its specificity for endogenous LRP6 in various cell lines. Anti-LRP6-1 recognized LRP6 as a single band, but not LRP5, the other Wnt co-receptor with 71% amino acid sequence identity to LRP6 in the human. Furthermore, Anti-LRP6-1 recognized endogenous LRP6 in various cell lines from different species including the human, mouse, rat and bovine (FIG. 15A-B). As LRP6 belongs to the low-density lipoprotein receptor (LDLR) family, the possible binding of Anti-LRP6-1 to other members of the LDLR family such as LDLR and very low-density lipoprotein receptor (VLDLR) was evaluated (FIG. 15C). Western blot analysis showed that Anti-LRP6-1 did not recognize LDLR or VLDLR, indicating its specificity for LRP6. Furthermore, it was confirmed that Anti-LRP6-1 recognized the full-length ectodomain and the E1E2 fragment of LRP6, but not the E3E4 domain, indicating that the epitope of Anti-LRP6-1 is present in the E1E2 domain of LRP6 (FIG. 15C).

Next, rat and mouse retinal sections were immunostained with FITC-labeled Anti-LRP6-1 to determine spatial expression of LRP6 in the retina. The immunohistochemistry using FITC-Anti-LRP6-1 showed that LRP6 is primarily expressed in the inner retina in rats. In the mouse retina, however, intensive LRP6 signal was observed in the inner retina as well as in the RPE (FIG. 15C). Immunostaining with the isotype control (non-specific IgG) (D1, D4, D7, D10) and FITC-Anti-LRP6-1 pre-absorbed by antigen (LRP6 ectodomain peptide) (D3, D6, D9, D12) under the same conditions did not show specific signals, indicating that the LRP6 signals are specific.

Figure 16:
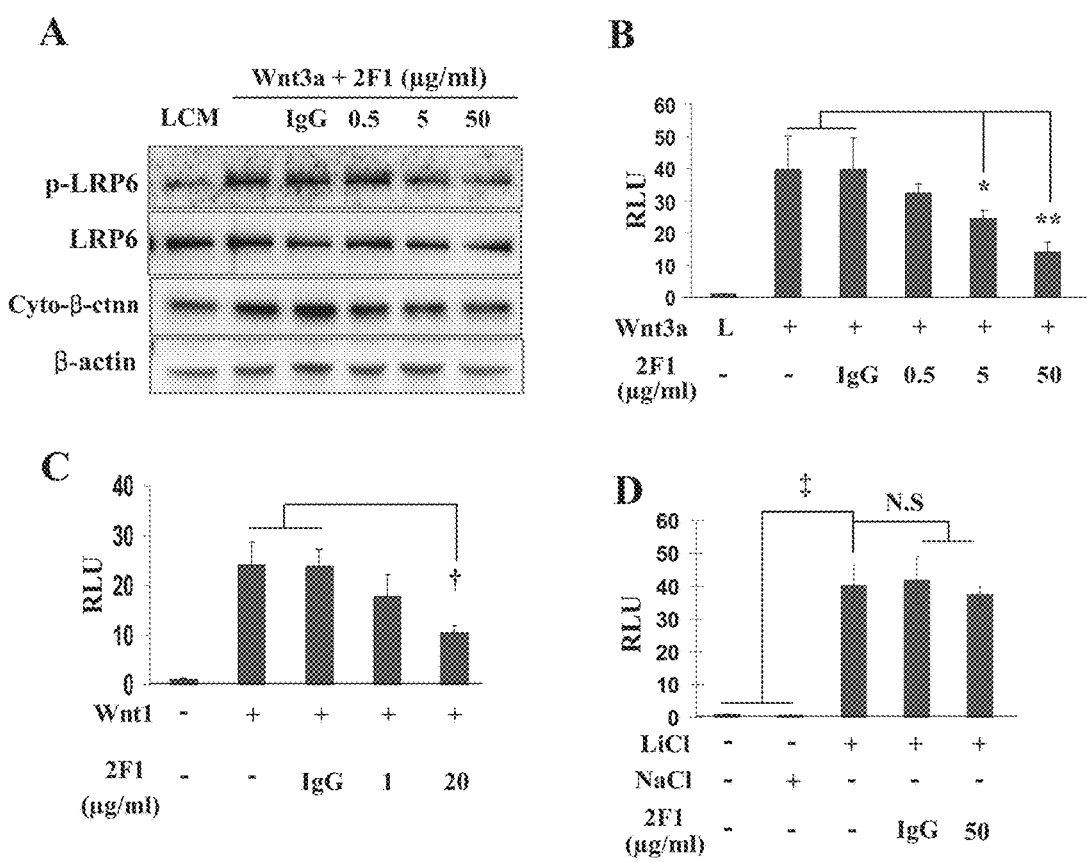
FIG. 16 depicts the inhibitory effect of the Anti-LRP6-1 on the Wnt signaling at the level of receptor-ligand interaction. A: hTERT-RPE cells at 70% confluence were serum-starved for 3 hours prior to Wnt signaling activation. Each well was pre-incubated for 30 minutes with 0, 0.5, 5 and 50 μg/ml of Anti-LRP6-1; non-specific mouse IgG was supplemented to reach total IgG concentrations to 50 μg/l in every well. Then, 25% Wnt3A conditioned media (Wnt3A) were added to the culture medium with L cell CM (L) as a control. After 2 hours stimulation, equal amount of cell lysates (50 μg) were subjected to Western blot analysis using antibodies for phosphorylated LRP6 (p-LRP6) (Ser1490) and for total LRP6. Cytosolic proteins (20 μg) were isolated and blotted with an antibody for cytosolic β-catenin (cyto-β-ctnn). B: hTERT-RPE cells were transfected with TOPFLASH and control pRL-TK plasmids. The cells were exposed to 25% WCM (Wnt3A) with various concentrations of Anti-LRP6-1 for 16 hours, and then TCF/β-catenin activity was measured using dual-luciferase assay and expressed as relative luciferase unit (RLU) (mean±SD, n=4, *P<0.05, **P<0.01). C: hTERT-RPE cells were transfected with TOPFLASH vectors and a Wnt1 expression plasmid. The vector without insert was used as a control. At 4 hours post-transfection, cells were treated with Anti-LRP6-1 at the indicated concentrations for 16 hours, and then luciferase activity was measured (mean±SD, n=4, †P<0.001). D: The cells were exposed to 25 mM LiCl to activate Wnt signaling, with NaCl as control. Equal amount of non-specific IgG or Anti-LRP6-1 (50 μg/ml) were added to the cells and incubated for 16 hours, and Luciferase activity was measured (mean±SD, n=4, ‡P<0.0001, N.S: not statistically significant).

Anti-LRP6-1 efficiently inhibited Wnt ligand-induced Wnt signaling at the receptor level. To reveal if Anti-LRP6-1 has an inhibitory effect on the canonical Wnt pathway, hTERT-RPE, a cell line derived from human retinal pigment epithelial (RPE) cells and expressing endogenous LRP6, was exposed to Wnt3A conditioned media or was transfected with Wnt1 to activate the canonical Wnt pathway. Anti-LRP6-1 efficiently inhibited Wnt3A-mediated phosphorylation of LRP6 on residue Serine1490, an early step in Wnt pathway activation, while having no effect on total LRP6 levels. Anti-LRP6-1 also attenuated the Wnt ligand-induced increase of cytosolic β-catenin levels, indicating attenuation of β-catenin accumulation. In contrast, negative control IgG had no effect on pLRP6 and cytosolic-β-catenin levels (FIG. 16A). The effect of Anti-LRP6-1 on transcriptional activity of TCF/β-catenin was evaluated using TOP-FLASH activity assay which measures Luciferase activity driven by a promoter containing TCF/β-catenin-binding sites. Wnt3A induced Luciferase activity by 40 folds, and the Anti-LRP6-1 suppressed the Wnt3A-induced Luciferase activity in a dose-dependent manner with EC50 approximately 20 μg/ml. Similarly, Anti-LRP6-1 also inhibited the Wnt1-induced TOPFLASH activity with EC50 approximately 20 μg/ml (FIG. 16C).

Lithium chloride (LiCl) is a known inhibitor of GSK3β that constitutively phosphorylates β-catenin, which mediates proteasomal degradation of β-catenin. Thus, lithium activates canonical Wnt signaling independent of Wnt ligands, Wnt receptors and co-receptors. As shown by TOP-FLASH assay, 25 mmol/L LiCl induced TCF/β-catenin activity markedly. Anti-LRP6-1 did not inhibit lithium-induced TOPFLASH activity, indicating the inhibition by Anti-LRP6-1 is at the level of receptor-ligand interactions (FIG. 16D).

Figure 17:
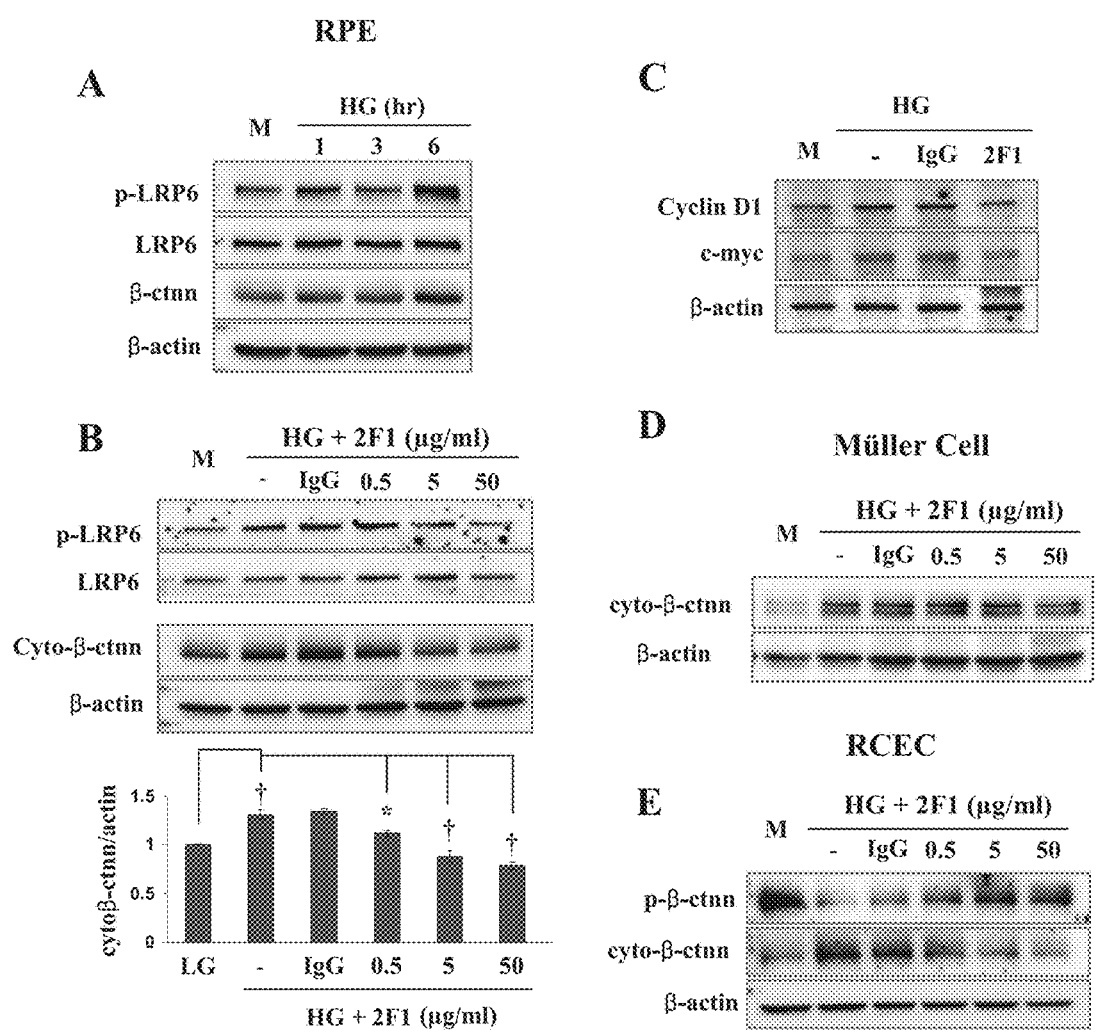
FIG. 17 illustrates the inhibitory effect of the Anti-LRP6-1 on high glucose-induced canonical Wnt signaling. Retinal cells were exposed to high glucose media using 30 mmol/L D-glucose (HG) with 5 mmol/L D-glucose and 25 mmol/L mannitol (M) for osmotic control. A: hTERT-RPE cells were exposed to HG for different durations. Total cell lysates were used to measure the levels of p-LRP6, total LRP6, and β-catenin. B: hTERT-RPE cells were exposed to high glucose for 6 hours with different concentrations of Anti-LRP6-1. Total cell lysates were used for Western blot analysis to measure p-LRP6 and total LRP6; the cytosolic fraction was used for measurement of cytosolic β-catenin (Cyto-β-ctnn). Levels of cytosolic β-catenin from four independent Western blot analysis were quantified by densitometry and normalized by β-actin levels (mean±SD, n=4, *P<0.05, †P<0.001). C: hTERT-RPE cells were exposed to high glucose for 24 hours with 50 μg/ml Anti-LRP6-1 or IgG, followed by Western blot analysis using antibodies specific for Cyclin D1 and c-myc. D & E: A Muller cell line (rMC-1)

Anti-LRP6-1 inhibited high-glucose (25 mM)-activated canonical Wnt signaling. It has been documented that the canonical Wnt pathway is activated in the retinae of diabetic patients and animal models, and high glucose medium also activates Wnt signaling in the cultured cells. Retinal cells relevant to the pathogenesis of diabetic retinopathy, including RPE, Müller and endothelial cells, were exposed to a high glucose medium (30 mM) to activate the Wnt pathway, with low glucose medium (5 mM glucose and 25 mM mannitol) as control. Anti-LRP6-1 was added to the medium to determine its inhibitory effect on high glucose-induced Wnt signaling. Western blot analysis showed that high glucose exposure for 6 hours increased p-LRP6 and β-catenin levels in the RPE cells. Anti-LRP6-1 sufficiently attenuated the high glucose-induced increases of p-LRP6 and β-catenin accumulation in a concentration-dependent manner (FIG. 17A-B). To further confirm the activation of Wnt signaling, expression levels of Wnt target genes such as cyclin D1 and c-myc were measured. High glucose medium up-regulated expression of cyclin D1 and c-myc as shown by Western blot analysis; however, Anti-LRP6-1 attenuated the levels of cyclin D1 and c-myc (FIG. 17C).

Retinal Müller cells are known to play a key role in retinal inflammation in diabetic retinopathy. In Müller cells, Anti-LRP6-1 also attenuated the high glucose-induced increase of cytosolic β-catenin levels (FIG. 17D). As retinal endothelial cells are major players in retinal vascular leakage, leukostasis and neovascularization in diabetic retinopathy, bovine retinal capillary endothelial cells (BRCEC) were exposed to the 30 mM D-glucose to activate Wnt signaling. Compared to low glucose control (5 mmol/L glucose and 25 mmol/L mannitol), 30 mM D-glucose increased cytosolic β-catenin, while Anti-LRP6-1 inhibited the increase induced by high glucose in BRCEC. Since phosphorylation of β-catenin by GSK3β (Ser33/37/Thr41) leads to degradation of β-catenin, measured phosphorylated β-catenin levels were also measured. The results showed high glucose significantly decreased p-β-catenin levels, while Anti-LRP6-1 reversed the change induced by high glucose (FIG. 17E).

In summary, these results showed that high glucose activated the Wnt signaling pathway and its target gene expression in retinal cells including RPE, Müller cells, and BRCEC, while Anti-LRP6-1 attenuated the high glucose-induced Wnt signaling in a concentration-dependent fashion.

Anti-LRP6-1 suppressed the high glucose-induced expression of inflammatory and angiogenic factors. Over-expression of angiogenic and inflammatory factors in the retina is known to play pathogenic roles in retinal neovascularization and inflammation in diabetic retinopathy. Many of these inflammatory factors are regulated by Wnt signaling. It has been previously described that VEGF is a direct target regulated by the canonical Wnt signaling. In cultured RPE, Müller cells and BRCEC, high glucose medium induced over-expression of VEGF, while Anti-LRP6-1 blocked the over-expression in a concentration-dependent manner. Similarly, high glucose also induced over-expression of inflammatory factors ICAM-1 and TNF-α. Anti-LRP6-1 suppressed the over-expression of these factors in the retinal cells (FIG. 18). In the same cells, non-specific IgG did not reduce the levels of these factors. Anti-LRP6-1 at high concentrations reduced the levels of VEGF, ICAM-1 and TNF-α to a range of low glucose control (FIG. 18). These results indicate that high glucose induces over-expression of these factors through Wnt signaling.

Anti-LRP6-1 inhibited endothelial cell migration. The effect of Anti-LRP6-1 on endothelial migration was evaluated by scratch wound healing assay and tube formation assay using primary BRCEC, as endothelial cell migration is an important step in retinal neovascularization. The scratch wound healing assay showed that high glucose medium enhanced BRCEC wound healing 48 hours after the scratch. In the presence of Anti-LRP6-1, the high glucose induced BRCEC wound healing was substantially decreased (FIG. 19A-B). In BRCEC tube formation assay, BRCEC formed a tube like pattern in 12 hours, which was attenuated by Anti-LRP6-1, but not by IgG (FIG. 19C-D). Taken together, these results demonstrated that Anti-LRP6-1 inhibited endothelial cell migration.

Anti-LRP6-1 reduced vascular leakage and inhibited inflammation in the retina of OIR model. One of the hallmarks of diabetic retinopathy is a leaky vessel due to breakdown of the blood-retina barrier. OIR rats, a model of proliferative diabetic retinopathy, manifest increased retinal vascular permeability due to ischemia-mediated over-expression of pro-angiogenic factors such as VEGF, a target gene of Wnt signaling. Inhibitory effect of Anti-LRP6-1 on vascular leakage was evaluated in the OIR model. Anti-LRP6-1 was injected intravitreally into the right eye (10 µg/eye) at age P12 and the same amount of control IgG into the contralateral eyes. Retinal vascular leakage was measured using the Evans blue-albumin leakage method at P16, which showed that the eyes injected with Anti-LRP6-1 had significantly lower retinal vascular permeability compared to that injected with control IgG (FIG. 20A). Next, retinal levels of the factors contributing to vascular leakage and inflammation were measured. Compared to control IgG, Anti-LRP6-1 suppressed the expression of ICAM-1, TNF-α, and VEGF in the retina of OIR rats. Anti-LRP6-1 also down-regulated retinal levels of LRP6 and β-catenin, indicating that Anti-LRP6-1 attenuated angiogenic/inflammatory activities in the retina of OIR via inhibiting Wnt signaling activation (FIG. 20B-D).

Anti-LRP6-1 reduced retinal vascular leakage and leukostasis in STZ-induced diabetic rats. To evaluate the beneficial effect of Anti-LRP6-1 on diabetic retinopathy, Anti-LRP6-1 was intravitreally injected into STZ-induced diabetic rats, with the same dose of non-specific IgG for control. Retinal vascular permeability was measured two weeks following the Anti-LRP6-1 injection using the Evans blue-albumin leakage method, and compared to the IgG control. The result demonstrated that the eyes injected with Anti-LRP6-1 had significantly lower vascular permeability than that injected with IgG (FIG. 21A).

Retinal inflammation such as leukostasis is another hallmark of diabetic retinopathy. To determine the effect of Anti-LRP6-1 on retinal inflammation, a leukostasis assay was performed two weeks following the mAb injection in STZ-diabetic retina. Compared to non-diabetic control, untreated STZ-diabetic and IgG-treated STZ-diabetic retinae showed significantly increased numbers of adherent leukocytes in retinal vasculature (FIG. 21B). The number of leukocytes was significantly decreased in the STZ-diabetic group injected with Anti-LRP6-1, indicating that Anti-LRP6-1 has inhibitory effect on retinal inflammation (FIG. 21B).

As ICAM-1 and TNF-α play important roles in retinal inflammation under diabetes, retinal levels of ICAM-1 and TNF-α were further measured using Western blot analysis. The STZ-induced diabetic retina showed over-expression of ICAM-1 and TNF-α, compared to that in non-diabetic rats. Anti-LRP6-1 but not the non-specific IgG, suppressed the over-expression of ICAM-1 and TNF-α in the diabetic retina (FIG. 21C). In addition, retinal levels of LRP6 were increased in the STZ-induced diabetic retina, compared to that in non-diabetic rats. However, the levels were decreased in the diabetic rats injected with Anti-LRP6-1, but not in that injected with non-specific IgG. These data indicate that activation of the Wnt pathway in the diabetic retina was in part due to over-expression of LRP6, and Anti-LRP6-1 suppresses over-expression of ICAM-1 and TNF-α through down-regulation of LRP6. Taken together, the results demonstrated that Anti-LRP6-1 has beneficial effects on diabetic retinopathy as it attenuates vascular leakage and inflammation in the diabetic retina.

Discussion of Example 3

The previous Examples show dysregulation of Wnt signaling in the retina with diabetic retinopathy and thus indicate that Wnt signaling is a major pathogenic pathway in diabetic retinopathy. The pathogenic role of Wnt signaling in diabetic retinopathy is supported by the observation that DKK1, a specific inhibitor of Wnt signaling, can ameliorate retinal inflammation, vascular leakage and inflammation in diabetic retinopathy models. These findings indicate that Wnt signaling represents a potential therapeutic target of diabetic retinopathy. Despite the well-studied molecular cascade of Wnt signaling, an effective strategy to block the Wnt pathway has not been established for therapeutic application of diabetic retinopathy. Although natural inhibitors of the Wnt signaling such as DKK family members, SERPINA3K and IGF1BP have been identified, there is limitation using these natural inhibitors, including low stability and high costs of production, in their applications as therapeutic compounds. The present Example reports for the first time that an anti-LRP6 monoclonal antibody attenuates retinal vascular leakage and retinal inflammation in diabetic retinopathy via inhibition of the Wnt/β-catenin signaling. In addition, these results provide further support for a causative role of Wnt pathway activation in the development of diabetic retinopathy and indispensability of LRP6 in this context. These observations firstly established that blocking LRP6 by the Anti-LRP6-1 can ameliorate diabetic retinopathy, indicating its therapeutic potential. Moreover, this Example reveals that LRP6 as a sufficient target for blocking the Wnt signaling pathway.

Here, it is demonstrated that Anti-LRP6-1 specific for the first and second propeller domains of LRP6 (E1E2) inhibited Wnt signaling as well as subsequent expression of angiogenic and inflammatory factors in various retinal cells. Based on its inhibitory effect on Wnt signaling and inflammatory factors in vitro, the potential beneficial effects on diabetic retinopathy was determined in animal models. First, in both OIR and diabetic rats, the mAb reduced retinal vascular leakage that is the primary cause of diabetic macular edema (DME), the number one cause of vision loss in diabetic patients. Second, the Anti-LRP6-1 suppressed retinal leukostasis, a key inflammatory change that can lead to impaired endothelium, vascular leakage and closure of capillary which subsequently results in local ischemia. Toward the mechanism for its effects on retinal vascular leakage and leukostasis, these in vitro and in vivo results both showed that Anti-LRP6-1 down-regulates expression of VEGF, ICAM-1 and TNF-α which have been shown to play key roles in retinal inflammation in diabetes. VEGF has been well established as a target gene of Wnt signaling. Sequence analysis of the promoter regions of ICAM-1 and TNF-α revealed that there are TCF/LEF binding sites in a distal region of their promoters, indicating that expression of ICAM-1 and TNF-α may be directly regulated by the Wnt pathway.

The canonical Wnt pathway is a conserved signaling pathway that utilizes single effector, multi-functional transcription activator β-catenin, to regulate expression of a number of target genes. However, diverse spatiotemporal activation of the Wnt pathway arises from multiple combinations among 20 Wnt ligands, 10 Frizzled receptors, and 2 coreceptors, providing numerous diversities. These diversities dampen the therapeutic approaches to inhibit the Wnt pathway via blockage of Wnt ligands or Frizzled receptors. Based on the following facts, however, LRP6 is believed to be an ideal target for blocking Wnt signaling. 1) The canonical Wnt pathway requires one of the two co-receptors, LRP5 or LRP6. 2) Knockout of LRP6 manifests more severe phenotypes than knockout of LRP5, indicating LRP6 plays a more important role than LRP5 in Wnt signaling. 3) LRP6 has a large extracellular domain which is accessible extracellularly by antibodies. In addition, the studies outlined in Example 1 from diabetic patients and animal models clearly demonstrated that blocking LRP6 by DKK1 can ameliorate diabetic retinopathy in animal models. Although the exact mechanism for Wnt signaling activation in diabetes is obscure, the present and previous studies indicated that phosphorylation of LRP6 by lipid oxidation product (4-hydroxynonenal) and by high glucose were sufficient for Wnt signaling activation. Wnt ligand-mediated signaling seems to be the secondary effect in this specific condition. These findings strongly indicate that blocking LRP6, rather than Wnt ligands or Frizzled receptors, provides more effective means to inhibit at least the canonical pathway in diabetic condition.

LRP6 is a type 1 single transmembrane receptor, whose larger ectodomain is composed of four similar EGF-like repeats (E1-E4) with YWTD propeller domain. It has been indicated that LRP6E1E2 domain including the first and second beta-propeller regions cooperates to interact with Wnt-Fz, whereas LRP6E3E4 provides binding site for antagonist DKK1. However, recent in vitro reconstitution studies have shown that Wnt3A binds to the E3E4 domain specifically, and DKK1 to both E1E2 and E3E4 with a cooperative pattern of interactions. Also, it is further determined that Wnt1 preferentially binds to E1 domain, and E3 is sufficient for Wnt3A binding. Despite their different binding sites on LRP6, both Wnt1 and Wnt3A-induced TOPFLASH activities are inhibited by Anti-LRP6-1, indicating that Anti-LRP6-1 not only blocks Wnt1 ligand binding to the E1 domain, but also has inhibitory effect on Wnt3A interaction to E3 domain. The inhibition of Anti-LRP6-1 on Wnt3A-induced Wnt signaling may be explained by a possible mechanism that the bivalent Anti-LRP6-1 binding to LRP6 changes the three dimensional structure of LRP6 ectodomain which causes inaccessibility of Wnt3A. It is also likely that Anti-LRP6-1 may destabilize LRP6 which causes down-regulation of LRP6 available for Wnt ligand binding.

The in vivo studies using OIR and STZ-induced diabetic rat models showed that Anti-LRP6-1 not only inhibits the activation of the canonical Wnt pathway, but also down-regulates LRP6 levels, as retinal levels of total LRP6 are lower in the rats injected with the Anti-LRP6-1 (1 week after the injection) than that injected with the control IgG. However, the cell culture results showed that Anti-LRP6-1 blocks the activation of LRP6 but does not decrease total LRP6 levels after 6 hours treatment. This disparity between in vitro and in vivo results may be explained by the different treatment times by Anti-LRP6-1, since the cultured cells were treated with Anti-LRP6-1 for 6 hours while the retina was treated for 1 week in diabetic rats. The mechanism by which Anti-LRP6-1 down-regulates total level of LRP6 in OIR and diabetic animal models is unclear. However, it is likely that antibody binding to the ectodomain of LRP6 may destabilize LRP6 or induce its internalization and thus, decrease total level of LRP6.

The apparent involvement of Wnt signaling in the regulation of multiple pathogenic mechanisms involved in diabetic retinopathy makes the Wnt pathway an intriguing candidate for targeted therapy. VEGF, which regulates angiogenesis, vascular permeability, and migration of endothelial cells, is over-expressed in the retina of diabetic retinopathy and is a Wnt target gene regulated by β-catenin. This Example showed that Anti-LRP6-1 suppressed over-expression of VEGF in retinal cells exposed to high-glucose and in the retina of OIR rats. In addition, the Wnt pathway is known to regulate retinal inflammation through direct activation of NF-κB or crosstalk with transcription factors including STAT3. The results also indicated that temporal expression of ICAM-1 and TNF-α was in parallel with VEGF expression upon Wnt signaling activation, providing supplementary evidence that their expression is under the control of Wnt signaling. Thus, these findings provide possible evidence that expression of multiple factors known to play important pathogenic roles in diabetic retinopathy are down-regulated by the Wnt pathway.

Recent clinical studies showed that anti-VEGF compounds have promising effect on AMD. In diabetic retinopathy, however, the anti-VEGF compounds are not as effective as in AMD. A possible reason is that diabetic retinopathy is a complex, and multifactorial disorder. Multiple growth factors, in addition to VEGF, are known to play roles in diabetic retinopathy. Therefore, blocking VEGF alone may not be sufficient for ameliorating diabetic retinopathy. Since the Wnt pathway regulates multiple inflammatory and angiogenic factors, such as ICAM-1, PDGF, VEGF, TNF-α, MMP and COX2 which are implicated in diabetic retinopathy, the anti-LRP6 antibody may have a more potent efficacy than anti-VEGF compounds in diabetic retinopathy.

Advantages of using humanized monoclonal antibodies for therapeutic purpose are their high specificity and stability, and low immunogenecity and toxicity, compared to endogenous Wnt inhibitors. It is noteworthy that the present study is simply a proof of concept study. The antibody needs to be humanized. The efficacy, toxicity and immunogenicity will need to be determined.

In conclusion, these findings firstly demonstrated that anti-LRP6 monoclonal antibody has therapeutic potential in diabetic retinopathy. Also, the data implicate LRP6 activation as a major cause of retinal vascular leakage and retinal inflammation, thus expanding involvement of LRP6 and targeted therapy in AMD which proceeded by similar pathogenic mechanisms. Furthermore, these results indicate that the Anti-LRP6-1 decreases the total level of LRP6, indicating its antagonistic effect regardless of different Wnt ligands. Even though questions for side effect on cell survival, stability issue, and efficacy remain, it firstly demonstrated the therapeutic potential of LRP6 targeting therapy in diabetic retinopathy. Further, this study provides a strong rationale for investigating antibody-based, LRP6-targeted therapies in diseases associated with Wnt signaling activation and/or over-expression of LRP6.

Example 4

Effect of Anti-LRP6-1 on CTGF (factor involved in fibrosis): The anti-LRP6 mAb attenuates the hypoxia-induced over-expression of ICAM-1 and CTGF. ICAM-1 is a major adhesion molecular on the endothelium and responsible for leukostasis and endothelium damage in diabetes. CTGF is a fibrogenic factor and is responsible for the basement membrane thickening in DR. Thus, the effect of Anti-LRP6-1 on the expression of ICAM-1 and CTGF was measured. Hypoxia was induced in ARPE19 cells using CoCl$_2$, which induced significant over-expression of ICAM-1 and CTGF, as shown by Western blot analysis (FIG. 22). Anti-LRP6-1 attenuated the over-expression of ICAM-1 and CTGF in a concentration-dependent manner (FIG. 22).

Effect of Anti-LRP6-1 on choroidal neovascularization (wet-AMD): The Wnt pathway is activated in the eyecups with laser-induced CNV, which is attenuated by Anti-LRP6-1. CNV was induced by laser photocoagulation in BN rats. A group of CNV rats received an intravitreal injection of Anti-LRP6-1 and another group received the same amount of non-specific rat IgG, at the same day as the laser. At day 7 after the laser, the rats were perfused and eyecups (retina, RPE and choroid) were isolated for Western blot analysis using an antibody for β-catenin. The results showed that β-catenin was up-regulated in the eyes with laser-CNV, compared to the eyes without laser. Injection of Anti-LRP6-1 significantly decreased β-catenin levels, compared to IgG control (FIG. 23). As accumulation of β-catenin is a key step in activation of Wnt signaling, these results indicate that laser-induced CNV activates the Wnt pathway, while Anti-LRP6-1 attenuates Wnt signaling activation in the CNV eyes.

Anti-LRP6-1 ameliorates laser-induced CNV. The effect of Anti-LRP6-1 injection on laser induced CNV was examined by fluorescein angiography, and the severity of CNV was evaluated by quantifying Grade 4 lesions in fundus images. The result showed that Anti-LRP6-1 significantly decreased numbers of Grade 4 lesions, compared to the control eyes injected with non-specific murine IgG (FIG. 24), indicating a beneficial effect on subretinal vascular leakage and CNV.

Anti-LRP6-1 decreases area of laser-induced CNV. Anti-LRP6-1 was injected intravitreally into the eyes with laser-induced CNV at the same day of the laser, with the same amount IgG as control. Two weeks after the injection, CNV lesions were visualized by fluorescein angiography on the flat-mounted retina-choroid complex. The areas of CNV were measured by computer-assisted image analysis and averaged. The results showed that the Anti-LRP6-1 injected group had significantly decreased CNV areas, compared to that injected with IgG and that without injection (FIG. 25). These results indicate that Anti-LRP6-1 inhibits laser-induced CNV in the rat model.

Thus, in accordance with the presently disclosed inventive concept(s), there has been provided monoclonal antibodies for blocking the Wnt signaling pathway, as well as methods for producing and using same. Although the presently claimed and disclosed inventive concept(s) has been described in conjunction with the specific drawings and language set forth above, it is evident that many alternatives, modifications and variations will be apparent to those skilled in the art. Accordingly, it is intended to embrace all such alternatives, modifications and variations that fall within the spirit and broad scope of the inventive concept(s).

What is claimed is:

1. A method of inhibiting and/or decreasing the occurrence and/or severity of at least one condition selected from the group consisting of inflammation, vascular leakage, fibrosis, abnormal neovascularization, and cancer, said method comprising the step of:
   administering to a subject suffering from or predisposed to the at least one condition a pharmaceutical composition, wherein the pharmaceutical composition inhibits activation of the Wnt signaling pathway, thereby inhibiting and/or decreasing the occurrence and/or severity of the at least one condition, and wherein the pharmaceutical composition comprises a monoclonal antibody or antigen binding fragment thereof and a pharmaceutically acceptable carrier, and wherein the monoclonal antibody or antigen binding fragment thereof comprises:
   a heavy chain variable region CDR1 having the amino acid sequence of SEQ ID NO: 9, a heavy chain variable region CDR2 having the amino acid sequence of SEQ ID NO: 11, a heavy chain variable region CDR3 having the amino acid sequence of SEQ ID NO: 13, a light chain variable region CDR1 having the amino acid sequence of SEQ ID NO: 15, a light chain variable region CDR2 having the amino acid sequence of SEQ ID NO: 17, and a light chain variable region CDR3 having the amino acid sequence of SEQ ID NO: 19; and
   wherein the monoclonal antibody or antigen binding fragment thereof specifically binds to an epitope within the LRP6 extracellular domain, wherein the LRP6 extracellular domain has the amino acid sequence of SEQ ID NO: 2.

2. The method of claim 1, wherein the monoclonal antibody or antigen binding fragment thereof has:
   a heavy chain variable region amino acid sequence that is at least 90% identical to SEQ ID NO: 5, and wherein the CDR1, CDR2, and CDR3 thereof are 100% identical to the amino acid sequences of SEQ ID NOS:9, 11, and 13, respectively; and
   a light chain variable region amino acid sequence that is at least 90% identical to SEQ ID NO: 7, and wherein the CDR1, CDR2, and CDR3 thereof are 100% identical to the amino acid sequences of SEQ ID NOS:15, 17, and 19, respectively.

3. The method of claim 1, wherein the monoclonal antibody or antigen binding fragment thereof is selected from the group consisting of a full length immunoglobulin molecule, an scFv, a Fab fragment, an Fab' fragment, an F(ab')2, an Fv, a disulfide linked Fv, and combinations thereof.

4. The method of claim 1, wherein the monoclonal antibody or antigen binding fragment thereof is humanized.

5. The method of claim 1, wherein the monoclonal antibody or antigen binding fragment thereof binds to the LRP6 extracellular domain with a dissociation constant of less than or equal to about $10^{-7}$ M.

6. The method of claim 1, wherein the monoclonal antibody or antigen binding fragment thereof binds to the same epitope as the antibody produced by the hybridoma having ATCC Designation No. PTA-10663.

7. The method of claim 1, wherein the monoclonal antibody or antigen binding fragment thereof inhibits the binding of both Wnt1 and Wnt3a to LRP6.

8. The method of claim 1, further comprising the step of administering a second agent to the subject, wherein the second agent has a synergistic effect with the monoclonal antibody.

9. The method of claim 8, wherein the second agent is selected from the group consisting of an anti-angiogenic agent, an anti-VEGF reagent, and combinations thereof.

10. The method of claim 1, wherein the condition is fibrosis.

11. The method of claim 1, wherein the condition is colon cancer.

12. A method of inhibiting and/or decreasing the occurrence and/or severity of at least one condition selected from the group consisting of inflammation, vascular leakage, fibrosis, abnormal neovascularization, and cancer, said method comprising the step of:
   administering to a subject suffering from or predisposed to the at least one condition a pharmaceutical composition, wherein the pharmaceutical composition inhibits activation of the Wnt signaling pathway, thereby inhibiting and/or decreasing the occurrence and/or severity of the at least one condition, and wherein the pharmaceutical composition comprises a monoclonal antibody and a pharmaceutically acceptable carrier, and wherein the monoclonal antibody is produced by the hybridoma having ATCC Designation No. PTA-10663.

13. The method of claim 12, further comprising the step of administering a second agent to the subject, wherein the second agent has a synergistic effect with the monoclonal antibody.

14. The method of claim 13, wherein the second agent is selected from the group consisting of an anti-angiogenic agent, an anti-VEGF reagent, and combinations thereof.

15. The method of claim 12, wherein the condition is fibrosis.

16. The method of claim 12, wherein the condition is colon cancer.

17. A method of inhibiting and/or decreasing the occurrence and/or severity of at least one condition selected from the group consisting of inflammation, vascular leakage, fibrosis, abnormal neovascularization, and cancer, said method comprising the step of: administering to a subject suffering from or predisposed to the at least one condition a pharmaceutical composition, wherein the pharmaceutical composition inhibits activation of the Wnt signaling pathway, thereby inhibiting and/or decreasing the occurrence and/or severity of the at least one condition, and wherein the pharmaceutical composition comprises a monoclonal antibody or antigen binding fragment thereof and a pharmaceutically acceptable carrier, wherein the monoclonal antibody or antigen binding fragment thereof specifically binds to the LRP6 extracellular domain having the amino acid sequence of SEQ ID NO: 2, and wherein the isolated monoclonal antibody or antigen binding fragment thereof comprises a heavy chain variable region and a light chain variable region, and wherein the heavy chain variable region has the amino acid sequence of SEQ ID NO:5 and the light chain variable region has the amino acid sequence of SEQ ID NO:7.

18. The method of claim 17, wherein the monoclonal antibody or antigen binding fragment thereof is a single domain antibody.

19. The method of claim 17, further comprising the step of administering a second agent to the subject, wherein the second agent has a synergistic effect with the monoclonal antibody.

20. The method of claim 19, wherein the second agent is selected from the group consisting of an anti-angiogenic agent, an anti-VEGF reagent, and combinations thereof.

21. The method of claim 17, wherein the condition is fibrosis.

22. The method of claim 17, wherein the condition is colon cancer.

* * * * *